US006303347B1

(12) United States Patent
Johnson et al.

(10) Patent No.: US 6,303,347 B1
(45) Date of Patent: *Oct. 16, 2001

(54) AMINOALKYL GLUCOSAMINIDE PHOSPHATE COMPOUNDS AND THEIR USE AS ADJUVANTS AND IMMUNOEFFECTORS

(75) Inventors: David A. Johnson, Hamilton, MT (US); C. Gregory Sowell, Kirkland, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/439,839

(22) Filed: Nov. 12, 1999

Related U.S. Application Data

(63) Continuation-in-part of application No. 08/853,826, filed on May 8, 1997, now Pat. No. 6,113,918.

(51) Int. Cl.$^7$ .......................... C12P 19/04; A61K 45/00; C07H 1/00; C07H 15/00; C07H 11/04
(52) U.S. Cl. .................. 435/101; 424/278.1; 536/1.11; 536/18.4; 536/117; 536/119
(58) Field of Search ................ 424/278.1; 536/1.11, 536/18.4, 117, 119; 435/101

(56) References Cited

U.S. PATENT DOCUMENTS

| | | | |
|---|---|---|---|
| 4,912,094 | 3/1990 | Myers et al. ............................ | 514/54 |
| 6,113,918 | 9/2000 | Johnson ............................ | 424/278.1 |
| B1 4,912,094 | 2/1994 | Meyers et al. ........................ | 514/54 |

OTHER PUBLICATIONS

Bulusu et al., "Cyclic Analogues of Lipid A: Synthesis and Biological Activites," *J. Med. Chem.* 35 (19): 3463–3469, 1992.

Ikeda et al., "Synthesis of Biologically Active N–Acylated L–serine Containing Glucosamine–4–Phosphate Derivatives of Lipid A," *Chem. Pharm. Bull.* 41(10): 1879–1881, 1993.

Miyajima et al., "Lipid A and Related Compounds XXXI. Synthesis of Biologically Active N–Acylated L–Serine–Containing D–Glucosamine 4–Phosphate," *Chem. Pharm. Bull.* 44 (12):2268–2273, 1996.

Shimizu et al., "Antitumor Activity and Biological Effects of Chemically Synthesized Monosaccharide Analogues of Lipid A in Mice," *Chem. Pharm. Bull.* 33 (10):4621–4624, 1985.

Shimizu et al., "Biological Activities of Chemically Synthesized N–acylated Serine–linked Lipid A Analog in Mice," *Int. J. Immunopharmacol.* 16 (8):659–665, 1994.

Shimizu et al., "Biological Activities and Antitumor Effects of Synthetic Lipid A Analogs Linked N–Acylated Serine," *Int. J. Immunopharmacol.* 17 (5):425–431, 1995.

Baldridge, "Synthetic Adjuvants: Recent Developments and Applications," IBC Vaccine Conference, Washington DC, Feb. 1998.

Eustache et al., "New Acyclic Analogues of Lipid A: Synthesis of 4–Phosphonoxybutyl and 3–Phosphonoxypropyl Glycosides of 2–Amino–2–Deoxy–D–Glucose," *Carbohydrate Research* 251 :251–267, Jan. 3, 1994.

Johnson et al., "Synthesis and Biological Evaluation of a New Class of Vaccine Adjuvants: Aminoalkyl Glucosaminide 4–Phosphates (AGPs)," *Bioorg. Med. Chem. Lett.* 9 (15):2273–2278, Aug. 2, 1999.

*Primary Examiner*—Hankyel T. Park
(74) *Attorney, Agent, or Firm*—Seed Intellectual Property Law Group PLLC

(57) ABSTRACT

Aminoalkyl glucosaminide phosphate (AGP) compounds that are adjuvants and immunoeffectors are described and claimed. The compounds have a 2-deoxy-2-amino glucose in glycosidic linkage with an aminoalkyl (aglycon) group. Compounds are phosphorylated at the 4 or 6 carbon on the glucosaminide ring and comprise three 3-alkanoyloxyalkanoyl residues. The compounds augment antibody production in immunized animals as well as stimulate cytokine production and activate macrophages. Methods for using the compounds as adjuvants and immunoeffectors are also disclosed.

36 Claims, No Drawings

US 6,303,347 B1

AMINOALKYL GLUCOSAMINIDE PHOSPHATE COMPOUNDS AND THEIR USE AS ADJUVANTS AND IMMUNOEFFECTORS

CROSS-REFERENCE TO RELATED APPLICATION

This application is a continuation-in-part of U.S. application Ser. No. 08/853,826, filed May 8, 1997 (which application is hereby incorporated by reference in its entirety).

TECHNICAL FIELD

This invention relates generally to aminoalkyl glucosaminide phosphate (AGP) compounds which have activity as adjuvants and immunoeffectors, and methods and compositions related thereto.

BACKGROUND OF THE INVENTION

Humoral immunity and cell-mediated immunity are the two major branches of the mammalian immune response. Humoral immunity involves the generation of antibodies to foreign antigens. Antibodies are produced by B-lymphocytes. Cell-mediated immunity involves the activation of T-lymphocytes which either act upon infected cells bearing foreign antigens or stimulate other cells to act upon infected cells. Both branches of the mammalian immune system are important in fighting disease. Humoral immunity is the major line of defense against bacterial pathogens. In the case of viral disease, the induction of cytotoxic T lymphocytes (CTLs) appears to be crucial for protective immunity. An effective vaccine stimulates both branches of the immune system to protect against disease.

Vaccines present foreign antigens from disease causing agents to a host so that the host can mount a protective immune response. Often vaccine antigens are killed or attenuated forms of the microbes which cause the disease. The presence of non-essential components and antigens in these killed or attenuated vaccines has encouraged considerable efforts to refine vaccine components including developing well-defined synthetic antigens using chemical and recombinant techniques. The refinement and simplification of microbial vaccines, however, has led to a concomitant loss in potency. Low-molecular weight synthetic antigens, though devoid of potentially harmful contaminants, are themselves not very immunogenic. These observations have led investigators to add adjuvants to vaccine compositions to potentiate the activity of the refined vaccine components.

Presently, the only adjuvant licensed for human use in the United States is alum, a group of aluminum salts (e.g., aluminum hydroxide, aluminum phosphate) in which vaccine antigens are formulated. Particulate carriers like alum serve to promote the uptake, processing and presentation of soluble antigens by macrophages. Alum, however, is not without side-effects and enhances humoral (antibody) immunity only.

An effective adjuvant potentiates both a humoral and cellular immune response in vaccinated animals. Further, an adjuvant must enhance a host's natural immune response and not aggravate the host system. A well-defined synthetic adjuvant free from extraneous matter which is stable and easy to manufacture would provide these qualities. Compounds that have been prepared and tested for adjuvanticity (Shimizu et al. 1985, Bulusu et al. 1992, Ikeda et al. 1993, Shimizu et al. 1994, Shimizu et al. 1995, Miyajima et al. 1996), however, often display toxic properties, are unstable and/or have unsubstantial immunostimulatory effects.

The discovery and development of effective adjuvants is essential for improving the efficacy and safety of existing vaccines. Adjuvants impart synthetic peptides and carbohydrate antigens with sufficient immunogenicity to insure the success of the synthetic vaccine approach. There remains a need for new compounds having potent immunomodulating effects.

SUMMARY OF THE INVENTION

The compounds of the subject invention are aminoalkyl glucosaminide phosphate compounds (AGPs) which are adjuvants and immunoeffectors. An aminoalkyl (aglycon) group is glycosidically linked to a 2-deoxy-2-amino-α-D-glucopyranose (glucosaminide) to form the basic structure of the claimed molecules. The compounds are phosphorylated at the 4 or 6 carbon on the glucosaminide ring. Further, the compounds possess three 3-alkanoyloxyalkanoyl residues.

The compounds of the subject invention are immunoeffector molecules augmenting antibody production in immunized animals, stimulating cytokine production and activating macrophages. In accordance with the -subject invention, methods for using these compounds as adjuvants and immunoeffectors are disclosed.

DETAILED DESCRIPTION OF THE INVENTION

The compounds of the subject invention are adjuvant and immunoeffector molecules which are aminoalkyl glucosaminide phosphates (AGPs). The compounds comprise a 2-deoxy-2-amino-α-D-glucopyranose (glucosaminide) in glycosidic linkage with an aminoalkyl (aglycon) group. Compounds are phosphorylated at the 4 or 6 carbon on the glucosaminide ring and have three alkanoyloxyalkanoyl residues. The compounds of the subject invention are described generally by Formula I,

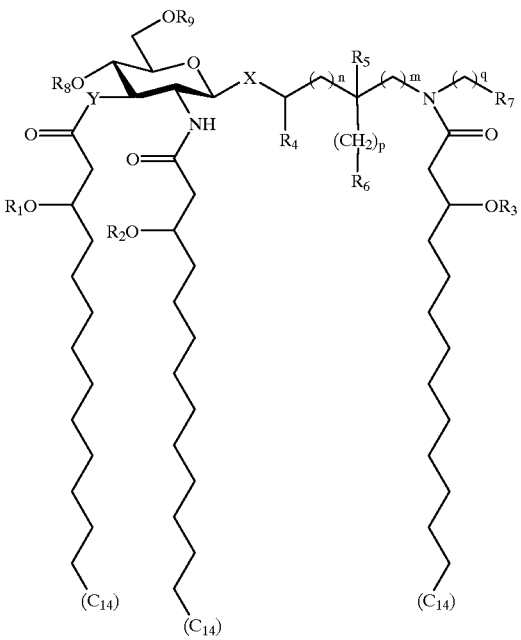

wherein X represents an oxygen or sulfur atom in either the axial or equitorial position, Y represents an oxygen atom or NH group, "n", "m", "p" and "q" are integers from 0 to 6, $R_1$, $R_2$, and $R_3$ represent normal fatty acyl residues having 1 to 20 carbon atoms and where one of $R_1$, $R_2$ or $R_3$ is optionally hydrogen, $R_4$ and $R_5$ are hydrogen or methyl, $R_6$ and $R_7$ are hydrogen, hydroxy, alkoxy, phosphono, phosphonooxy, sulfo, sulfooxy, amino, mercapto, cyano, nitro, formyl or carboxy and esters and amides thereof; $R_8$ and $R_9$ are phosphono or hydrogen. The configuration of the 3' stereogenic centers to which the normal fatty acyl residues are attached is R or S, but preferably R. The stereochemistry of the carbon atoms to which $R_4$ or $R_5$ are attached can be R or S. All stereoisomers, both enantiomers and diastereomers, and mixtures thereof, are considered to fall within the scope of the subject invention.

The heteroatom X of the compounds of the subject invention can be oxygen or sulfur. In a preferred embodiment, X is oxygen and typically in the equitorial position. Although the stability of the molecules could be effected by a substitution at X, the immunomodulating activity of molecules with these substitutions is not expected to change.

The number of carbon atoms between heteroatom X and the aglycon nitrogen atom is determined by variables "n" and "m". Variables "n" and "m" can be integers from 0 to 6. In a preferred embodiment, the total number of carbon atoms between heteroatom X and the aglycon nitrogen atom is from about 2 to about 6 and most preferably from about 2 to about 4.

The compounds of the subject invention are aminoalkyl glucosaminide compounds which are phosphorylated. Compounds can be phosphorylated at position 4 or 6 ($R_8$ or $R_9$) on the glucosaminide ring and are most effective if phosphorylated on at least one of these positions. In a preferred embodiment, $R_8$ is phosphono and $R_9$ is hydrogen.

In one embodiment, the compounds of the subject invention are hexaacylated, that is they contain a total of six fatty acid residues. The aminoalkyl glucosaminide moiety is acylated at the 2-amino and 3-hydroxyl groups of the glucosaminide unit and at the amino group of the aglycon unit with 3-hydroxyalkanoyl residues. In Formula I, these three positions are acylated with 3-hydroxytetradecanoyl moieties. The 3-hydroxytetradecanoyl residues are, in turn, substituted with normal fatty acids ($R_1$–$R_3$), providing three 3-n-alkanoyloxytetradecanoyl residues or six fatty acid groups in total.

In another embodiment, the compounds of the subject invention are pentaacylated, that is they contain a total of five fatty acid residues. More specifically, the 3-hydroxytetradecanoyl residues of Formula I are substituted with normal fatty acids at two of the three $R_1$, $R_2$ and $R_3$ positions, with the third $R_1$, $R_2$ or $R_3$ position being hydrogen. In other words, at least one of —$OR_1$, —$OR_2$ or —$OR_3$ is hydroxyl.

The chain length of normal fatty acids $R_1$–$R_3$ can be from 1 to about 20, and typically from about 7 to about 16 carbons. Preferably, $R_1$–$R_3$ are from about 9 to about 14 carbons. The chain lengths of these normal fatty acids can be the same or different. Although, only normal fatty acids are described, it is expected that unsaturated fatty acids (i.e. fatty acid moieties having double or triple bonds) substituted at $R_1$–$R_3$ on the compounds of the subject invention would produce biologically active molecules. Further, slight modifications in the chain length of the 3-hydroxyalkanoyl residues are not expected to dramatically effect biological activity.

The compounds of the subject invention are adjuvants and immunoeffectors which enhance the generation of antibody in immunized animals, stimulate the production of cytokines and stimulate a cell-mediated immune response including a cytotoxic T-lymphocyte response. In methods for effecting the immune response of an individual, the compounds of the subject invention can be formulated with a pharmaceutically acceptable carrier for injection or ingestion. As used herein, "pharmaceutically acceptable carrier" means a medium which does not interfere with the immunomodulatory activity of the active ingredient and is not toxic to the patient to whom it is administered. Pharmaceutically acceptable carriers include oil-in-water or water-in-oil emulsions, aqueous compositions, liposomes, microbeads and microsomes. For example, the carrier may be a microsphere or microparticle having a compound of this invention within the matrix of the sphere or particle or adsorbed on the surface of the sphere or particle. The carrier may also be an aqueous solution or micellar dispersion containing triethylamine, triethanolamine or other agent that renders the formulation alkaline in nature, or a suspension containing aluminum hydroxide, calcium hydroxide, calcium phosphate or tyrosine adsorbate.

Formulations of the compounds of the subject invention that can be administered parenterally, i.e. intraperitoneally, subcutaneously or intramuscularly include the following preferred carriers. Examples of preferred carriers for subcutaneous use include a phosphate buffered saline (PBS) solution and 0.01–0.1% triethanolamine in USP Water for Injection. Suitable carriers for intramuscular injection include 10% USP ethanol, 40% propylene glycol and the balance an acceptable isotonic solution such as 5% dextrose.

Examples of preferred carriers for intravenous use include 10% USP ethanol, 40% USP propylene glycol and the balance USP Water for Injection. Another acceptable carrier includes 10% USP ethanol and USP Water for Injection; yet another acceptable carrier is 0.01–0.1% triethanolamine in USP Water for Injection. Pharmaceutically acceptable parenteral solvents are such as to provide a solution or dispersion may be filtered through a 5 micron filter without removing the active ingredient.

Examples of carriers for administration via mucosal surfaces depend upon the particular route. When administered orally, pharmaceutical grades of mannitol, starch, lactose, magnesium stearate, sodium saccharide, cellulose, magnesium carbonate and the like, with mannitol being preferred. When administered intranasally, polyethylene glycol or glycols, sucrose, and/or methylcellulose, and preservatives such as benzalkonium chloride, EDTA, may be used, with polyethylene glycols being preferred, and when administered by inhalation, suitable carriers are polyethylene glycol or glycols, methylcellulose, dispensing agents, and preservatives, with polyethylene glycols being preferred.

The compounds of the subject invention are administered to an individual in "an effective amount" to effect or enhance the individual's immune response. As used herein, "an effective amount" is that amount which shows a response over and above the vehicle or negative controls. The precise dosage of the compounds of the subject invention to be administered to a patient will depend upon the particular AGP used, the route of administration, the pharmaceutical composition, and the patient. For example, when administered subcutaneously to enhance an antibody response, the amount of AGP used is from 1 to about 250 micrograms, preferably from about 25 to about 50 micrograms based upon administration to a typical 70 kg adult patient.

In vaccine compositions, the AGPs of the subject invention are administered to a warm-blooded animal, including humans, with an antigen. The amount of antigen administered to elicit a desired response can be readily determined by one skilled in the art and will vary with the type of antigen administered, route of administration and immunization schedule. For example, 0.2 µg of tetanus toxoid administered with the claimed compounds subcutaneously to a mouse in two immunization 21 days apart elicited a humoral immune response to that antigen.

The compounds of the subject invention are synthesized by coupling an N-acyloxyacylated or N-protected aminoalkanol or aminoalkanethiol (aglycon unit) with a suitably protected and/or 3-O-acyloxyacylated glucosaminide unit. In one preferred method for preparing the compounds of the subject invention (Scheme 1), an N-(2,2,2-trichloroethoxycarbonyl (Troc))-protected glycosyl halide 1 (Z=F, Cl, Br) is coupled with an N-[(R)-3-n-alkanoyloxytetradecanoyl]aminoalkanol or thiol 2 (possessing $R_5$ and $R_6$ in suitably protected form) via a Koenigs-Knorr type reaction in the presence of mercury or silver salts to give glycoside intermediate 3. Preferably, the glucosaminide unit 1 possesses an anomeric chloride atom (Z=Cl), and the coupling catalyst is silver trifluoromethanesulfonate. Intermediate 3 can also be prepared by coupling the aglycon unit 2 with an N-Troc-protected glycosyl acetate (Z=OAc) or related activated derivative in the presence of a Lewis acid such as boron trifluoride etherate. By "activated" is meant having an appropriate displaceable leaving group "Z" attached to the anomeric center of the glucosaminide unit. Glucosaminide unit 1 bears an (R)-3-n-alkanoyloxytetradecanoyl residue on the 3-position, and suitable protecting groups on the 6-hydroxyl and 4-phosphate moieties. Typical protecting groups for the phosphate group include, but are not limited to, phenyl, benzyl, and o-xylyl. The phosphate group is protected preferably with two phenyl groups. The 6-position can be temporarily protected by blocking groups commonly used in sugar chemistry such as silyl, benzyl, or benzyloxymethyl ethers or, alternatively, an alkyl carbonate. The 6-hydroxyl group is protected preferably as a 1,1-dimethyl-2,2,2-trichloroethyl carbonate (TCBOC).

The trichloroethyl-based protecting group(s) in the Koenigs-Knorr coupled product 3 are removed with zinc and the glucosaminide nitrogen is selectively acylated with a (R)-3-n-alkanoyloxytetradecanoic acid 4 in the presence of a suitable coupling reagent to give the hexaacylated derivative 5. The remaining protecting groups in 5 are then cleaved by catalytic hydrogenation in the presence of a palladium or platinum catalyst or by other appropriate means to give compounds of Formula (I).

A suitable starting material for the synthesis of glycosyl donor 1 is 2-(trimethylsilyl)ethyl 2-amino-2-deoxy-4,6-O-isopropylidene-β-D-glucopyranoside which can be prepared from commercially available D-glucosaminide hydrochloride using published procedures. The conversion of the 2-(trimethylsilyl)ethyl glycoside starting material to glycosyl donor 1 can be achieved by methods known in the art or modifications thereof which are described herein. The aglycon unit 2 can be prepared by N-acyloxyacylation of commercially available starting materials with an appropriate (R)-3-n-alkanoyloxytetradecanoic acid 4, or N-acyloxyacylation of starting materials that can be obtained by known methods in the chemical literature. Alternatively, the N-acyloxyacyl residue in 2 can be substituted with an appropriate amine protecting group which is removed subsequent to the coupling reaction such as is described in the second preferred embodiment below.

In a second preferred method for preparing the compounds of the subject invention (Scheme 2), introduction of the (R)-3-n-alkanoyloxytetradecanoyl and phosphate groups into the glucosaminide and aglycon units is performed subsequent to the glycosylation (coupling) reaction using N- and O-protecting groups suitable for the chemical differentiation of the amino and hydroxyl groups present. Preferably, the N-Troc-protected glycosyl donor 6 is coupled with an N-allyloxycarbonyl (AOC)-protected aminoalkanol or thiol 7 in the presence of an appropriate catalyst to give the aminoalkyl β-glycoside 8. Most preferably, the glycosyl donor 6 possesses an anomeric acetoxy group (Z=OAc), and the coupling catalyst is boron trifluoride etherate. Other N-protecting groups for the aglycon amino group include, but are not limited to, commonly employed carbamates obvious to one skilled in the art such as t-butyl (t-BOC), benzyl (Cbz), 2,2,2-trichloroethyl (Troc), and 9-fluorenylmethyl(Fmoc).

Base-induced cleavage of the acetate groups in coupling product 8 and 4,6-acetonide formation under standard conditions known in the art gives intermediate 9. 3-O-Acylation of 9 with (R)-3-n-alkanoyloxytetradecanoic acid 4, followed by palladium(0)-mediated removal of the aglycon N-AOC group and N-acylation with (R)-3-n-alkanoyloxytetradecanoic acid 4 provides intermediate 10. Acetonide hydrolysis and functionalization of the 4- and 6-positions as described herein for the preparation of glycosyl donor 1 gives intermediate 3 (Y=O) which is then processed as in Scheme 1 to afford compounds of general Formula (I).

The present invention is further described by way of the following non-limiting Examples and Test Examples which are given for illustrative purposes only. It is important to note that the introduction of the (R)-3-n-alkanoyloxytetradecanoyl groups and the phosphate group(s) into the glucosaminide and aglycon units do not necessarily have to be performed in the order shown in Schemes 1 and 2 or described in the Examples shown below.

Scheme 1
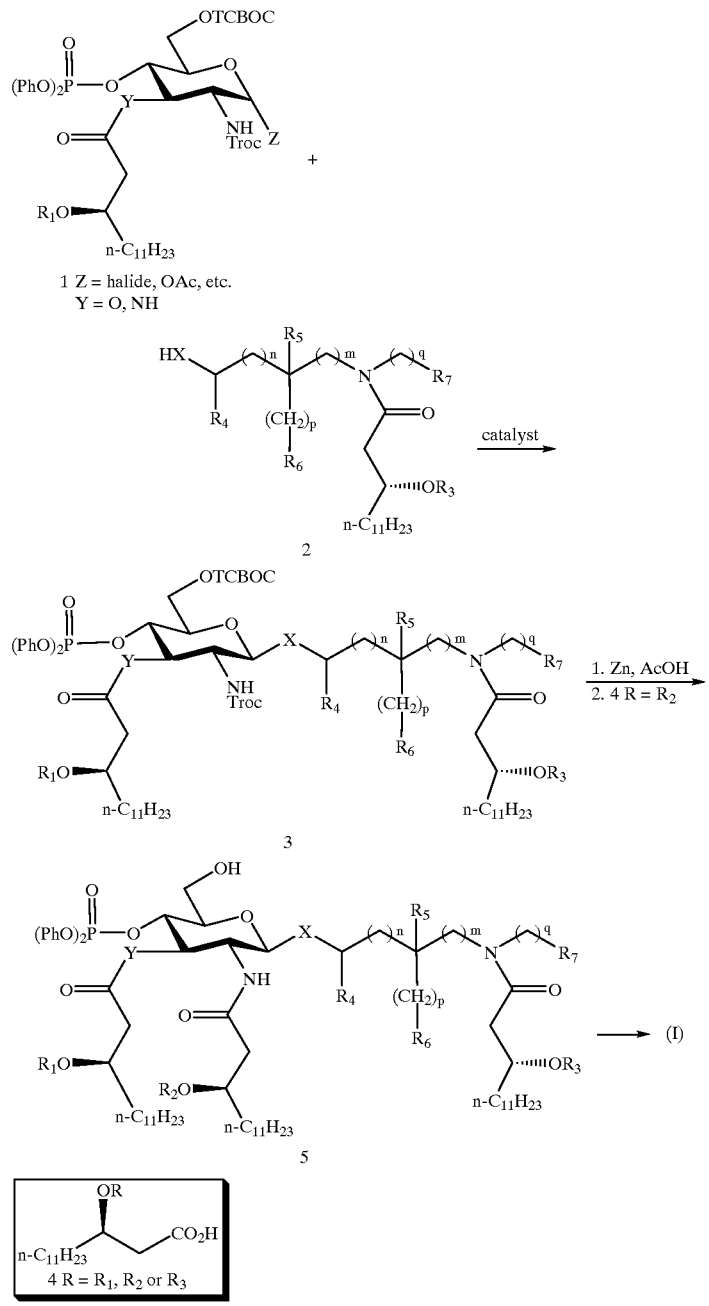
Scheme 2
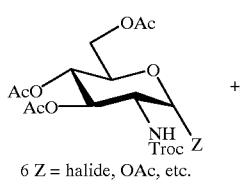

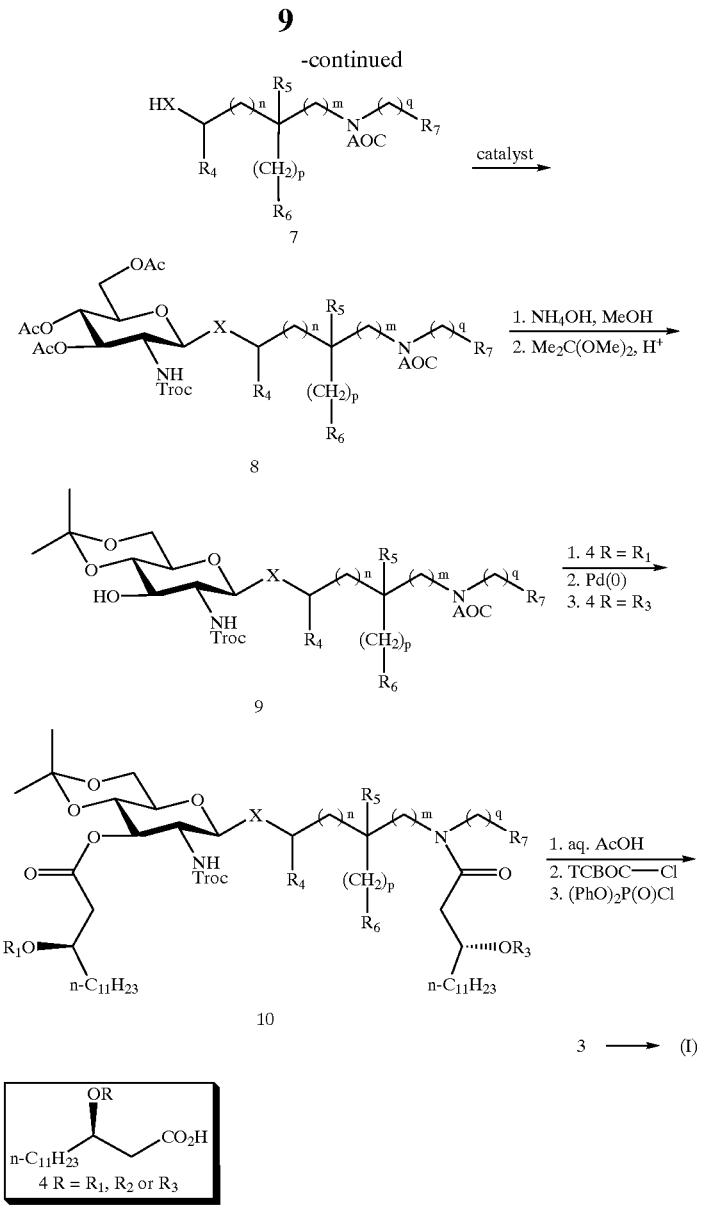

Examples 1–43 describe methods of making the AGP compounds of the subject invention. Test Examples 1–13 describe assays conducted to the determine the immunogenicity of these compounds. Table 1 lists the chemical composition and experimental reference numbers for each compound in these examples.

TABLE 1

| Example | Ref. No. | $R_1$–$R_3$ | n | p | $R_6$ | q | $R_7$ |
|---|---|---|---|---|---|---|---|
| 1 | — | — | — | — | — | — | — |
| 2 | B1* | n-$C_{13}H_{27}$CO | 0 | 1 | OH | 0 | H |
| 3 | B2** | n-$C_{13}H_{27}$CO | 0 | 1 | OH | 0 | H |
| 4 | B3 | n-$C_{11}H_{23}$CO | 0 | 1 | OH | 0 | H |
| 5 | B4 | n-$C_{10}H_{21}$CO | 0 | 1 | OH | 0 | H |
| 6 | B5 | n-$C_9H_{19}$CO | 0 | 1 | OH | 0 | H |
| 7 | B6*** | n-$C_9H_{19}$CO | 0 | 1 | OH | 0 | H |
| 8 | B7 | n-$C_8H_{17}$CO | 0 | 1 | OH | 0 | H |
| 9 | B8 | n-$C_6H_{13}$CO | 0 | 1 | OH | 0 | H |
| 10 | B9 | n-$C_9H_{19}$CO | 1 | 1 | OH | 0 | H |
| 11 | B10 | n-$C_9H_{19}$CO | 0 | 2 | OH | 0 | H |
| 12 | B11 | n-$C_{13}H_{27}$CO | 0 | 0 | $CO_2H$ | 0 | H |
| 13 | B12 | n-$C_{11}H_{23}$CO | 0 | 0 | $CO_2H$ | 0 | H |
| 14 | B13 | n-$C_{10}H_{21}$CO | 0 | 0 | $CO_2H$ | 0 | H |

TABLE 1-continued

| Example | Ref. No. | $R_1$–$R_3$ | n | p | $R_6$ | q | $R_7$ |
|---|---|---|---|---|---|---|---|
| 15 | B14** | n-$C_9H_{19}$CO | 0 | 0 | $CO_2H$ | 0 | H |
| 16 | B15* | n-$C_9H_{19}$CO | 0 | 0 | $CO_2H$ | 0 | H |
| 17 | B16 | n-$C_8H_{17}$CO | 0 | 0 | $CO_2H$ | 0 | H |
| 18 | B17 | n-$C_7H_{15}$CO | 0 | 0 | $CO_2H$ | 0 | H |
| 19 | B18 | n-$C_6H_{13}$CO | 0 | 0 | $CO_2H$ | 0 | H |
| 20 | B19 | n-$C_{13}H_{27}$CO | 0 | 0 | H | 0 | H |
| 21 | B20 | n-$C_9H_{19}$CO | 0 | 0 | H | 0 | H |
| 22 | B21 | n-$C_{13}H_{27}$CO | 1 | 0 | H | 0 | H |
| 23 | B22 | n-$C_{13}H_{27}$CO | 2 | 0 | H | 0 | H |
| 24 | B23 | n-$C_{13}H_{27}$CO | 4 | 0 | H | 0 | H |
| 25 | B24 | n-$C_{13}H_{27}$CO | 0 | 0 | $CONH_2$ | 0 | H |
| 26 | B25 | n-$C_9H_{19}$CO | 0 | 0 | $CONH_2$ | 0 | H |
| 27 | B26 | n-$C_{13}H_{27}$CO | 0 | 0 | $CO_2Me$ | 0 | H |
| 28 | B27 | n-$C_{13}H_{27}$CO | 0 | 0 | H | 1 | $CO_2H$ |
| 29 | B28 | n-$C_9H_{19}$CO | 1 | 0 | H | 1 | $CO_2H$ |
| 30 | B29 | n-$C_5H_{11}$CO | 0 | 0 | $CONH_2$ | 0 | H |
| 31 | B30 | $R_1 = R_3 = $ n-$C_9H_{19}$CO<br>$R_2 = $ n-$C_5H_{11}$CO | 0 | 0 | $CONH_2$ | 0 | H |
| 32 | B31 | n-$C_5H_{11}$CO | 0 | 0 | H | 0 | H |
| 33 | B32 | $R_1 = $ n-$C_{13}H_{27}$CO<br>$R_2 = $ n-$C_{17}H_{35}$CO<br>$R_3 = $ n-$C_{15}H_{31}$CO | 0 | 0 | H | 0 | H |
| 34 | B34 | n-$C_5H_{11}$CO | 0 | 0 | $CO_2H$ | 0 | H |
| 35 | B35 | $R_1 = $ n-$C_5H_{11}$CO<br>$R_2 = R_3 = $ n-$C_9H_{19}$CO | 0 | 0 | $CO_2H$ | 0 | H |
| 36 | B36 | $R_1 = R_3 = $ n-$C_9H_{19}$CO<br>$R_2 = $ n-$C_5H_{11}$CO | 0 | 0 | $CO_2H$ | 0 | H |
| 37 | B37 | $R_1 = R_2 = $ n-$C_9H_{19}$CO<br>$R_3 = $ n-$C_5H_{11}$CO | 0 | 0 | $CO_2H$ | 0 | H |
| 38 | B38 | $R_1 = $ n-$C_9H_{11}$CO<br>$R_2 = R_3 = $ n-$C_5H_{11}$CO | 0 | 0 | $CO_2H$ | 0 | H |
| 39 | B39 | $R_1 = R_3 = C_5H_{11}$CO<br>$R_2 = $ n-$C_9H_{19}$CO | 0 | 0 | $CO_2H$ | 0 | H |
| 40 | B40 | $R_1 = R_2 = $ n-$C_5H_{11}$CO<br>$R_3 = $ n-$C_9H_{19}$CO | 0 | 0 | $CO_2H$ | 0 | H |
| 41 | B41 | $R_1 = R_3 = $ n-$C_9H_{19}$CO<br>$R_2 = $ n-$C_5H_{11}$CO | 0 | 1 | OH | 0 | H |
| 42 | B42 | n-$C_9H_{11}$CO | 0 | 2 | $CO_2H$ | 0 | H |
| 43 | B43 | $R_1 = $ n-$C_{13}H_{27}$CO<br>$R_2 = $ n-$C_{11}H_{23}$CO<br>$R_3 = $ H | 0 | 0 | $CO_2H$ | 0 | H |

For all Examples shown: X = Y = O; $R_4 = R_5 = $ H; m = 0; $R_8 = $ phosphono; $R_9 = $ H.
*the stereochemistry of the carbon atom to which $R_5$ is attached is S.
**the stereochemistry of the carbon atom to which $R_5$ is attached is R.
***$R_8$ is H and $R_9$ is phosphono.

EXAMPLE 1

PREPARATION OF (R)-3-N-ALKANOYLOXYTETRADECANOIC ACIDS (4).

(1) A solution of methyl 3-oxotetradecanoate (19 g, 0.074 mol) in MeOH (100 mL) was degassed by sparging with argon (15 min). [(R)-Ru(Binap)Cl]$_2$·NEt$_3$ catalyst (0.187 g, 0.111 mmol) and 2 N aqueous HCl (0.5 mL) were added and the resulting mixture was hydrogenated at 60 psig and 40–50° C. for 18 h. The reaction was diluted with hexanes (250 mL), filtered through a short column of silica gel, and concentrated. The crude product was dissolved in tetrahydrofuran (THEF; 200 mL), treated 2.4 N aqueous LiOH (83 mL, 0.2 mol) and stirred vigorously at room temperature for 4 h. The resulting slurry was partitioned between ether (200 mL) and 1 N aqueous HCl (200 mL) and the layers separated. The aqueous layer was extracted with ether (100 mL) and the combined ethereal extracts were dried (Na$_2$SO$_4$) and concentrated. The crude hydroxy acid was dissolved in hot acetonitrile (250 mL), treated with dicyclohexylamine (DCHA; 17 ml, 0.085 mol) and stirred at 60° C. for 1 h. The product that crystallized upon cooling was collected and recrystallized from acetonitrile (650 mL) to yield 28.6 g (91%) of dicyclohexylammonium (R)-3-hydroxytetradecanoate as a colorless solid: mp 94–95° C.; $^1$H NMR (CDCl$_3$) δ 0.88 (t, 3 H, J~6.5 Hz), 1.05–1.58 (m, 24H), 1.65 (m, 2H), 1.80 (m, 4H), 2.01 (br d, 4H) 2.18 (dd, 1H, J=15.7, 9.4 Hz), 2.36 (dd, 1H, J=15.7, 2.6 Hz), 2.94 (m, 2H), 3.84 (m, 1H).

(2) To a mixture of the compound prepared in (1) above (50 g, 0.117 mol) and 2,4'-dibromoacetophenone (39 g, 0.14 mol) in EtOAc (2.3 L) was added triethylamine (19.6 mL, 0.14 mol) and the resulting solution was stirred for 18 h at room temperature. The voluminous precipitate that formed was collected and triturated with warm EtOAc (3×400 mL). The combined triturates and filtrate were washed with 1 M aq. HCl, saturated aq. NaCl and dried (Na$_2$SO$_4$). Volatiles were removed under reduced pressure and the crude product obtained was crystallized from EtOAc-hexanes to give 47.2 g (91%) of (R)-3-hydroxytetradecanoic acid p-bromophenacyl ester as a colorless solid: mp 109–109.5° C.; $^1$H NMR (CDCl$_3$) δ 0.88 (~t, 3H, J~6.5 Hz) 1.15–1.70 (m, 20H), 2.56 (dd, 1H, J=15.1, 9.1 Hz), 2.69 (dd, 1H, J=15.1, 2.9 Hz), 3.27 (br s, 1H), 4.12 (m, 1H), 5.31 (d, 1H, J=16.5 Hz), 5.42 (d, 1H, J=16.5 Hz), 7.65 (d, 2H, J=8.5 Hz), 7.78 (d, 2H, J=8.5 Hz).

(3) A solution of the compound prepared in (2) above (4.6 g, 10.4 mmol) in CH$_2$Cl$_2$ (50 mL) containing 4-dimethylaminopyridine (0.12 g, 1.0 mmol) and pyridine (5 mL, 62 mmol) was treated at room temperature with myristoyl chloride (3.1 mL, 11.4 mmol). After stirring for 5 h at room temperature MeOH (0.5 mL) was added, and the reaction mixture was concentrated. The residue was partitioned between $Et_2O$ (150 mL) and cold 10% aqueous HCl (50 mL) and the layers separated. The ethereal layer was dried ($Na_2SO_4$) and concentrated and the residue obtained was purified on a short pad of silica gel with 5% EtOAc-hexanes. The diester was dissolved in AcOH (42 mL) and treated with three equal portions of zinc dust (6 g, 90 mmol) at 60° C. over a 1 h period. After an additional hour at 60° C., the cooled reaction mixture was sonicated (5 min), filtered through Celite® and concentrated. The residue was purified by flash chromatography on silica gel with 10% EtOAc-hexanes to give 4.17 g (82%) of (R)-3-tetradecanoyloxytetradecanoic acid as a colorless solid: mp 28–29° C.; $^1$H NMR ($CDCl_3$) δ 0.88 (~t, 6H), 1.15–1.40 (m, 38H), 1.50–1.70 (m, 4H), 2.28 (t, 2H, J=7.4 Hz), 2.56 (dd, 1H, J=15.9, 5.8 Hz), 2.63 (dd, 1H, J=15.9, 7.1 Hz), 5.21 (m, 1H).

(4) In the same manner as described in Example 1-(3), the compound prepared in Example 1-(2) (2.5 g, 5.68 mmol) was acylated with lauroyl chloride (1.45 mL, 6.25 mmol) in the presence of pyridine (0.57 mL, 7.0 mmol) in $CH_2Cl_2$ (60 mL) and then deprotected with zinc (9.3 g, 142 mmol) in AcOH (40 mL) to afford (R)-3-dodecanoyloxytetradecanoic acid as a colorless oil: $^1$H NMR ($CDCl_3$) δ 0.90 (t, 6H, J=6.5 Hz), 1.0–1.75 (m, 46H), 2.30 (m, 2H), 2.62 (m, 2H), 5.22 (m, 1H).

(5) A solution of the compound prepared in Example 1-(2) (2.5 g, 5.68 mmol) was treated with undecanoic acid (1.16 g, 6.25 mmol) and EDCMeI (2.08 g, 7.0 mmol) in $CH_2Cl_2$ (60 mL) and then deprotected as described in Example 1-(3) with zinc (9.3 g, 142 mmol) in AcOH (40 mL) to afford (R)-3 -undecanoyloxytetradecanoic acid as a colorless oil: $^1$H NMR ($CDCl_3$) δ 0.89 (t, 6H, J=6.7 Hz), 1.0–1.75 (m, 44H), 2.29 (m, 2H), 2.61 (m, 2H), 5.22 (m, 1H).

(6) In the same manner as described in Example 1-(3), the compound prepared in Example 1-(2) (4.4 g, 10 mmol) was acylated with decanoyl chloride (2.3 mL, 11 mmol) in the presence of pyridine (1.2 mL, 15.0 mmol) in $CH_2Cl_2$ (100 mL) and then deprotected with zinc (16.4 g, 250 mmol) in AcOH (60 mL) to afford (R)-3-decanoyloxytetradecanoic acid as a colorless oil: $^1$H NMR ($CDCl_3$) δ 0.89 (t, 6H, J=6.8 Hz), 1.0–1.75 (m, 34H), 2.29 (t, 2H, J=7.4 Hz), 2.61 (t, 2H, J=4.2 Hz), 5.22 (m, 1H).

(7) In the same manner as described in Example 1-(3), the compound 71. prepared in Example 1-(2) (2.5 g, 5.68 mmol) was acylated with nonanoyl chloride (1.13 mL, 6.25 mmol) in the presence of pyridine (0.57 mL, 7.0 mmol) in $CH_2Cl_2$ (60 mL) and then deprotected with zinc (9.3 g, 142 mmol) in AcOH (40 mL) to afford (R)-3-nonanoyloxytetradecanoic acid as a colorless oil: $^1$H NMR ($CDCl_3$) δ 0.89 (t, 6H, J=6.9 Hz), 1.0–1.75 (m, 32H), 2.29 (t, 2H, J=7.5 Hz), 2.61 (m, 2H), 5.22 (m, 1H).

(8) In the same manner as described in Example 1-(3), the compound prepared in Example 1-(2) (2.5 g, 5.68 mmol) was acylated with octanoyl chloride (1.07 mL, 6.25 mmol) in the presence of pyridine (0.57 mL, 7.0 mmol) in $CH_2Cl_2$ (60 mL) and then deprotected with zinc (9.3 g, 142 mmol) in AcOH (40 mL) to afford (R)-3-octanoyloxytetradecanoic acid as a colorless oil: $^1$H NMR ($CDCl_3$) δ 0.92 (t, 6H, J=6.9 Hz), 1.0–1.75 (m, 30H), 2.32 (t, 2H, J=7.4 Hz), 2.63 (t, 2H, J=4.4 Hz), 5.23 (m, 1H).

(9) In the same manner as described in Example 1-(3), the compound prepared in Example 1-(2) (2.5 g, 5.68 mmol) was acylated with heptanoyl chloride (0.97 mL, 6.25 mmol) in the presence of pyridine (0.57 mL, 7.0 mmol) in $CH_2Cl_2$ (60 mL) and then deprotected with zinc (9.3 g, 142 mmol) in AcOH (40 mL) to afford (R)-3-heptanoyloxytetradecanoic acid as a colorless oil: $^1$H NMR ($CDCl_3$) δ 0.89 (t, 6H, J=6.8 Hz), 1.0–1.75 (m, 28H), 2.29 (t, 2H, J=7.4 Hz), 2.61 (d, 2H, J=5.8 Hz), 5.22 (m, 1H).

EXAMPLE 2

B1

PREPARATION OF 3-HYDROXY-(S)-2-[(R)-3-TETRADECANOYLOXYTETRADECANOYLAMINO]PROPYL 2-DEOXY-4-O-PHOSPHONO-2-[(R)-3-TETRADECANOYLOXYTETRADECANOYLAMINO]-3-O-[(R)-3-TETRADECANOYLOXYTETRADECANOYL]-β-D-GLUCOPYRANOSIDE TRIETHYLAMMONIUM SALT (COMPOUND (I), $R_1=R_2=R_3=N-C_{13}H_{27}CO$, X=Y=O, N=M=Q=0, $R_4=R_5=R_7=R_9=H$, $R_6=OH$, P=1, $R_8=PO_3H_2$).

(1) To a solution of 2-(trimethylsilyl)ethyl 2-amino-2-deoxy-4,6-O-isopropylidene-β-D-glucopyranoside (6.46 g, 20.2 mmol) in $CHCl_3$ (300 mL) was added 1 N aqueous $NaHCO_3$ (300 mL) and 2,2,2-trichloroethyl chloroformate (8.5 g, 40 mmol). The resulting mixture was stirred vigorously for 3 h at room temperature. The organic layer was separated, dried ($Na_2SO_4$) and concentrated to give a colorless syrup. Flash chromatography on silica gel (gradient elution, 30→40% EtOAc-hexanes) afforded 9.6 g (96%) of 2-(trimethylsilyl)ethyl 2-deoxy-4,6-O-isopropylidine-2-(2,2,2-trichloroethoxycarbonylamino)-β-D-glucopyranoside as a colorless solid: mp 69–70° C.; $^1$H NMR ($CDCl_3$) δ 0.0 (s, 9H), 0.94 (m, 2H), 1.44 and 1.52 (2s, 6H), 2.94 (br s, 1H), 3.23–3.37 (m, 2H), 3.48–3.62 (m, 2H), 3.79 (t, 1H, J=10.5 Hz), 3.88–4.08 (m, 3H), 4.65 (d, 1H, J=8.3 Hz), 4.74 (m, 2H), 5.39 (d, 1H, J=7.4 Hz).

(2) A solution of the compound prepared in (1) above (7.5 g, 15.2 mmol), (R)-3-tetradecanoyloxytetradecanoic acid (7.58 g, 16.7 mmol) and 4-pyrrolidinopyridine (0.25 g, 1.7 mmol) in $CH_2Cl_2$ (95 mL) was treated with 1-(3-dimethylaminopropyl)-3-ethylcarbodiimide methiodide (EDC·MeI; 4.94 g, 16.7 mmol) and stirred for 16 h at room temperature. The reaction mixture was filtered through a short pad of Celite®, concentrated, and the resulting residue was heated at 60° C. in 90% aqueous AcOH (100 mL) for 1 h. The mixture was concentrated and residual AcOH and water were removed by azeotroping with toluene (2×150 mL). The crude diol was purified by flash chromatography on silica gel (gradient elution, 30→40% EtOAc-hexanes) to give 11.8 g (83%) of 2-(trimethylsilyl)ethyl 2-deoxy-3-O-[(R)-3-tetradecanoyloxytetradecanoyl]-2-(2,2,2-trichloroethoxycarbonylamino)-β-D-glucopyranoside as an amorphous solid: $^1$H NMR ($CDCl_3$) δ 0.0 (s, 9H), 0.9 (m, 8H), 1.1–1.7 (m, 42H), 2.30 (t, 2H, J=7.4 Hz), 2.52 (m, 2H), 3.36–3.72 (m, 4H), 3.78–4.03 (m, 3H), 4.57 (d, 1H, J=8.3 Hz), 4.65 (d, 1H, J=11 Hz), 4.77 (d, 1H, J=11 Hz), 5.0–5.15 (m, 2H), 5.20 (d, 1H, J=7.4 Hz).

(3) A solution of the compound prepared in (2) above (10.9 g, 12 mmol) and pyridine (2 mL, 25 mmol) in $CH_2Cl_2$ (125 mL) at 0° C. was treated dropwise over 15 min with a solution of 2,2,2-trichloro-1,1-dimethylethyl chloroformate (3.17 g, 13.2 mmol) in $CH_2Cl_2$ (25 mL). The reaction mixture was allowed to warm slowly to ambient temperature over 3.5 h. 4-Pyrrolidinopyridine (0.89 g, 6.0 mmol), N,N-diisopropylethylamine (10.5 mL, 60 mmol) and diphenyl chlorophosphate (3.7 mL, 18 mmol) were added sequentially and the resulting mixture was stirred for 5 h at room temperature. The reaction mixture was diluted with CH$_2$Cl$_2$ (500 mL), washed with cold 7.5% aqueous HCl (2×250 mL), water (250 mL), saturated aqueous NaHCO$_3$ (250 mL), dried (Na$_2$SO$_4$), and then concentrated. The residue obtained was purified by flash chromatography on silica gel eluting with 12.5% EtOAc-hexanes to give 15.1 g (95%) of 2-(trimethylsilyl)ethyl 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichlorethoxycarbonylamnino)-β-D-glucopyranoside as a viscous oil: $^1$H NMR (CDCl$_3$) δ 0.0 (s, 9H), 0.8–1.0 (m, 8H), 1.1–1.65 (m, 42H), 1.83 and 1.90 (2s, 6H), 2.15–2.45 (m, 4H), 3.34 (q, 1H, J=8 Hz), 3.37 (m, 1H), 3.81 (m, 1H), 3.95 (m, 1 H), 4.27 (dd, 1H, J=12, 5 Hz), 4.34 (d, 1H, J=12 Hz), 4.58 (d, 1H, J=12 Hz), 4.66 (q, 1H, J=9 Hz), 4.86 (d, 1H, J=12 Hz), 5.03 (d, 1H, J=7.9 Hz), 5.21 (m, 1H), 5.54–5.70 (m, 2H), 7.2–7.8 (mn, 10H).

(4) A solution of the compound prepared in (3) above (1.87 g, 1.41 mmol) in CH$_2$Cl$_2$ (3 mL) at 0° C. was treated dropwise over 10 min with trifluoroacetic acid (TFA; 6 mL) and then stirred for 4 h at 0° C. The reaction mixture was concentrated and residual TFA was removed by azeotroping with toluene (2×5 mL). A solution of the lactol and dimethylformamide (2.2 mL, 28.2 mmol) in CH$_2$Cl$_2$ (14 mL) at 0° C. was treated with oxalyl bromide (2.0 M in CH$_2$Cl$_2$; 2.1 mL, 4.2 mmol) dropwise over 15 min and the resulting suspension was stirred at 0° C. for 24 h. The reaction mixture was partitioned between cold saturated aqueous NaHCO$_3$ (25 mL) and ether (50 mL) and the layers were separated. The ethereal layer was washed with saturated aqueous NaCl, dried (Na$_2$SO$_4$) and concentrated to give 1.85 g (~100%) of 2-deoxy-4-O-diphenylphosphono-3-O-[(R)-3-tetradecanoyloxytetradecanoyl]-6-O-(2,2,2-trichloro-1,1-dimethylethoxycarbonyl-2-(2,2,2-trichloroethoxycarbonylamino)-α-D-glucopyranosyl bromide as a colorless glass.

(5) A solution of (R)-2-amino-3-benzyloxy-1-propanol (0.46 g, 2.33 mmol) and (R)-3-tetradecanoyloxytetradecanoic acid (1.29 g, 2.83 mmol) in CH$_2$Cl$_2$ (20 mL) was treated with EDC·MeI (0.78 g, 2.79 mmol) and stirred for 16 h at room temperature. The reaction mixture was filtered through a short pad of Celite® and concentrated. Flash chromatography on silica gel with 45% EtOAc-hexanes afforded 1.1 g (69%) of 3-benzyloxy-(R)-2-[(R)-3-tetradecanoyloxytetradecanoylamino]propanol as a colorless solid: mp 42–44.5° C.; $^1$H NMR δ 0.88 (t, 6H, J=6.5 Hz), 1.0–1.7 (m, 42 H), 2.50 (t, 2H, J=7.5 Hz), 2.46 (m, 2H), 3.56 (br s, 1H), 3.5–3.75 (m, 3H), 3.78 (dd, 1H, J=11, 4 Hz), 4.08 (m, 1H), 4.51 (s, 2H), 5.17 (m, 1H), 6.36 (d, 1H, J=7.8 Hz), 7.2–7.4 (m, 5H).

(6) To a solution of the compound prepared in (4) above (1.00 g, 0.776 mmol) and the compound prepared in (5) above (0.35 g, 0.57 mmol) in dichloroethane (4.5 mL) was added powdered 4 A molecular sieves (1.25 g) and calcium sulfate (2.7 g, 20 mmol). After stirring for 10 min at room temperature, the mixture was treated with mercury cyanide (1.0 g, 4.0 mmol) and then heated to reflux for 12 h shielded from light. The reaction mixture was diluted with CH$_2$Cl$_2$ (25 mL) and filtered through a pad of Celite®. The filtrate was washed with 1N aqueous KI (25 mL), dried (Na$_2$SO$_4$) and concentrated. The residue was chromatographed on silica gel with EtOAc-hexanes-MeOH (80:20:0→70:30:1, gradient elution) to give 0.66 g (63%) of 3-benzyloxy-(S)-2-[(R)-3-tetradecanoyloxytetradecanoylamino]propyl 2-deoxy-4-O-phosphono-3-O-[(R)-tetradecanoyloxytetradecanoyl]-6-O -(2,2,2-trichloro-1,1-dimethylethoxycarbonyl)-2-(2,2,2-trichloroethoxycarbonylamino)-β-D-glucopyranoside as an amorphous solid: $^1$H NMR δ 0.88 (t, 12H, J=6.5 Hz), 1.0–1.65 (m, 84H), 1.79 and 1.86 (2s, 6H), 2.1–2.5 (m, 8H), 3.35–3.55 (m, 3H), 3.65–3.8 (mn, 3H), 4.1–4.75 (m, 9H), 5.05–5.3 (m, 2H), 5.3–5.5 (m, 2H), 6.04 (d, 1H, J=8.4 Hz), 7.05–7.45 (m, 15H).

(7) A stirred solution of the compound prepared in (6) above (0.60 g, 0.328 mmol) in AcOH (9 mL) at 55° C. was treated with zinc dust (1.1 g, 16 mmol) in three equal portions over 1 h. The cooled reaction mixture was sonicated, filtered through a bed of Celite® and concentrated. The resulting residue was partitioned between CH$_2$Cl$_2$ (60 mL) and cold 1 N aqueous HCl (35 mL) and the layers separated. The organic layer was washed with 5% aqueous NaHCO$_3$, dried (Na$_2$SO$_4$) and concentrated. A mixture of the residue obtained and (R)-3-tetradecanoyloxytetradecanoic acid (0.18 g, 0.39 mmol) in CH$_2$Cl$_2$ (3.5 mL) was stirred with powdered 4 Å molecular sieves (0.1 g) for 30 min at room temperature and then treated with 2-ethoxy-1-ethoxycarbonyl-1,2-dihydroquinoline (EEDQ; 0.12 g, 0.49 mmol). The resulting mixture was stirred for 6 h at room temperature, filtered through Celite® and then concentrated. Chromatography on silica gel (gradient elution, 0.5→1% MeOH—CHCl$_3$) afforded 0.31 g (50%) of 3-benzyloxy-(S)-2-[(R)-3-tetradecanoyloxytetradecanoylamino]propyl 2-deoxy-4-O-diphenylphosphono-2-[(R)-3-tetradecanoyloxytetradecanoylamino]-3-O-[(R)-3-tetradecanoyloxytetradecanoyl]-β-D-glucopyranoside as an amorphous solid: $^1$H NMR (CDCl$_3$) δ 0.88 (t, 18H, J=~6.5 Hz), 1.0–1.8 (m, 126H), 2.1–2.5 (m, 12H), 3.35–3.75 (m, 6H), 3.80 (m, 2H), 4.23 (m, 1H), 4.46 (d, 1H, J=12 Hz), 4.51 (d, 1H, J=12 Hz), 4.65 (q, 1H, J=~9.5 Hz), 4.82 (d, 1H, J=8.1 Hz), 5.05–5.25 (m, 3H), 5.47 (t, 1H, J=~9.5 Hz), 6.16 (d, 1H, J=8.1 Hz), 6.31 (d, 1H, J=8.4 Hz), 7.1–7.4 (m, 15H).

(8) A solution of the compound prepared in (7) above (0.26 g, 0.138 mmol) in THF (25 mL) was hydrogenated in the presence of 5% palladium on carbon (50 mg) at room temperature and atmospheric pressure for 16 h. After removal of the catalyst by filtration, AcOH (3 mL) and platinum oxide (0.14 g) were added and the hydrogenation was continued at room temperature and 75 psig for 24 h. The resulting opalescent reaction mixture was diluted with 2:1 CHCl$_3$—MeOH (20 mL) and sonicated briefly to give a clear solution. The catalyst was collected, washed with 2:1 CHCl$_3$-MeOH (2×5 mL) and the combined filtrate and washings were concentrated. The residue was dissolved in 1% aqueous triethylamine (10 mL) by sonicating for 5 min at 35° C. and the resulting solution was lyophilized. Flash chromatography on silica gel with chloroform-methanol-water-triethylamine (94:6:0.5:0.5→88:12:1.0:1.0, gradient elution) afforded 0.20 g (84%) of product as a colorless powder. A portion of the chromatography product (0.166 g) was dissolved in cold 2:1 CHCl$_3$—MeOH (33 mL) and washed with cold 0.1 N aqueous HCl (14 mL). The lower organic layer was filtered and concentrated and the free acid obtained was lyophilized from 1% aqueous triethylamine (pyrogen free, 15 mL) to give 0.160 g of 3-hydroxy-(S)-2-[(R)-tetradecanoyloxytetradecanoylamino]propyl 2-deoxy-4-O-phosphono-2-[(R)-3-tetradecanoyloxytetradecanoylamino]-3-O-[(R)-3-tetradecanoyloxytetradecanoyl]-β-D-glucopyranoside triethylammonium salt as a colorless solid: mp 178–180° C. (dec); IR (film) 3293, 3103, 2959, 2924, 2855, 1732, 1654, 1640, 1553, 1467, 1377, 1259, 1175, 1106, 1086, 1050, 803, 720 cm$^{-1}$; HMR (CDCl$_3$—CD$_3$OD) δ 0.88 (t, 18H, J=~7 Hz), 1.0–1.7 (mn, 135H), 2.15–2.75 (m, 12H), 3.02 (q, 6H, J=7 Hz), 3.35–4.1 (m, 7H), 4.22 (q, 1H, J=~9.5 Hz), 4.77 (d, 1H, J=8 Hz), 5.05–5.35 (mn, 4H), 6.58 (d, 1H, J=6 Hz), 6.73 (d, 1H, J=7.5 Hz, NH); $^{13}$C NMR (CDCl$_3$) δ 173.5, 173.2, 170.7, 170.5, 170.0, 100.7, 75.9, 72.7, 71.2, 71.0, 70.8, 70.6, 67.9, 61.7, 60.5, 55.0, 50.4, 45.6, 41.4, 39.5, 34.5, 34.4, 32.0, 31.8, 30.3, 29.8, 29.4, 29.3, 25.3, 25.1, 22.7, 14.2, 8.6.

Anal. Calcd for $C_{19}H_{192}N_3O_{18}P.5H_2O$: C, 64.84;H, 11.10; N, 2.29; P, 1.69. Found: C, 64.69;H, 11.24; N, 1.93; P, 1.44.

EXAMPLE 3

B2

PREPARATION OF 3-HYDROXY-(R)-2-[(R)-3-TETRADECANOYLOXYTETRADECANOYLAMI-NO]PROPYL 2-DEOXY-4-O-PHOSPHONO-2-[(R)-3-TETRADECANOYLOXYTETRADECANOYLAMI-NO]-3-O-[(R)-3-TETRADECANOYLOXYTETRADECANOYL]-β-D-GLUCOPYRANOSIDE TRIETHYLAMMONIUM SALT (COMPOUND (I), $R_1$=$R_2$=$R_3$=N—$C_{13}H_{27}$CO, X=Y=O, N=M=Q=0, $R_4$=$R_5$=$R_7$=$R_9$=H, $R_6$=OH, P=1, $R_8$=$PO_3H_2$).

(1) A solution of the compound prepared in Example 2-(5) (0.63 g, 1.02 mmol) in CH$_2$Cl$_2$ (7 mL) was treated sequentially with pyridine (0.4 mL, 5 mmol), 4-dimethylaminopyridine (cat.) and 2,2,2-trichloro-1,1-dimethylethyl chloroformate (0.307 g, 1.23 mmol) and stirred for 16 h at room temperature. The reaction mixture was diluted with CH$_2$Cl$_2$ (25 mL), washed with saturated aqueous NaHCO$_3$ (25 mL) and dried (Na$_2$SO$_4$). Removal of volatiles in vacuo gave a residue which was dissolved in THF-AcOH (10 mL, 9:1) and hydrogenated in the presence of 5% palladium on carbon (150 mg) at room temperature and atmospheric pressure for 24 h. After removal of the catalyst by filtration and concentration of the filtrate, the residue was purified by flash chromatography on silica gel with 35% EtOAc-hexanes to give 0.536 g (72%) of 3-(2,2,2-trichloro-1,1-dimethylethoxycarbonyloxy)-(S)-2-[(R)-3-tetradecanoyloxytetradecanoylamino]propanol as an amorphous solid: $^1$H NMR (CDCl$_3$) δ 0.88 (t, 6H, J=~6.5 Hz), 1.1–1.7 (m, 42H), 1.94 (s, 6H), 2.30 (t, 2H, J=7.5 Hz), 2.47 (d, 2H, J=6 Hz), 3.50 (br s, 1H), 3.72 (m, 2H), 4.15–4.35 (m, 3H), 5.15 (m, 1H), 6.18 (d, 1H, J=7.2 Hz).

(2) In the same manner as described in Example 2-(6), the compound prepared in (1) above (0.310 g, 0.426 mmol) and the compound prepared in Example 2-(4) (0.961 g, 0.745 mmol) were coupled in the presence of mercury cyanide (0.43 g, 1.7 mmol) to give 0.644 g (78%) of 3-(2,2,2-trichloro-1,1-dimethylethyloxycarbonyloxy)-(S)-2-[(R)-3-tetradecanoyloxytetradecanoylamino]propyl 2-deoxy-4-O-phosphono-3-O-[(R)-tetradecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12H, J=~6.5 Hz), 1.0–1.7 (m, 84H), 1.81 and 1.89 (2s, 6 H), 1.93 (s, 6H), 2.15–2.55 (m, 8H), 3.45–3.7 (m, 2H), 3.80 (br d, 1H, J=9 Hz), 3.9–4.45 (m, 6H), 4.6–4.8 (m, 3H), 4.87 (d, 1H, J=8.1 Hz), 5.0–5.25 (m, 2H), 5.48 (t, 1H, J=~9.5 Hz), 6.1–6.3 (m, 2H).

(3) In the same manner as described in Example 2-(7), the compound prepared in (2) above (0.602 g, 0.310 mmol) was deprotected with zinc (1.5 g, 23 mmol) and acylated with (R)-3-tetradecanoyloxytetradecanoic acid, (0.17 g, 0.37 mmol) in the presence of EEDQ (0.115 g, 0.467 mmol) to give 0.365 g (66%) of 3-hydroxy-(R)-2-[(R)-3-tetradecanoyloxytetradecanoylamino]propyl 2-deoxy-4-O-diphenylphosphono-2-[(R)-3-tetradecanoyloxytetradecanoylamino]-3-O-[(R)-3-tetradecanoyloxytetradecanoyl]-β-D-glucopyranoside as an amorphous solid: $^1$H NMR (CDCl$_3$) δ 0.88 (t, 18H, J=~6.5 Hz), 1.0–1.7 (m, 126H), 2.15–2.55 (m, 12H), 3.18 (br s, 1H), 3.45–3.8 (m, 8H), 3.85–4.05 (m, 2H), 4.69 (q, 1H, J=9.5 Hz), 5.05–5.25 (m, 3H), 5.42 (t, 1H, J=~9.5 Hz), 6.42 (d, 1H, J=7.8 Hz), 6.59 (d, 1H, J=7.2 Hz), 7.1–7.4 (m, 10H).

(4) In the same manner as described in Example 2-(8), the compound prepared in (3) above (0.355 g, 0.196 mmol) was hydrogenated in the presence of platinum oxide (175 mg) to give 0.265 g (77%) of 3-hydroxy-(R)-2-[(R)-3-tetradecanoyloxytetradecanoylamino]propyl 2deoxy-4-O-phosphono-2-[(R)-3-tetradecanoyloxytetradecanoylamino]-3-O-[(R)-3-tetradecanoyloxytetradecanoyl]-β-D-glucopyranoside triethylammonium salt as a colorless solid: mp 159–160° C.; IR (film) 3291, 2956, 2922, 2853, 1738, 1732, 1716, 1650, 1643, 1556, 1468, 1171, 1109, 1083, 1051 cm$^{-1}$; $^1$H NMR (CDCl$_3$—CD$_3$OD) δ 0.88 (t, 18H, J=~6.5 Hz), 1.0–1.7 (m, 135H), 2.15–2.75 (m, 12H), 3.06 (q, 6H, J=7 Hz), 3.25–3.45 (m, 2H), 3.5–4.05 (m, 12H), 4.19 (q, 1H, J=~9.5 Hz), 4.48 (d, 1H, J=8.4 Hz), 5.04–5.26 (m, 4H), 7.18 (d, 1H, J=7.8 Hz), 7.27 (d, 1H, J=8.7 Hz); $^{13}$C NMR (CDCl$_3$) δ 173.5, 173.4, 170.7, 170.6, 170.1, 101.0, 76.0, 72.6, 71.4, 71.0, 70.8, 70.6, 68.7, 61.8, 60.5, 55.3, 50.5, 45.6, 41.5, 41.4, 39.5, 34.6, 34.4, 34.3, 32.0, 29.8, 29.4, 25.4, 25.1, 22.7, 14.1, 8.6.

Anal. Calcd for $C_{99}H_{192}N_3O_{18}P.H_2O$: C, 67.50;H, 11.10; N, 2.39; P, 1.76. Found: C, 67.40;H, 11.22; N, 2.34; P, 2.11.

EXAMPLE 4

B3

PREPARATION OF 3-HYDROXY-(S)-2-[(R)-3-DODECANOYLOXYTETRADECANOYLAMINO]-PROPYL 2-DEOXY-4-O-PHOSPHONO-2-[(R)-3-DODECANOYLOXYTETRADECANOYLAMINO]-3-O-[(R)-3-DODECANOYLOXYTETRADECANOYL]-β-D-GLUCOPYRANOSIDE TRIETHYLAMMONIUM SALT (COMPOUND (I), $R_1$=$R_2$=$R_3$=N—$C_{11}H_{23}$CO, X=Y=O, N=M=Q=0, $R_4$=$R_5$=$R_7$=$R_9$=H, $R_6$=OH, P=1, $R_8$=$PO_3H_2$).

(1) A solution of D-glucosaminide hydrochloride (20 g, 92.8 mmol) in H$_2$O (250 mL) was treated with a saturated aqueous NaHCO$_3$ (250 mL) and 2,2,2-trichloroethyl chloroformate (14.05 mL, 102 mmol) and stirred vigorously for 18 h. The white solid that formed was collected on a fritted funnel and dried under vacuum for 24 h. A solution of the solid in pyridine (100 mL) was cooled to 0° C. and treated with acetic anhydride (100 mL) via addition funnel. The solution was stirred for 18 h at room temperature, poured into 1 L of H$_2$O and extracted with CHCl$_3$ (3×500 mL). The solvent was removed in vacuo to afford 45 g (quant.) of N-(2,2,2-trichloroethoxycarbonylamino)-1,3,4,6-tetra-O-acetyl-2-deoxy-α-D-glucopyranoside which was used without further purification: $^1$H NMR (CDCl$_3$) δ 2.06 (s, 6H), 2.12 (s, 3H), 2.22 (s, 3H), 4.03 (m, 1H), 4.07 (d, 1H, J=12.4 Hz), 4.22 (dt, 1H, J=9.9, 3.6 Hz), 4.30 (dd, 1H, J=12.4, 4.0 Hz), 4.64 (d, 1H, J=9.6 Hz), 5.28 (dt, 1H, J=10.2, 9.9 Hz), 6.25 (d, 1H, J=3.6 Hz).

(2) A solution of (R)-2-amino-3-benzyloxy-1-propanol (5 g, 27.6 mmol) in CH$_2$Cl$_2$ (250 mL) was treated with allyl chloroformate (3.2 mL, 30 mmol) and saturated aqueous NaHCO$_3$ (250 mL) for 18 h. The organic layer was separated and concentrated in vacuo. Purification by chromatography eluting with 30% EtOAc/hexanes afforded 6.9 g (94%) of (R)-2-(allyloxycarbonylamino)-3-benzyloxy-1-propanol as an amorphous solid: $^1$H NMR (CDCl$_3$) δ 2.56 (br s, 1H), 3.69 (m, 3H), 3 88 (m, 2H), 4.54 (s, 2H), 4.58 (d, 2H, J=5.6 Hz), 5.23 (dd, 1H, J=10.4, 1.1 Hz), 5.33 (dd, 1H, J=17.1, 1.1 Hz), 5.42 (m, 1H), 5.93 (m, 1H), 7.35 (m, 5H).

(3) A solution of the compounds prepared in (1) and (2) above (8.9 g, 17 mmol and 3.6 g, 10 mmol, respectively) in $CH_2Cl_2$ was treated with boron trifluoride etherate (4.3 mL, 34 mmol) at room temperature for 16 h. The reaction mixture was quenched with saturated aq. $NaHCO_3$ (100 mL) and extracted with EtOAc (3×100 mL). The combined EtOAc extracts were dried ($Na_2SO_4$) and concentrated. The residue obtained was chromatographed with 20% EtOAc/hexanes to afford 6.03 g (83%) of 3-benzyloxy-(S)-2-(allyloxycarbonylamino)propyl 2-deoxy-3,4,6-tri-O-acetyl-2-(2,2,2-trichloroethoxycarbonylamino)-β-D-glucopyranoside as an amorphous solid: $^1H$ NMR ($CDCl_3$) δ 2.02 (s, 3H), 2.03 (s, 3H), 2.08 (s, 3H), 3.45 (m, 1H), 3.54 (m, 1H), 3.64 (m, 1H), 3.76 (d, 1H, J=7.2 Hz), 3.91 (m, 2H), 4.12 (d, 1H, J=12.2 Hz), 4.26 (dd, 1H, J=12.4, 4.7 Hz), 4.37 (d, 1H, J=8.2 Hz), 4.43 (d, 1H, J=12.1 Hz), 4.55 (m, 2H), 4.68 (m, 2H), 4.87 (d, 1H, J=8.0 Hz), 5.07 (m, 2H), 5.21 (d, 1H, J=9.7 Hz), 5.29 (d, 1H, J=17.3 Hz), 5.91 (m, 1H), 7.36 (m, 5H).

(4) A solution of the compound prepared in (3) above (6.0 g, 8.3 mmol) in methanol (83 mL) was treated with ammonium hydroxide (8.3 mL) at room temperature for 2 h. The solvent was removed in vacuo and replaced with 2,2-dimethoxypropane (50 mL) and camphorsulfonic acid (100 mg) was added. The reaction was stirred for 18 h, neutralized with solid $NaHCO_3$ (1 g), filtered and concentrated in vacuo. Purification by chromatography with 50% EtOAc/hexanes afforded 4.58 g (86%) of 3-benzyloxy-(S)-2-(allyloxycarbonylamino)propyl 2-deoxy-4,6-O-isopropylidine-2-(2,2,2-trichloroethoxycarbonylamino)-β-D-glucopyranoside: $^1H$ NMR ($CDCl_3$) δ 1.46 (s, 3H), 1.53 (s, 3H), 2.94 (m, 1H), 3.25 (m, 1H), 3.55 (m, 4 H), 3.83 (m, 3H), 3.93 (m, 3H), 4.52 (m, 5H), 4.68 (d, 1H, J=12.1 Hz), 4.77 (d, 1H, J=12.1 Hz), 5.07 (m, 1H), 5.26 (m, 2H), 5.92 (m, 1H), 7.37 (m, 5H).

(5) A solution of the compound prepared in (4) above (1.0 g, 1.56 mmol) in $CH_2Cl_2$ (20 mL) was treated with (R)-3-dodecanoyloxytetradecanoic acid (730 mg, 1.71 mmol) in the presence of EDC·MeI (560 mg, 1.87 mmol) and 4-pyrrolidinopyridine (50 mg). The reaction was stirred at room temperature for 18 h and filtered through a 6×8 cm plug of silica gel using 20% EtOAc/hexanes as eluent to afford 1.33 g (82%) of 3-benzyloxy-(S)-2-(allyloxycarbonylamino)propyl 2-deoxy-4,6-O-isopropylidene-3-O-[(R)-3-dodecanoyloxytetradecanoyl]-2-(2,2,2-trichloroethoxycarbonylamino)-β-D-glucopyranoside as an amorphous solid: $^1H$ NMR ($CDCl_3$) δ 0.88 (t, 6H, J=6.8 Hz), 1.1–1.6 (m, 38H), 1.37 (s, 3H), 1.46 (s, 3H), 2.28 (t, 2H, J=7.4 Hz), 2.49 (dd, 1H, J=15.1, 6.0 Hz), 2.61 (dd, 1H, J=15.1, 6.6 Hz), 3.25–4.0 (m, 9H), 4.38 (m, 2H), 4.54 (m, 2H), 4.65 (m, 2H), 4.97 (m, 2H), 5.25 (m, 5H), 5.88 (m, 1H), 7.34 (m, 5H).

(6) To a solution of the compound prepared in (5) above (1.31 g, 1.25 mmol) in THF (20 mL) was added dimethyl malonate (1.0 mL, 0.88 mmol) and the solution was degassed in a stream of argon for 30 min. Tetrakis (triphenylphosphine)palladium(0) (200 mg) was added and the reaction was stirred at room temperature for 2 h, and then concentrated in vacuo. The residue obtained was chromatographed on silica gel eluting with 5–10% EtOAc/$CHCl_3$. The free amine obtained was acylated with (R)-3-dodecanoyloxytetradecanoic acid (560 mg, 1.38 mmol) in the presence of EEDQ (370 mg, 1.5 mmol) in $CH_2Cl_2$ (15 mL). After stirring at room temperature for 18 h, the solvent was removed in vacuo and the resultant oil was chromatographed on silica gel eluting with 20%EtOAc/hexanes to afford 1.02 g (63%) of 3-benzyloxy-(S)-2-[(R)-3-dodecanoyloxytetradecanoylamino]propyl 2-deoxy-4,6-O-isopropylidene-3-O-[(R)-3-dodecanoyloxytetradecanoyl]-2-(2,2,2-trichloroethoxycarbonylamino)-β-D-glucopyranoside as a colorless amorphous solid: $^1H$ NMR ($CDCl_3$) δ 0.88 (t, 12H, J=6.9 Hz), 1.1–1.7 (m, 78H), 1.38 (s, 3H), 1.46 (s, 3H), 2.26 (m, 4H), 2.49 (dd, 1H, J=15.1, 6.0 Hz), 2.61 (dd, 1H, J=15.1, 6.6 Hz), 3.25–4.0 (m, 9H), 5.01 (m, 2H), 6.02 (d, 1H, J=8.4 Hz), 7.34 (m, 5H).

(7) The compound prepared in (6) above (1.0 g, 0.78 mmol) was treated with 90% aqueous AcOH (20 mL) for 1 h at 60° C. The solution was concentrated in vacuo and residual AcOH and $H_2O$ were removed by azeotroping with toluene (10 mL). The residue was dissolved in $CH_2Cl_2$, cooled to 0° C., and treated with pyridine (0.076 mL, 0.94 mmol) and a solution of 2,2,2-trichloro-1,1-dimethylethyl chloroformate (205 mg, 0.86 mmol) in $CH_2Cl_2$ (5 mL). The reaction mixture was then allowed to warm and stir at room temperature for 18 h. The resulting light yellow solution was treated with diphenyl chlorophosphate (0.24 mL, 1.17 mmol), triethylamine (0.22 mL, 1.56 mmol) and catalytic 4-pyrrolidinopyridine (50 mg), and then stirred an additional 24 h at room temperature. The reaction mixture was diluted with $Et_2O$ (100 mL) and washed with 10% aq. HCl (50 mL). The organic phase was separated, dried over $Na_2SO_4$ and concentrated in vacuo. Chromatography over silica gel using 10% EtOAc/hexanes afforded 1.13 g (85%) of 3-benzyloxy-(S)-2-[(R)-3-dodecanoyloxytetradecanoylamino]propyl 2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1H$ NMR ($CDCl_3$) δ 0.87 (t, 12H, J=6.9 Hz), 1.1–1.6 (m, 78H), 1.78 (s, 3H), 1.86 (s, 3H), 2.01 (m, 1H), 2.18 (m, 3H), 2.40 (m, 2H), 2.67 (m, 1H), 2.88 (d, 1H, J=6.6 Hz), 2.97 (d, 1H, J=6.9 Hz), 3.41 (m, 2H), 3.72 (m, 1H), 3.82 (m, 1H), 4.24 (m, 1H), 4.42 (d, 1H, J=11.8 Hz), 4.64 (m, 3H), 5.16 (m, 1H), 5.39 (m, 2H), 5.75 (d, 1H, J=4.3 Hz), 6.05 (d, 1H, J=8.4 Hz), 7.23 (m, 15H).

(8) In the same manner as described in Example 2-(7), the compound prepared in (7) above (1.1 g, 0.65 mmol) was deprotected with zinc (2.1 g, 32 mmol) and acylated with (R)-3-dodecanoyloxytetradecanoic acid (330 mg, 0.78 mmol) in the presence of EEDQ (230 mg, 0.94 mmol) to afford 399 mg (37%) of 3-benzyloxy-(S)-2-[(R)-3-dodecanoyloxytetradecanoylamino]propyl 2-deoxy-4-O-diphenylphosphono-2-[(R)-3-dodecanoyloxytetradecanoylamino]-3-O-[(R)-3-dodecanoyltetradecanoyl]-β-D-glucopyranoside as a colorless amorphous solid.

(9) In the same manner as described in Example 2-(8), the compound prepared in (8) above (399 mg, 0.24 mmol) was hydrogenated in the presence of palladium hydroxide (150 mg) on carbon in EtOH (10 mL) and platinum oxide (300 mg) in EtOH/AcOH (10:1) to afford 65 mg (16%) of 3-hydroxy-(S)-2-[(R)-3-dodecanoyloxytetradecanoylamino]propyl 2-deoxy-4-O-phosphono-2-[(R)-3-dodecanoyloxytetradecanoylamino]-3-O-[(R)-3-dodecanoyloxytetradecanoyl]-β-D-glucopyranoside triethylammonium salt as a white powder: mp 181–184° C. (dec): IR (film) 3306, 2956, 2922, 2852, 1732, 1644, 1549, 1467, 1377, 1164, 1106, 1051, 721 cm$^{-1}$; $^1$HNMR($CDCl_3$—$CD_3OD$) δ 0.88 (t, 18H, J=6.7 Hz), 1.1–1.7(m, 123H), 2.2– 2.7 (m, 12H), 3.06 (q, 6H, J=7.1

Hz), 3.3–4.0 (m, 13H), 4.23 (m, 1H), 4.44 (d, 1 H, J=7.7 Hz), 5.0–5.3 (m, 4H); $^{13}$C NMR (CDCl$_3$) δ 173.9, 173.5, 173.3, 170.8, 170.5, 170.1, 101.0, 75.5, 73.0, 71.1, 70.9, 70.6, 67.9, 61.6, 60.7, 54.4, 50.4, 45.8, 41.6, 41.4, 39.6, 34.6, 31.9, 29.7, 29.4, 29.3, 25.4, 25.1, 22.7, 14.2, 8.6.

Anal. Calcd. for $C_{93}H_{150}N_3O_{18}P\cdot H_2O$: C, 66.59;H, 10.94; N, 2.50; P, 1.85. Found: C, 66.79;H, 10.65; N, 2.36; P, 1.70.

EXAMPLE 5

B4

PREPARATION OF 3-HYDROXY-(S)-2-[(R)-3-UNDECANOYLOXYTETRADECANOYLAMINO]-PROPYL 2-DEOXY-4-O-PHOSPHONO-2-[(R)-3-UNDECANOYLOXYTETRADECANOYLAMINO]-3-O-[(R)-3-UNDECANOYLOXYTETRADECANOYL]-β-D-GLUCOPYRANOSIDE TRIETHYLAMMONIUM SALT (COMPOUND (I), $R_1=R_2=R_3=N-C_{10}H_{21}CO$, X=Y=O, N=M=Q=0, $R_4=R_5=R_7=R_9=H$, $R_6=OH$, P=1, $R_8=PO_3H_2$).

(1) In the same manner as described in Example 4-(5), the compound prepared in Example 4-(4) (1.0 g, 1.56 mmol) was acylated with (R)-3-undecanoyloxytetradecanoic acid (705 mg, 1.71 mmol) in the presence of EDC·MeI (560 mg, 1.87 mmol) and 4-pyrrolidinopyridine (50 mg) in CH$_2$Cl$_2$ (20 mL) to afford 1.23 g (77%) of 3-benzyloxy-(S)-2-(allyloxycarbonylamino)propyl 2-deoxy-4,6-O-isopropylidene-3-O-[(R)-3-undecanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6H, =6.9 Hz), 1.1–1.6 (m, 36H), 1.37 (s, 3H), 1.46 (s, 3H), 2.28 (m, 2H), 2.52 (dd, 1H, J=15.1, 6.0 Hz), 2.61 (dd, 1H, =15.5, 6.8 Hz), 3.25 (m, 1H), 3.35–4.0 (m, 9H), 4.31 (m, 2H), 4.54 (m, 2H), 4.64 (m, 2H), 5.02 (m, 2H), 5.18 (m, 2H), 5.25 (m, 1H), 5.86 (m, 1H), 7.34 (m, 5H). (2) In the same manner as described in Example 4-(6) the compound prepared in (1) above (1.21 g, 1.17 mmol) was deprotected in THF (20 mL) in the presence of dimethyl malonate (1.0 mL, 0.88 mmol) and tetrakis(triphenylphosphine)palladium (0) (200 mg) and then acylated with (R)-3-undecanoyloxytetradecanoic acid (540 mg, 1.30 mmol) in the presence of EEDQ (370 mg, 1.5 mmol) to afford 921 mg (61%) of 3-benzyloxy-(S)-2-[(R)-3-undecanoyloxytetradecanoylamino]propyl 2-deoxy4,6-O-isopropylidene-3-O-[(R)-3-undecanoyloxytetradecanoyl]-2-(2,2,2-trichloroethoxycarbonylamino)-β-D-glucopyranoside as a colorless amorphous solid: $^1$H NMR (CDCl$_3$) δ 0.88 (t, 12H, J=6.6 Hz), 1.1–1.7 (m, 72H), 1.38 (s, 3H), 1.46 (s, 3H), 2.26 (m, 3H), 2.38 (m, 5H), 2.49 (dd, 1H, J=15.2, 6.0 Hz), 2.61 (dd, 1H, J=15.0, 6.5 Hz), 3.25–4.0 (m, 9H), 4.30 (m, 2H), 4.59 (m, 3H), 6.03 (d, 1H, J=8.2 Hz), 7.34 (m, 5H).

(3) In the same manner as described in Example 4-(7) the compound prepared in (2) above (910 g, 0.71 mmol) was deprotected in 90% aqueous AcOH (20 mL), and then treated with pyridine (0.071 mL, 0.88 mmol) and 2,2,2-trichloro-1,1-dimethylethyl chlorofonnate (195 mg, 0.80 mmol) in CH$_2$Cl$_2$ followed by diphenyl chlorophosphate (0.23 mL, 1.10 mmol), triethylamine (0.20 mL, 1.46 mmol) and catalytic 4-pyrrolidinopyridine (50 mg) to afford 1.10 g (89%) of 3-benzyloxy-(S)-2-[(R)-3-undecanoyloxytetradecanoylamino]propyl 2-deoxy-4-O-diphenylphosphono-3-O-[(R)-3-undecanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: H NMR (CDCl$_3$) δ 0.87 (t, 12H, J=6.7 Hz), 1.1–1.6 (m, 72H), 1.78 (s, 3H), 1.86 (s, 3H), 2.01 (m, 1H), 2.18 (m, 3H), 2.40 (m, 2H), 2.67 (m, 1H), 2.88 (d, 1H, J=6.7 Hz), 2.97 (d, 1H, J=6.9 Hz), 3.41 (m, 2H), 3.72 (m, 1H), 3.82 (m, 1H), 4.24 (m, 1H), 4.42 (d, 1H, J=11.8 Hz), 4.64 (m, 3H), 5.16 (m, 1 H), 5.39 (m, 2H), 5.75 (d, 1H, J=4.6 Hz), 6.05 (d, 1H, J=8.4 Hz), 7.22 (m, 15H).

(4) In the same manner as described in Example 2-(7), the compound prepared in (3) above (1.0 g, 0.59 mmol) was deprotected with zinc (2.0 g, 30 mmol) and acylated with (R)-3-undecanoyloxytetradecanoic acid (292 mg, 0.71 mmol) in the presence of EEDQ (210 mg, 0.85 mmol) to afford 388 mg (40%) of 3-benzyloxy-(S)-2-[(R)-3-undecanoyloxytetradecanoylamino]propyl 2-deoxy-4-O-diphenylphosphono-2-[(R)-3-undecanoyloxytetradecanoylamino]-3-O-[(R)-3-undecanoyltetradecanoyl]-β-D-glucopyranoside as a colorless amorphous solid.

(5) In the same manner as described in Example 2-(8), the compound prepared in (4) above (388 mg, 0.24 mmol) was hydrogenated in the presence of palladium hydroxide (150 mg) on carbon in EtOH (10 mL) and platinum oxide (300 mg) in EtOH/AcOH (10:1) to afford 65 mg (17%) of 3-hydroxy-(S)-2-[(R)-3-undecanoyloxytetradecanoylamino]propyl 2-deoxy-4-O-phosphono-2-[(R)-3-undecanoyloxytetradecanoylamino]-3-O-[(R)-3-undecanoyloxytetradecanoyl]-β-D-glucopyranoside tnrethylamnonium salt as a white powder: mp 183–184° C; IR (film) 3306, 2956, 2922, 2852, 1732, 1644, 1550, 1467, 1377, 1164, 1106, 1052, 721 cm$^{-1}$; $^1$H NMR (CDCl$_3$—CD$_3$OD) δ 0.88 (t, 18H, J=6.8 Hz), 1.1–1.7 (m, 117H), 2.2–2.7 (m, 12H), 3.07 (q, 6H, J=7.1 Hz), 3.3–3.9 (m, 13H), 4.23 (m, 1H), 4.45 (d, 1H, J=8.2 Hz), 5.0–5.3 (m, 4H); $^{13}$C NMR (CDCl$_3$) δ 173.8, 173.5, 173.3, 170.8, 170.5, 170.1, 101.0, 75.5, 73.1, 71.5, 71.3, 70.9, 70.6, 67.8, 61.6, 60.7, 54.4, 50.5, 45.8, 41.5, 41.4, 39.5, 34.6, 34.4, 32.0, 31.2, 29.8, 29.7, 29.4, 28.6, 26.1, 25.4, 25.1, 22.7, 14.1, 8.6.

Anal. Calcd. for $C_{90}H_{174}N_3O_{18}P\cdot H_2O$: C, 66.10;H, 10.85; N, 2.57; P, 1.89. Found: C, 66.34;H, 10.69; N, 2.32; P, 1.99.

EXAMPLE 6

B5

PREPARATION OF 3-HYDROXY-(S)-2-[(R)-3-DECANOYLOXYTETRADECANOYLAMINO] PROPYL 2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSIDE TRIETHYLAMMONIUM SALT (COMPOUND (I), $R_1=R_2=R_3=N-C_9H_{19}CO$, X=Y=O, N=M=Q=0, $R_4=R_5=R_7=R_9=H$, $R_6=OH$, P=1 $R_8=PO_3H_2$).

(1) In the same manner as described in Example 4-(5), the compound prepared in Example 4-(4) (2.0 g, 3.12 mmol) was acylated with (R)-3-decanoyloxytetradecanoic acid (1.36 g, 3.42 mmol) in the presence of EDC·MeI (1.12 g, 3.74 mmol) and 4-pyrrolidinopyridine (100 mg) in CH$_2$Cl$_2$ (40 mL) to afford 2.49 g (79%) of 3-benzyloxy-(S)-2-(allyloxycarbonylamino)propyl 2-deoxy-4,6-O-isopropylidene-3-O-[(R)-3-decanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6H, J=6.7 Hz), 1.1–1.6 (m, 34H), 1.36 (s, 3H), 1.46 (s, 3H), 2.27 (t, 2H, J=6.9 Hz), 248 (dd, 1H, J=15.1, 6.0 Hz), 2.60 (dd, 1H, J=15.1, 6.7 Hz), 3.25 (m, 1H), 3.35–4.0 (m, 9H), 4.23 (m, 1H), 4.42 (m, 1H), 4.52 (m, 4H), 4.95 (m, 2H), 5.17 (m, 3H), 5.88 (m, 1H), 7.36 (m, 5H).

(2) In the same manner as described in Example 4-(6) the compound prepared in (1) above (2.47 g, 2.42 mmol) was deprotected in TM (40 mL) in the presence of dimethyl malonate (2.0 mL, 1.75 mmol) and tetrakis (triphenylphosphine)palladium(0) (400 mg) and then acylated with (R)-3-decanoyloxytetradecanoic acid (1.06 g, 2.66 mmol) in the presence of EEDQ (740 mg, 3 mmol) to afford 1.86 g (60%) of 3-benzyloxy-(S)-2-[(R)-3-decanoyloxytetradecanoylamino]propyl 2-deoxy-4,6-O-isopropylidene-3-O-[(R)-3-decanoyloxytetradecanoyl]-2-(2,2,2-trichloroethoxycarbonylamino)-β-D-glucopyranoside as a colorless amorphous solid: $^1$H NMR (CDCl$_3$) δ 0.87 (t, 12H, J=6.7 Hz), 1.1–1.7 (m, 68H), 1.37 (s, 3H), 1.46 (s, 3H), 2.32 (m, 4H), 2.50 (dd, 1H, J=15.1, 6.0 Hz), 2.62 (dd, 1H, J=15.1, 6.8 Hz), 3.29 (m, 2H), 3.44 (m, 1H), 3.55 (m, 1H), 3.74 (m, 3H), 3.93 (m, 1H), 4.18 (m, 1H), 4.34 (m, 1H), 4.57 (d, 1H, J=11.8 Hz), 4.65 (m, 2H), 5.01 (m, 2H), 6.04 (d, 1H, J=8.3 Hz), 7.36 (m, 5H).

(3) In the same manner as described in Example 4-(7) the compound prepared in (2) above (900 mg, 0.72 mmol) was deprotected in 90% aqueous AcOH (40 mL), and then treated with pyridine (0.071 mL, 0.88 mmol) and 2,2,2-trichloro-1,1-dimethylethyl chloroformnate (195 mg, 0.80 mmol) in CH$_2$Cl$_2$ followed by diphenyl chlorophosphate (0.23 mL, 1.10 mmol), triethylamine (0.20 mL, 1.46 mmol) and catalytic 4-pyrrolidinopyridine (50 mg) to afford 1.05 g (86%) of 3-benzyloxy-(S)-2-[(R)-3-decanoyloxytetradecanoylamino]propyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.87 (t, 12H, J=6.3 Hz), 1.1–1.6 (m, 68H), 1.78 (s, 3H), 1.86 (s, 3H), 2.01 (m, 1H), 2.18 (m, 3H), 2.40 (m, 2H), 2.67 (m, 1H), 2.88 (d, 1H, J=6.5 Hz), 2.97 (d, 1H, J=6.9 Hz), 3.41 (m, 2H), 3.72 (m, 1H), 3.82 (m, 1H), 4.24 (m, 1H), 4.42 (d, 1H, J=11.8 Hz), 4.64 (m, 3H), 5.16 (m, 1H), 5.39 (m, 2H), 5.75 (d, 1H, J=4.3 Hz), 6.05 (d, 1H, J=8.4 Hz), 7.22 (m, 15H).

(4) In the same manner as described in Example 2-(7), the compound prepared in (3) above (1.0 g, 0.60 mmol) was deprotected with zinc (2.0 g, 30 mmol) and acylated with (R)-3-decanoyloxytetradecanoic acid (285 mg, 0.72 mmol) in the presence of EEDQ (210 mg, 0.86 mmol) to afford 332 mg (34%) of 3-benzyloxy-(S)-2-[(R)-3-decanoyloxytetradecanoylamino]propyl 2-deoxy-4-O-diphenylphosphono-2-[(R)-3-decanoyloxytetradecanoylamino]-3-O-[(R)-3-decanoyltetradecanoyl]-β-D-glucopyranoside as a colorless amorphous solid.

(5) In the same manner as described in Example 2-(8), the compound prepared in (4) above (332 mg, 0.20 mmol) was hydrogenated in the presence of palladium hydroxide (150 mg) on carbon in EtOH (10 mL) and platinum oxide (300 mg) in EtOH/AcOH (10:1) to afford 173 mg (55%) of 3-hydroxy-(S)-2-[(R)-3-decanoyloxytetradecanoylamino] propyl 2-deoxy-4-O-phosphono-2-[(R)-3-decanoyloxytetradecanoylamino]-3-O-[(R)-3-decanoyloxytetradecanoyl]-β-D-glucopyranoside triethylammonium salt as a white powder: mp 179–181° C.; IR (film) 3295, 2956, 2923, 2853, 1732, 1650, 1555, 1467, 1377, 1320, 1169, 1134, 1104, 1051, 979, 801, 721 cm$^{-1}$; $^1$H NMR (CDCl$_3$—CD$_3$OD) δ 0.88 (t, 18H, J=6.9 Hz), 1.1–1.7 (m, 111H), 2.2–2.7 (m, 12H), 3.07 (q, 6H, J=6.5 Hz), 3.3–4.3 (m, 14H), 4.45 (d, 1 H, J=8.0 Hz), 5.0–5.3 (m, 4H), 7.39 (m, 1H), 7.53 (d, 1H, J=9.1 Hz); $^{13}$C NMR (CDCl$_3$) δ 173.7, 173.4, 173.2, 170.7, 170.5, 170.1, 101.0, 75.4, 73.1, 71.6, 71.1, 70.8, 70.5, 67.8, 61.4, 60.8, 54.3, 50.4, 45.8, 41.3, 39.5, 34.5, 31.9, 29.8, 29.7, 29.4, 25.4, 25.1, 22.7, 14.1, 8.6.

Anal. Calcd. for C$_{87}$H$_{168}$N$_3$O$_{18}$P.H$_2$O: C, 65.58;H, 10.75; N, 2.64; P, 1.94. Found: C, 65.49;H, 10.75; N, 2.64; P, 1.97.

EXAMPLE 7

B6

PREPARATION OF 3-HYDROXY-(S)-2-[(R)-3-DECANOYLOXYTETRADECANOYLAMINO] PROPYL 2-DEOXY-6-O-PHOSPHONO-2-[(R)-3-DECANOYLOXYTETRADECANOYLAMINO]-3-O-[(R)-3-DECANOYLOXYTETRADECANOYL]-β-D-Glucopyranoside Triethylammonium Salt (Compound Of R$_1$=R$_2$=R$_3$=N—C$_9$H$_{19}$CO, X=Y=O, N=M=Q=0, R$_4$=R$_5$=R$_7$=R$_8$=H, R$_6$=OH, P=1, R$_9$=PO$_3$H$_2$).

(1) In the same manner as described in Example 4-(7) the compound prepared in Example 6-(2) (900 mg, 0.72 mmol) was deprotected in 90% aqueous AcOH (20 mL). The residue was dissolved in CH$_2$Cl$_2$ (20 mL), cooled to 0° C., and treated with triethylamine (0.14 mL, 1.0 mmol) and diphenyl chlorophosphate (0.17 mL, 0.8 mmol). The mixture was stirred for an additional 6 h, and then quenched with 50 mL of 10% HCl. The product was extracted with EtOAc (3×50 mL) and dried over Na$_2$SO$_4$. Chromatography on silica gel with 50% EtOAc/hexanes afforded 636 mg (63%) of 3-benzyloxy-(S)-2-[(R)-3-decanoyloxytetradecanoylamino]propyl 2-deoxy-6-O-diphenylphosphono-3-O-[(R)-3-decanoyloxytetradecanoyl]-2-(2,2,2-trichloroethoxycarbonylamino)-β-D-glucopyranoside as a colorless amorphous solid: $^1$H NMR (CDCl$_3$) δ 0.87 (t, 12H, J=6.0 Hz), 1.1–1.6 (m, 68H), 1.79 (s, 3H), 1.86 (s, 3H), 2.01 (m, 1H), 2.18 (m, 3H), 2.40 (m, 2H), 2.67 (m, 1H), 2.89 (d, 1H, J=6.5 Hz), 2.97 (d, 1H, J=6.9 Hz), 3.41 (m, 2H), 3.75 (m, 1H), 3.82 (m, 1H), 4.24 (m, 1H), 4.42 (d, 1H, J=11.8 Hz), 4.65 (m, 3H), 5.16 (m, 1H), 5.39 (m, 2H), 5.75 (d, 1H, J=4.3 Hz), 6.05 (d, 1H, J=8.4 Hz), 7.22 (m, 15H).

(2) In the same manner as described in Example 2-(7), the compound prepared in (1) above (620 g, 0.44 mmol) was deprotected with zinc (722 mg, 11 mmol) and acylated with (R)-3-decanoyloxytetradecanoic acid (190 mg, 0.48 mmol) in the presence of EEDQ (170 mg, 0.58 mmol) to afford 254 mg (36%) of 3-benzyloxy-(S)-2-[(R)-3-decanoyloxytetradecanoylamino]propyl 2-deoxy-6-O-diphenylphosphono-2-[(R)-3-decanoyloxytetradecanoylamino]-3-O-[(R)-3-decanoyltetradecanoyl]-β-D-glucopyranoside as a colorless amorphous solid.

(3) In the same manner as described in Example 2-(8), the compound prepared in (2) above (254 mg, 0.16 mmol) was hydrogenated in the presence of palladium hydroxide (150 mg) on carbon in EtOH (10 mL) and platinum oxide (300 mg) in EtOH/AcOH (10:1) to afford 34 mg (13%) of 3-hydroxy-(S)-2-[(R)-3-decanoyloxytetradecanoylamino] propyl 2-deoxy-6-O-phosphono-2-[(R)-3-decanoyloxytetradecanoylamino]-3-O-[(R)-3-decanoyloxytetradecanoyl]-β-D-glucopyranoside triethylammonium salt as a white powder: mp 169–171° C; IR (film) 3306, 2922, 2853, 1732, 1644, 1548, 1467, 1377, 1316, 1165, 1106, 1053, 856, 722 cm$^{-1}$; $^1$H NMR (CDCl$_3$—CD$_3$OD) δ 0.88 (t, 18H, J=6.7 Hz), 1.1–1.7 (m, 111H), 2.2–2.7 (m, 12H), 3.05 (m, 6H), 3.3–3.95 (m, 12H), 4.11 (m, 1H), 4.34 (m, 1H), 4.89 (m, 1H), 5.0–5.3 (m, 4H). $^{13}$C NMR (CDCl$_3$) δ 173.8, 173.4, 171.1, 170.5, 101.3, 75.3, 74.9, 71.2, 71.0, 70.6, 68.8, 67.3, 65.1, 61.4, 53.4, 50.7, 45.9, 41.5, 41.3, 39.6, 34.6, 32.0, 29.8, 29.6, 29.4, 25.3, 25.1, 22.7, 14.1, 8.7.

Anal. Calcd. for C$_{87}$H$_{168}$N$_3$O$_{18}$P.H$_2$O: C, 65.58;H, 10.75; N, 2.64; P, 1.94. Found: C, 65.60;H, 10.34; N, 2.36; P, 2.01.

EXAMPLE 8

B17

PREPARATION OF 3-HYDROXY-(S)-2-[(R)-3-NONANOYLOXYTETRADECANOYLAMINO] PROPYL 2-DEOXY-4-O-PHOSPHONO-2-[(R)-3-NONANOYLOXYTETRADECANOYLAMINO]-3-O-[(R)-3-NONANOYLOXYTETRADECANOYL]-β-D-GLUCOPYRANOSIDE TRIETYLAMMONIUM SALT (COMPOUND (I), R$_1$=R$_2$=R$_3$=N—C$_8$H$_{17}$CO, X=Y=O, N=M=Q=O, R$_4$=R$_5$=R$_7$=R$_9$=H, R$_6$=OH, P=1, R$_8$=PO$_3$H$_2$).

(1) In the same manner as described in Example 4-(5), the compound prepared in Example 4-(4) (1.0 g, 1.56 mmol) was acylated with (R)-3-nonanoyloxytetradecanoic acid (660 mg, 1.71 mmol) in the presence of EDC·(560 mg, 1.87 mmol) and 4-pyrrolidinopyridine (50 mg) in CH$_2$Cl$_2$ (20 mL) to afford 1.31 g (83%) of 3-benzyloxy-(S)-2-(allyloxycarbonylamino)propyl 2-deoxy-4,6-O-isopropylidene 3-O-[(R)-3-nonanoyloxytetradecanoyl]-2-(2,2,2-trichloroethoxycarbonylamino)-β-D-glucopyranoside as an amorphous solid: $^1$H NMR (CDCl$_3$) δ 0.87 (t, 6H, J=6.8 Hz), 1.1–1.6 (m, 32H), 1.37 (s, 3H), 1.46 (s, 3H), 2.27 (t, 2H, J=7.4 Hz), 2.50 (dd, 1H, J=15.1, 6.0 Hz), 2.63 (dd, 1H, J=15.1, 6.8 Hz), 3.26 (m, 1H), 3.35–4.0 (m, 9H), 4.32 (d, 1H, J=7.8 Hz), 4.41 (d, 1H, J=12.0 Hz), 4.51 (m, 4H), 4.95 (m, 2H), 5.18 (m, 2H), 5.29 (d, 1H, J=17.2 Hz), 5.88 (m, 1H), 7.36 (m, 5H).

(2) In the same manner as described in Example 4-(6) the compound prepared in (1) above (1.29 g, 1.28 mmol) was deprotected in THF (20 mL) in the presence of dimethyl malonate (1.0 mL, 0.88 mmol) and tetrakis(triphenylphosphine)palladium(0) (200 mg) and then acylated with (R)-3-nonanoyloxytetradecanoic acid (540 mg, 1.41 mmol) in the presence of EEDQ (370 mg, 1.5 mmol) to afford 1.02 g (65%) of 3-benzyloxy-(S)-2-[(R)-3-nonanoyloxytetradecanoylamino]propyl 2-deoxy-4,6-O-isopropylidene-3-O-[(R)-3-nonanoyloxytetradecanoyl]-2-(2,2,2-trichloroethoxycarbonylamino)-β-D-glucopyranoside as a colorless amorphous solid: $^1$H NMR (CDCl$_3$) δ 0.87 (t, 12H, J=6.1 Hz), 1.1–1.7 (m, 64H), 1.37 (s, 3H), 1.46 (s, 3H), 2.28 (m, 4H), 2.50 (dd, 1H, J=15.5, 6.0 Hz), 2.62 (dd, 1H, J=14.8, 6.3 Hz), 3.27 (m, 2H), 3.44 (m, 1H), 3.55 (m, 1H), 3.74 (m, 3H), 3.93 (m, 1H), 4.18 (m, 1H), 4.34 (m, 2H), 4.57 (d, 1H, J=11.8 Hz), 4.65 (m, 2H), 4.97 (t, 1H, J=9.6 Hz), 5.06 (d, 1H, J=8.6 Hz), 5.15 (m, 2H), 6.05 (d, 1H, J=8.2 Hz), 7.35 (m, 5H).

(3) In the same manner as described in Example 4-(7) the compound prepared in (2) above (1.0 g, 0.81 mmol) was deprotected in 90% aqueous AcOH (20 mL), treated with pyridine (0.080 mL, 0.98 mmol) and 2,2,2-trichloro-1,1-dimethylethyl chloroformate (215 mg, 0.89 mmol) in CH$_2$Cl$_2$ followed by diphenyl chlorophosphate (0.25 mL, 1.22 mmol), triethylamine (0.21 mL, 1.52 mmol) and catalytic 4-pyrrolidinopyridine (50 mg) to afford 1.17 g (87%) of 3-benzyloxy-(S)-2-[(R)-3-nonanoyloxytetradecanoylamino]propyl 2-deoxy-4-O-diphenylphosphono-3-O-[(R)-3-nonanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.87 (t, 12H, J=6.1 Hz), 1.1–1.6 (m, 64H), 1.78 (s, 3H), 1.86 (s, 3H), 2.01 (m, 1H), 2.18 (m, 3H), 2.40 (m, 2H), 2.67 (m, 1H), 2.88 (d, 1H, J=6.5 Hz), 2.97 (d, 1H, J=6.9 Hz), 3.41 (m, 2H), 3.72 (m, 1H), 3.82 (m, 1H), 4.24 (m, 1H), 4.42 (d, 1H, J=11.8 Hz), 4.64 (m, 3H), 5.16 (m, 1H), 5.39 (m, 2H), 5.75 (d, 1H, J=4.3 Hz), 6.05 (d, 1H, J=8.4 Hz), 7.22 (m, 15H).

(4) In the same manner as described in Example 2-(7), the compound prepared in (3) above (1.1 g, 0.66 mmol) was deprotected with zinc (2.2 g, 33 mmol) and acylated with (R)-3-nonanoyloxytetradecanoic acid (305 mg, 0.79 mmol) in the presence of EEDQ (235 mg, 0.95 mmol) to afford 373 mg (35%) of 3-benzyloxy-(S)-2-[(R)-3-nonanoyloxytetradecanoylamino]propyl 2-deoxy-4-O-diphenylphosphono-2-[(R)-3-nonanoyloxytetradecanoyl]-3-O-[(R)-3-nonanoyltetradecanoyl]-β-D-glucopyranoside as a colorless amorphous solid.

(5) In the same manner as described in Example 2-(8), the compound prepared in (4) above (373 mg, 0.23 mmol) was hydrogenated in the presence of palladium hydroxide (150 mg) on carbon in EtOH (10 mL) and platinum oxide (300 mg) in EtOH/AcOH (10:1) to afford 43 mg (12%) of 3-hydroxy-(S)-2-[(R)-3-nonanoyloxytetradecanoylamino]propyl 2-deoxy-4-O-phosphono-2-[(R)-3-nonanoyloxytetradecanoylamino]-3-O-[(R)-3-nonanoyloxytetradecanoyl]-β-D-glucopyranoside triethylammonium salt as a white powder: mp 176–179° C.; IR (film) 3298, 2956, 2923, 2853, 1733, 1646, 1551, 1467, 1337, 1316, 1254, 1166, 1106, 1053, 722 cm$^{-1}$; $^1$H NMR (CDCl$_3$—CD$_3$OD) δ 0.87 (t, 18H, J=6.7 Hz), 1.1–1.7 (m, 105H), 2.2–2.7 (m, 12H), 3.03 (q, 6H, J=7.0 Hz), 3.3–4.3 (m, 14H), 4.43 (d, 1H, J=7.1 Hz), 5.0–5.3 (m, 4H), 7.12 (d, 1H, J=7.7 Hz), 7.17 (d, 1H, J=8.2 Hz); $^{13}$C NMR (CDCl$_3$) δ 173.9, 173.5, 173.3, 170.8, 170.5, 170.1, 100.9, 75.5, 73.1, 71.4, 71.1, 70.9, 70.6, 67.8, 61.6, 60.7, 54.3, 50.5, 45.8, 41.6, 41.4, 39.5, 34.6, 34.4, 32.0, 31.9, 29.8, 29.4, 29.3, 25.4, 25.1, 22.7, 14.1, 8.6.

Anal. Calcd. for C$_{88}$H$_{164}$N$_3$O$_{18}$P: C, 65.81;H, 10.65; N, 2.74; P, 2.02. Found: C, 66.14;H, 10.46; N, 2.58; P, 1.84.

EXAMPLE 9

B8

PREPARATION OF 3-HYDROXY-(S)-2-[(R)-3-HEPTANOYLOXYTETRADECANOYLAMINO] PROPYL 2-DEOXY-4-O-PHOSPHONO-2-[(R)-3-HEPTANOYLOXYTETRADECAMINO]-3-O-[(R)-3-HEPTANOYLOXYTETRADECANOYL]-β-D-GLUCOPYRANOSIDE TRIETHYLAMMONIUM SALT (COMPOUND (I), R$_1$=R$_2$=R$_3$=N—C$_6$H$_{13}$CO, X=Y=O, N=M=Q=0, R$_4$=R$_5$=R$_7$=R$_9$=H, R$_6$=OH, P=1, R$_8$=PO$_3$H$_2$).

(1) In the same manner as described in Example 4-(5), the compound prepared in Example 4-(4) (1.0 g, 1.56 mmol) was acylated with (R)-3-heptanoyloxytetradecanoic acid (610 mg, 1.71 mmol) in the presence of EDC·MeI (560 mg, 1.87 mmol) and 4-pyrrolidinopyridine (50 mg) in CH$_2$Cl$_2$ (20 mL) to afford 1.24 g (82%) of 3-benzyloxy-(S)-2-(allyloxycarbonylamino)propyl 2-deoxy-4,6-O-isopropylidene-3-O-[(R)-3-heptanoyloxytetradecanoyl]-2-(2,2,2-trichloroethoxycarbonylamino)-β-D-glucopyranoside as an amorphous solid: $^1$H NMR (CDCl$_3$)

δ 0.88 (t, 6H, J=6.0 Hz), 1.1–1.6 (m, 28H), 1.38 (s, 3H), 1.47 (s, 3H), 2.29 (t, 2H, J=7.4 Hz), 2.51 (dd, 1H, J=15.1, 6.0 Hz), 2.63 (dd, 1H, J=15.1, 6.8 Hz), 3.26 (m, 1H), 3.35–4.0 (m, 9H), 4.32 (d, 1H, J=7.3 Hz), 4.41 (d, 1H, J=12.0 Hz), 4.51 (m, 4H), 4.95 (m, 2H), 5.18 (m, 2H), 5.29 (d, 1H, J=17.3 Hz), 5.88 (m, 1H), 7.36 (m, 5H).

(2) In the same manner as described in Example 4-(6) the compound prepared in (1) above (1.22 g, 1.25 mmol) was deprotected in TBF (20 mL) in the presence of dimethyl malonate (1.0 mL, 0.88 mmol) and tetrakis (triphenylphosphine)palladium(0) (200 mg) and then acylated with (R)-3-heptanoyloxytetradecanoic acid (490 mg, 1.38 mmol) in the presence of EEDQ (370 mg, 1.5 mmol) to afford 925 mg (62%) of 3-benzyloxy-(S)-2-[(R)-3-heptanoyloxytetradecanoylamino]propyl 2-deoxy4,6-O-isopropylidene-3-O-[(R)-3-heptanoyloxytetradecanoyl]-2-(2,2,2-trichloroethoxycarbonylamino)-β-D-glucopyranoside as a colorless amorphous solid: $^1$H NMR (CDCl$_3$) δ 0.87 (t, 12H, J=6.7 Hz), 1.1–1.7 (m, 56H), 1.37 (s, 3H), 1.46 (s, 3H), 2.32 (m, 4H), 2.50 (dd, 1H, J=15.1, 6.0 Hz), 2.62 (dd, 1H, J=15.1, 6.8 Hz), 3.29 (m, 2H), 3.44 (m, 1H), 3.55 (m, 1H), 3.74 (m, 3H), 3.93 (m, 1H), 4.18 (m, 1H), 4.34 (m, 1H), 4.57 (d, 1H, J=11.8 Hz), 4.65 (m, 2H), 5.01 (m, 2H), 6.04 (d, 1H, J=8.3 Hz), 7.36 (m, 5H).

(3) In the same manner as described in Example 4-(7) the compound prepared in (2) above (920 mg, 0.76 mmol) was deprotected in 90% aqueous AcOH (20 mL), and then treated with pyridine (0.075 mL, 0.92 mmol) and 2,2,2-trichloro-1,1-dimethylethyl chloroformate (200 mg, 0.84 mmol) in CH$_2$Cl$_2$ followed by diphenyl chlorophosphate (0.24 mL, 1.14 mmol), triethylamine (0.21 mL, 1.52 mmol) and catalytic 4-pyrrolidinopyridine (50 mg) to afford 1.03 g (83%) of 3-benzyloxy-(S)-2-[(R)-3-heptanoyloxytetradecanoylamino]propyl 2-deoxy-4-O-diphenylphosphono-3-O-[(R)-3-heptanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.87 (t, 12H, J=6.3 Hz), 1.1–1.6 (m, 56H), 1.78 (s, 3H), 1.86 (s, 3H), 2.01 (m, 1H), 2.18 (m, 3H), 2.40 (m, 2H), 2.67 (m, 1H), 2.88 (d, 1H, J=6.5 Hz), 2.97 (d, 1H, J=6.9 Hz), 3.41 (m, 2H), 3.72 (m, 1H), 3.82 (m, 1H), 4.24 (m, 1H), 4.42 (d, 1H, J=11.8 Hz), 4.64 (m, 3H), 5.16 (m, 1H), 5.39 (m, 2H), 5.75 (d, 1H, J=4.3 Hz), 6.05 (d, 1H, J=8.4 Hz), 7.22 (m, 15H).

(4) In the same manner as described in Example 2-(7), the compound prepared in (3) above (1.0 g, 0.61 mmol) was deprotected with zinc (2.0 g, 31 mmol) and acylated with (R)-3-heptanoyloxytetradecanoic acid (260 mg, 0.73 mmol) in the presence of EEDQ (220 mg, 0.88 mmol) to afford 203 mg (21%) of 3-benzyloxy-(S)-2-[(R)-3-heptanoyloxytetradecanoylamino]propyl 2-deoxy-4-O-diphenylphosphono-2-[(R)-3-heptanoyloxytetradecanoylamino]-3-O-[(R)-3-heptanoyloxytetradecanoyl]-β-D-glucopyranoside as a colorless amorphous solid.

(5) In the same manner as described in Example 2-(8), the compound prepared in (4) above (203 mg, 0.13 mmol) was hydrogenated in the presence of palladium hydroxide (100 mg) on carbon in EtOH (10 mL) and platinum oxide (200 mg) in EtOH/AcOH (10:1) to afford 39 mg (21%) of 3-hydroxy-(S)-2-[(R)-3-heptanoyloxytetradecanoylamino] propyl 2-deoxy-4-O-phosphono-2-[(R)-3-heptanoyloxytetradecanoylaminol-3-O-[(R)-3-heptanoyloxytetradecanoyl]-β-D-glucopyranoside triethylammonium salt as a white powder: mp 171–172° C.; IR (film) 3305, 2955, 2924, 2853, 1734, 1644, 1553, 1466, 1377, 1170, 1102, 1052, 722 cm$^{-1}$; $^1$H NMR (CDCl$_3$—CD$_3$OD) δ 0.88 (m, 18H), 1.1–1.7 (m, 93H), 2.2–2.7 (m, 12H), 3.06 (q, 6H, J=7.1 Hz), 3.3–4.0 (m, 13H), 4.23 (q, 1H, J=9.3 Hz), 4.43 (d, 1H, J=8.2 Hz), 5.0–5.3 (m, 4H), 7.30 (d, 1H, J=8.5 Hz), 7.43 (d, 1H, J=8.5 Hz); $^{13}$C NMR (CDCl$_3$) δ 173.8, 173.5, 173.2, 170.8, 170.5, 170.2, 101.0, 77.2, 75.5, 73.1, 71.6, 71.1, 70.9, 70.6, 67.8, 61.6, 60.8, 54.4, 50.5, 45.8, 41.6, 41.4, 39.5, 34.6, 34.4, 32.0, 31.6, 29.8, 29.6, 29.4, 28.9, 25.4, 25.1, 22.7, 22.6, 14.1, 8.6.

Anal. Calcd. for C$_{78}$H$_{150}$N$_3$O$_{18}$P.H$_2$O: C, 63.86;H, 10.44; N, 2.86; P, 2.11. Found: C, 63.47;H, 10.20; N, 2.59; P, 2.02.

EXAMPLE 10

B9

PREPARATION OF 4-HYDROXY-(S)-3-[(R)-3-DECANOYLOXYTETRADECANOYL]BUTYL 2-DEOXY-4-O-PHOSPHONO-2-[(R)-3-DECANOYLOXYTETRADECANOYLAMINO]-3-O-[(R)-3-DECANOYLTETRADECANOYL]-62-D-GLUCOPYRANOSIDE TRIETHYLAMMONIUM SALT (COMPOUND (I), R$_1$=R$_2$=R$_3$=N—C$_9$H$_{19}$CO, X=Y=O, N=P=1, M=Q=0, R$_4$=R$_5$=R$_7$=R$_9$=H, R$_6$=OH, R$_8$=PO$_3$H$_2$).

(1) In the same manner as described in Example 4-(3) the compound prepared in Example 4-(1) (3.1 g, 5.9 mmol) and (R)-3-(allyloxycarbonylamino)-4-benzyloxy-1-butanol (1.1 g, 3.94 mmol) were coupled in the presence of boron trifluoride etherate (3.0 mL, 23.6 mmol) to afford 1.96 g (67%) of 4-benzyloxy-(S)-3-(allyloxycarbonylamino)butyl 2-deoxy-3,4,6-tri-O-acetyl-2-(2,2,2-trichloroethoxycarbonylamnino)-β-D-glucopyranoside as an amorphous solid. In the same manner as described in Example 4-(4) the compound prepared above (1.8 g, 2.43 mmol) was deacylated in methanol (25 mL) with ammonium hydroxide (5 mL) and then treated with 2,2-dimethoxypropane (25 mL) and camphorsulfonic acid (100 mg) to afford 1.34 g (84%) of 4-benzyloxy-(S)-3-(allyloxycarbonylamino)butyl 2-deoxy-4,6-O-isopropylidine-2-(2,2,2-trichloroethoxycarbonylamino)-β-D-glucopyranoside.

(2) In the same manner as described in Example 4-(5), the compound prepared in (1) above (1.0 g, 1.53 mmol) was acylated with (R)-3-decanoyloxytetradecanoic acid (670 mg, 1.68 mmol) in the presence of EDC·MeI (550 mg, 1.85 mmol) and 4-pyrrolidinopyridine (50 mg) in CH$_2$Cl$_2$ (15 mL) to afford 1.03 g (65%) of 4-benzyloxy-(S)-3-(allyloxycarbonylamino)butyl 2-deoxy-4,6-O-isopropylidene-3-O-[(R)-3-decanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6H, J=6.9 Hz), 1.1–1.6 (m, 34H), 1.37 (s, 3H), 1.47 (s, 3H), 1.85 (m, 2H), 2.28 (t, 2H, J=7.6 Hz), 2.50 (dd, 1H, J=15.1, 6.0 Hz), 2.63 (dd, 1H, J=15.1, 6.7 Hz), 3.30 (m, 1H), 3.49 (m, 4H), 3.68 (t, 1H, J=9.4 Hz), 3.77 (t, 1H, J=10.4 Hz), 3.92 (m, 3H), 4.54 (m, 5H), 4.69 (m, 2H), 5.1–5.4 (m, 4H), 5.91 (m, 1H), 7.33 (m, 5H).

(3) In the same manner as described in Example 4-(6) the compound prepared in (2) above (1.0 g, 0.97 mmol) was deprotected in THF (20 mL) in the presence of dimethyl malonate (1.0 mL, 0.88 mmol) and tetrakis (triphenylphosphine)palladium(0) (200 mg) and then acylated with (R)-3-decanoyloxytetradecanoic acid (425 mg, 1.07 mmol) in the presence of EEDQ (317 mg, 1.28 mmol) to afford 660 mg (51%) of 4-benzyloxy-(S)-3-[(R)-3- decanoyloxytetradecanoylamino]propyl 2-deoxy-4,6-O-isopropylidene-3-O-[(R)-3-decanoyloxytetradecanoyl]-2-(2,2,2-trichloroethoxycarbonylamino)-β-D-glucopyranoside as a colorless amorphous solid: $^1$H NMR (CDCl$_3$) δ 0.88 (t, 12H, J=6.6 Hz), 1.1–1.7 (m, 68H), 1.37 (s, 3H), 1.47 (s, 3H), 2.26 (q, 2H, J=7.1 Hz), 2.41 (m, 2H), 2.62 (dd, 1H, J=14.9, 6.4 Hz), 3.29 (m, 1H), 3.48 (m, 3H), 3.71 (m, 2H), 3.92 (m, 2H), 4.18 (m, 1H), 4.49 (m, 2H), 4.68 (q, 2H, J=11.5 Hz), 5.15 (m, 2H), 5.55 (d, 1H, J=8.8 Hz), 6.17 (d, 1H, J=7.2 Hz), 7.32 (m, 5H).

(4) In the same manner as described in Example 4-(7) the compound prepared in (3) above (640 mg, 0.48 mmol) was deprotected in 90% aqueous AcOH (20 mL), and then treated with pyridine (0.047 mL, 0.58 mmol) and 2,2,2-trichloro-1,1-dimethylethyl chloroformate (127 mg, 0.53 mmol) in CH$_2$Cl$_2$ followed by diphenyl chlorophosphate (0.15 mL, 0.72 mmol), triethylamine (0.13 mL, 0.96 mmol) and catalytic 4-pyrrolidinopyridine (50 mg) to afford 389 mg (47%) of 4-benzyloxy-(S)-3-[(R)-3-decanoyloxytetradecanoyl]butyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.88 (t, 12H, J=6.6 Hz), 1.1–1.6 (m, 68H), 1.79 (s, 3H), 1.86 (s, 3H), 2.22 (m, 4H), 2.40 (m, 4H), 3.49 (m, 4H), 3.78 (m, 1H), 3.93 (m, 1H), 4.1–4.5 (m, 5H), 4.9–4.6 (m, 4H), 5.13 (m, 2H), 5.51 (t, 1H, J=8.9 Hz), 5.84 (d, 1H, J=6.9 Hz), 6.09 (d, 1H, J=8.0 Hz), 7.26 (m, 15H).

(5) In the same manner as described in Example 2-(7), the compound prepared in (4) above (375 g, 0.23 mmol) was deprotected with zinc (752 mg, 11.5 mmol) and acylated with (R)-3-decanoyloxytetradecanoic acid (101 mg, 0.25 mmol) in the presence of EEDQ (70 mg, 0.28 mmol) to afford 270 mg (67%) of 4-benzyloxy-(S)-3-[(R)-3-decanoyloxytetradecanoyl]butyl 2-deoxy-4-O-diphenylphosphono-2-[(R)-3-decanoyloxytetradecanoylamino]-3-O-[(R)-3-decanoyltetradecanoyl]-β-D-glucopyranoside as a colorless amorphous solid.

(6) In the same manner as described in Example 2-(8), the compound prepared in (5) above (270 mg, 0.15 mmol) was hydrogenated in the presence of palladium hydroxide (150 mg) on carbon in EtOH (10 mL) and platinum oxide (300 mg) in EtOH/AcOH (10:1) to afford 93 mg (39%) of 4-hydroxy-(S)-3-[(R)-3-decanoyloxytetradecanoyl]butyl 2-deoxy-4-O-phosphono-2-[(R)-3-decanoyloxytetradecanoylamino]-3-O-[(R)-3-decanoyltetradecanoyl]-β-D-glucopyranoside triethylammonium salt as a white powder: mp 179–181° C. (dec): IR (film) 3287, 2956, 2923, 2853, 1734, 1654, 1552, 1466, 1378, 1246, 1164, 1106, 1085, 1052, 721 cm$^{-1}$; $^1$H NMR (CDCl$_3$—CD$_3$OD) δ 0.88 (t, 18H, J=6.9 Hz), 1.1–1.7 (m, 111H), 2.2–2.7 (m, 14H), 3.06 (q, 6H, J=6.9 Hz), 3.2–4.0 (m, 13H), 4.21 (m, 1H), 4.50 (d, 1H, J=7.7 Hz), 5.0–5.3 (m, 4H), 7.11 (m, 2H); $^{13}$C NMR (CDCl$_3$) δ 173.8, 173.5, 173.3, 170.9, 170.5, 170.1, 101.1, 77.2, 75.5, 72.8, 71.3, 71.0, 70.6, 66.4, 64.0, 60.7, 54.8, 50.2, 45.8, 41.6, 39.5, 34.6, 34.5, 34.4, 32.0, 30.6, 29.8, 29.7, 29.6, 29.5, 29.4, 25.4, 25.1, 22.7, 14.2, 8.6.

Anal. Calcd. for C$_{18}$H$_{170}$N$_3$O$_{18}$P: C, 66.65; H, 10.78; N, 2.64; P, 1.95. Found: C, 66.65 H, 10.68; N, 2.50; P, 1.94.

EXAMPLE 11

B10

PREPARATION OF 4-HYDROXY-(S)-2-[(R)-3-DECANOYLOXYTETRADECANOYL]BUTYL 2-DEOXY-4-O-PHOSPHONO-2-[(R)-3-DECANOYLOXYTETRADECANOYLAMINO]-3-O-[(R)-3-DECANOYLTETRADECANOYL]-β-D-GLUCOPYRANOSIDE TRIETHYLAMMONIUM SALT (COMPOUND (I), R$_1$=R$_2$=R$_3$=N—C$_9$H$_{19}$CO, X=Y=O, N=M=Q=0, R$_4$=R$_5$=R$_7$=R$_9$=H, R$_6$=OH, P=2, R$_8$=PO$_3$H$_2$).

(1) In the same manner as described in Example 4-(3) the compound prepared in Example 4-(1) (5.1 g, 9.7 mmol) and (R)-2-(allyloxycarbonylamino)-4-benzyloxy-1-butanol (1.8 g, 6.45 mmol) were coupled in the presence of boron trifluoride etherate (4.9 mL, 38.0 mmol) to afford 2.92 g (61%) of 4-benzyloxy-(S)-2-(allyloxycarbonylamino)propyl 2-deoxy-3,4,6-tri-O-acetyl-2-(2,2,2-trichloroethoxycarbonylamino)-β-D-glucopyranoside as an amorphous solid. In the same manner as described in Example 4-(4) the compound prepared above (2.6 g, 3.51 mmol) was deacylated in methanol (35 mL) with ammonium hydroxide (7 mL) and then treated with 2,2-dimethoxypropane (35 mL) and camphorsulfonic acid (100 mg) to afford 1.9 g (72%) of 4-benzyloxy-(S)-2-(allyloxycarbonylamino)butyl 2-deoxy-4,6-O-isopropylidine-2-(2,2,2-trichloroethoxycarbonylamino)-β-D-glucopyranoside.

(2) In the same manner as described in Example 4-(5), the compound prepared in (1) above (1.0 g, 1.53 mmol) was acylated with (R)-3-decanoyloxytetradecanoic acid (670 mg, 1.68 mmol) in the presence of EDC·MeI (550 mg, 1.85 mmol) and 4-pyrrolidinopyridine (50 mg) in CH$_2$Cl$_2$ (15 mL) to afford 1.28 g (81%) of 4-benzyloxy-(S)-2-(allyloxycarbonylamino)butyl 2-deoxy-4,6-O-isopropylidene-3-O-[(R)-3-decanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6H, J=6.9 Hz), 1.1–1.7 (m, 34H), 1.37 (s, 3H), 1.47 (s, 3H), 1.82 (m, 2H), 2.28 (t, 2H, J=7.7 Hz), 2.50 (dd, 1H, J=15.3, 6.0 Hz), 2.63 (dd, 1H, J=15.2, 6.7 Hz), 3.16 (m, 1H), 3.56 (m, 3H), 3.65 (t, 1H, J=9.6 Hz), 3.75 (t, 1H, J=10.4 Hz), 3.88 (m, 4H), 4.32 (d, 1H, J=8.5 Hz), 4.46 (s, 2H), 4.54 (m, 2H), 4.67 (m, 2H), 4.90 (m, 11H), 5.26 (m, 3H), 5.89 (m, 1H), 7.33 (m, 5H).

(3) In the same manner as described in Example 4-(6) the compound prepared in (2) above (1.25 g, 1.21 mmol) was deprotected in THF (20 mL) in the presence of dimethyl malonate (1.0 mL, 0.88 mmol) and tetrakis(triphenylphosphine)palladium(0) (200 mg) and then acylated with (R)-3-decanoyloxytetradecanoic acid (530 mg, 1.33 mmol) in the presence of EEDQ (362 mg, 1.46 mmol) to afford 1.16 g (72%) of 4-benzyloxy-(S)-3-[(R)-3-decanoyloxytetradecanoylamino]propyl 2-deoxy-4,6-O-isopropylidene-3-O-[(R)-3-decanoyloxytetradecanoyl]-2-(2,2,2-trichloroethoxycarbonylamino)-13-D-glucopyranoside as a colorless amorphous solid: $^1$H NMR (CDCl$_3$) δ 0.88 (t, 12H, J=6.4 Hz), 1.1–1.7 (m, 68H), 1.37 (s, 3H), 1.45 (s, 3H), 2.26 (q, 2H, J=7.4 Hz), 2.34 (m, 1H), 2.50 (dd, 1H, J=15.1, 6.0 Hz), 2.62 (dd, 1H, J=15.4, 6.3 Hz), 3.12 (m, 1H), 3.5–3.95 (m, 7H), 4.14 (m, 1H), 4.29 (d, 1H, J=8.0 Hz), 4.67 (m, 2H), 4.86 (t, 1H, J=9.6 Hz), 5.15 (m, 2H), 6.16 (d, 1H, J=8.3 Hz), 7.35 (m, 5H).

(4) In the same manner as described in Example 4-(7) the compound prepared in (3) above (1.1 g, 0.83 mmol) was deprotected in 90% aqueous AcOH (20 mL), and then treated with pyridine (0.080 mL, 1.0 mmol) and 2,2,2-trichloro-1,1-dimethylethyl chloroformate (220 mg, 0.91 mmol) in $CH_2Cl_2$ followed by diphenyl chlorophosphate (0.26 mL, 1.25 mmol), triethylamine (0.23 mL, 1.66 mmol) and catalytic 4-pyrrolidinopyridine (50 mg) to afford 802 mg (56%) of 4-benzyloxy-(S)-2-[(R)-3-decanoyloxytetradecanoyl]butyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$HNMR ($CDCl_3$) δ 0.87 (t, 12H, J=6.8 Hz), 1.1–1.6 (m, 68H), 1.79 (s, 3H), 1.88 (s, 3H), 2.23 (m, 4H), 2.37 (m, 4H), 3.57 (m, 4H), 3.83 (m, 1H), 4.29 (m, 3H), 4.44 (m, 2H), 4.69 (m, 4H), 5.14 (m, 4H), 5.62 (d, 1H, J=7.6 Hz), 6.15 (d, 1H, J=8.3 Hz), 7.25 (m, 15H).

(5) In the same manner as described in Example 2-(7), the compound prepared in (4) above (750 mg, 0.43 mmol) was deprotected with zinc (1.42 g, 21.7 mmol) and acylated with (R)-3-decanoyloxytetradecanoic acid (190 mg, 0.48 mmol) in the presence of EEDQ (130 mg, 0.53 mmol) to afford 483 mg (64%) of 4-benzyloxy-(S)-2-[(R)-3-decanoyloxytetradecanoyl]butyl 2-deoxy-4-O-diphenylphosphono-2-[(R)-3-decanoyloxytetradecanoylamino]-3-O-[(R)-3-decanoyltetradecanoyl]-β-D-glucopyranoside as a colorless amorphous solid.

(6) In the same manner as described in Example 2-(8), the compound prepared in (5) above (483 mg, 0.27 mmol) was hydrogenated in the presence of palladium hydroxide (150 mg) on carbon in EtOH (10 mL) and platinum oxide (300 mg) in EtOH/AcOH (10:1) to afford 238 mg (55%) of 4-hydroxy-(S)-2-[(R)-3-decanoyloxytetradecanoyl]butyl 2-deoxy-4-O-phosphono-2-[(R)-3-decanoyloxytetradecanoylamino]-3-O-[(R)-3-decanoyltetradecanoyl]-β-D-glucopyranoside triethylammonium salt as a white powder: mp 181–183° C. (dec): IR (film) 3294, 2956, 2923, 2853, 1732, 1650, 1556, 1466, 1377, 1320, 1246, 1172, 1108, 1082, 1058, 859, 721 cm$^{-1}$; $^1$H NMR ($CDCl_3$—$CD_3OD$) δ 0.88 (t, 18H, J=6.9 Hz), 1.1–1.7 (m, 111H), 2.2–2.7 (m, 14H), 3.06 (q, 6H, J=7.1 Hz), 3.2–4.0 (m, 13H), 4.21 (m, 1H), 4.46 (d, 1H, J=8.3 Hz), 5.0–5.3 (m, 4H); $^{13}$C NMR ($CDCl_3$) δ 173.9, 173.4, 173.2, 171.2, 170.7, 101.0, 77.2, 75.4, 73.1, 71.4, 71.3, 71.1, 70.9, 70.6, 60.7, 58.4, 54.7, 46.3, 45.9, 41.6, 41.1, 39.7, 34.8, 34.6, 34.4, 31.9, 29.8, 29.6, 29.5, 29.3, 25.4, 25.3, 25.1, 22.7, 14.1, 8.6.

Anal. Calcd. for $C_{88}H_{170}N_3O_{18}P$: C, 66.51; H, 10.78; N, 2.64; P, 1.95. Found: C, 66.81; H, 10.68; N, 2.53; P, 1.79.

EXAMPLE 12

B11

PREPARATION OF N-[(R)-3-TETRADECANOYLOXYTETRADECANOYL]-O-[2-DEOXY-4-O-PHOSPHONO-2-[(R)-3-TETRADECANOYLOXYNETRADECANOYLAMI-NO]-3-O-[(R)-3-TETRADECANOYLOXYTETRADECANOYL]-β-D-GLUCOPYRANOSYL]-L-SERINE TRIETHYLAMMONIUM SALT (COMPOUND (I), $R_1$=$R_2$=$R_3$=N—$C_{13}H_{27}$CO, X=Y=O, N=M=P=Q=0, $R_4$=$R_5$=$R_7$=$R_9$=H, $R_6$=$CO_2H$, $R_8$=$PO_3H_2$).

(1) In the same manner as described in Example 2-(5), L-serine benzyl ester (0.212 g, 1.08 mmol) was acylated with (R)-3-tetradecanoyloxytetradecanoic acid (0.541 g, 1.19 mmol) in the presence of EDC·MeI (0.353 g, 1.19 mmol) to give 0.642 g (94%) of N-[(R)-3-tetradecanoyloxytetradecanoyl]-L-serine benzyl ester as a waxy solid: mp 56–61° C.; 1H NMR ($CDCl_3$) δ 0.88 (t, 6H, J=7 Hz), 1.1–1.7 (m, 42H), 2.29 (t, 2H, J=7.5 Hz), 2.50 (m, 2H), 3.87 (br t, 1H), 3.95 (m, 2H), 4.65 (m, 1H), 5.1–5.25 (m, 3H), 6.69 (d, 1H, J=7 Hz), 7.34 (br s, 5H).

(2) In the same manner as described in Example 2-(6), the compound prepared in (1) above (0.19 g, 0.30 mmol) and the compound prepared in Example 2-(4) (0.635 g, 0.478 mmol) were coupled in the presence of mercury cyanide (0.3 g, 1.2 mmol) to give 0.425 g (77%) of N-[(R)-3-tetradecanoyloxytetradecanoyl]-O-[2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester as an amorphous solid.

(3) In the same manner as described in Example 2-(7), the compound prepared in (2) above (0.405 g, 0.22 mmol) was deprotected with zinc (0.72 g, 11 mmol) and acylated with (R)-3-tetradecanoyloxytetradecanoic acid (0.12 g, 0.26 mmol) in the presence of EEDQ (0.082 g, 0.33 mmol) to give 0.277 g (66%) of N-[(R)-3-tetradecanoyloxytetradecanoyl]-O-[2-deoxy-4-O-diphenylphosphono-2-[(R)-3-tetradecanoyloxytetradecanoylamino]-3-O-[(R)-3-tetradecanoyloxytetradecanoyl]-β-D-glucopyranosyl]-L-serine benzyl ester as an amorphous solid: $^1$H NMR ($CDCl_3$) δ 0.88 (t, 18H, J=6.5 Hz) 1.0–1.75 (m, 126H), 2.15–2.45 (m, 10H), 2.53 (dd, 1H, J=14.7, 6.0 Hz), 2.67 (dd, 1H, J=14, 6.0 Hz), 3.25 (br t, 1H, J=7 Hz), 3.35–3.75 (m, 4H), 3.88 dd, 1H, J=11.1 Hz), 4.23 dd, 1H, J=11.1, 3 Hz), 4.6–4.75 (m, 2H), 5.03 (d, 1H, J=8.1 Hz), 5.05–5.25 (m, 4H), 5.48 (t, 1H, J=~10 Hz), 6.40 (d, 1H, J=7.5 Hz), 7.01 d, 1H, J=8.1 Hz), 7.1–7.4 (m, 15H).

(4) In the same manner as described in Example 2-(8), the compound repared in (3) above (0.253 g, 0.133 mmol) was hydrogenated in the presence of 5% alladium on carbon (50 mg) and platinum oxide (120 mg) to give 0.155 g (62%) of N-[(R)-3-tetradecanoyloxytetradecanoyl]-O-[2-deoxy-4-O-phosphono-2-[(R)-3-tetradecanoyloxytetradecanoylamnino]-3-O-[(R)-3-tetradecanoyloxytetradecanoyl]-β-D-glucopyranosyl]-L-serine triethylammonium salt as a colorless solid: mp 180° C. (dec); IR (film) 3322, 2956, 2924, 2852, 1736, 1732, 1681, 1673, 1667, 1660, 1651, 1467, 1456, 1247, 1174, 1110, 1081 cm$^{-1}$; $^1$H NMR ($CDCl_3$—$CD_3OD$) δ 0.88 (t, 18H, J=~7 Hz), 1.0–1.7 (m, 135H), 2.2–2.75 (m, 12H), 3.05 (q, 6H, J=7 Hz), 3.30 (br s, 13H), 3.7–3.9 (m, 3H), 3.96 (d, 1H, J=12 Hz), 4.05–4.3 (m, 2H), 4.34 (m, 1H), 4.53 (d, 1H, J=7.8 Hz), 5.05–5.3 (m, 4H), 7.25–7.35 (m, 2H); $^{13}$C NMR ($CDCl_3$) δ 173.4, 173.2, 171.0, 170.3, 170.2, 169.9, 169.8, 100.8, 75.1, 73.4, 71.1, 70.7, 70.4, 70.3, 60.2, 54.3, 45.6, 41.2, 41.1, 39.2, 34.6, 34.4, 34.2, 32.0, 29.8, 29.5, 25.4, 25.2, 22.7, 14.2, 8.6.

Anal. Calcd for $C_{99}H_{190}N_3O_{19}P·5H_2O$: C, 64.35; H, 10.91; N, 2.27; P, 1.68. Found: C, 64.16; H, 10.92; N, 2.37; P, 1.91.

EXAMPLE 13

B12

PREPARATION OF N-[(R)-3-DODECANOYLOXYTETRADECANOYL]-O-[2-DEOXY-4-O-PHOSPHONO-2-[(R)-3-DODECANOYLOXYTETRADECANOYLAMINO]-3-O-[(R)-3-DODECANOYLOXYTETRADECANOYL]-β-D-GLUCOPYRANOSYL]-L-SERINE TRIETHYLAMMONIUM SALT (COMPOUND (I), $R_1$=$R_2$=$R_3$=N—$C_{11}H_{23}$CO, X=Y=O, N=M=P=Q=0, $R_4$=$R_5$=$R_7$=$R_9$=H, $R_6$=$CO_2H$, $R_8$=$PO_3H_2$).

(1) In the same manner as described in Example 2-(5), L-serine benzyl ester (390 mg, 2.0 mmol) was acylated with (R)-3-dodecanoyloxytetradecanoic acid (935 mg, 2.2 mmol) in the presence of EDC·MeI (745 mg, 2.5 mmol) in CH$_2$C$_2$ to afford 1.08 g (90%) of N-[(R)-3-dodecanoyloxytetradecanoyl]-L-serine benzyl ester: mp 53–54° C. $^1$H NMR (CDCl$_3$) δ 0.88 (t, 6H, J=6.5 Hz), 1.1–1.6 (m, 46H), 2.30 (t, 2H, J=7.7 Hz), 2.50 (d, 2H, 5.6 Hz), 2.62 (t, 1H, J=6.2 Hz), 3.97 (m, 2H), 4.65 (m, 1H), 5.19 (m, 3H), 6.63 (d, 1H, J=6.8 Hz), 7.35 (br s, 5H).

(2) In the same manner as described in Example 2-(2), the compound prepared in Example 2-(1) (1.0 g, 2.02 mmol) was acylated with (R)-3-dodecanoyloxytetradecanoic acid (946 mg, 2.22 mmol) in the presence of EDC·MeI (720 mg, 2.4 mmol) and 4-pyrrolidinopyridine (100 mg) in CH$_2$Cl$_2$, and then deprotected in aqueous AcOH (25 mL) to afford 1.30 g (81%) of 2-(trimethylsilyl)ethyl 2-deoxy-3-O-[(R)-3-dodecanoyloxytetradecanoyl]-2-(2,2,2-trichloroethoxycarbonylamino)-β-D-glucopyranoside as an amorphous solid: $^1$H NMR (CDCl$_3$) δ 0.00 (s, 9H), 0.88 (m, 8H), 1.25 (m, 28H), 1.59 (m, 4H), 2.30 (t, 2H, J=7.5 Hz), 2.52 (m, 2H), 3.42 (m, 1H), 3.55 (m, 1H), 3.66 (m, 1H), 3.83 (dd, 1H, J=11.8, 4.6 Hz), 3.94 (m, 2H), 4.57 (d, 1H, J=8.2 Hz), 4.71 (m, 2H), 5.07 (m, 2H), 5.27 (d, 1H, J=8.8 Hz).

(3) In the same manner as described in Example 2-(3), the compound prepared in (2) above (1.30 g, 1.51 mmol) was treated with 2,2,2-trichloro-1,1-dimethylethyl chloroformate (398 mg, 1.66 mmol) and pyridine (0.15 mL, 1.83 mmol) in CH$_2$Cl$_2$ (25 mL) followed by triethylamine (0.42 mL, 3.02 mmol), diphenyl chlorophosphate (0.47 mL, 2.27 mmol) and 4-pyrrolidinopyridine (100 mg) to afford 1.39 g (71%) of 2-(trimethylsilyl)ethyl 2-deoxy-4O-diphenylphosphono-3-O-[(R)-3-dodecanoyloxytetradecanoyl]-6O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.0 (s, 9H), 0.88 (m, 8H), 1.1–1.7 (m, 46H), 1.77 (s, 3H), 1.85 (s, 3H), 2.23 (m, 6H), 3.34 (m, 1H), 3.59 (m, 1H), 3.80 (m, 1H), 3.96 (m, 1H), 4.32 (m, 2 H), 4.63 (m, 2H), 4.83 (d, 1H, J=11.9 Hz), 5.02 (d, 1H, J=8.2 Hz), 5.20 (m, 1H), 5.65 (m, 2H), 7.29 (m, 10H).

(4) The compound prepared in (3) above (1.30 g, 1.0 mmol) in CH$_2$Cl$_2$ (15 mL) was treated at 0° C. with TFA (5 mL) and then allowed to warm to room temperature for 18 h. The solvent was removed in vacuo and the remaining TFA was removed by azeotroping with toluene. The lactol was treated with the Vilsmeier reagent prepared from DMF (0.39 mL, 5.0 mmol) and oxalyl chloride (0.22 mL, 2.5 mmol) in CH$_2$Cl$_2$ (20 mL) at 0° C. The reaction was allowed to warm slowly to room temperature overnight and was partitioned between 50 mL of saturated aqueous NaHCO$_3$ and ether (50 mL). The layers were separated and the organic phase was dried over Na$_2$SO$_4$ and concentrated in vacuo. Purification by flash chromatography on silica gel with 10% EtOAc/hexanes afforded 1.09 g (90%) of 2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-β-D-glucopyranosyl chloride as a white foam: $^1$H NMR (CDCl$_3$) δ 0.88 (t, 6H, J=6.8 Hz), 1.2–1.70 (m, 46H), 1.78 (s, 3H), 1.88 (s, 3H), 2.18 (t, 2H, J=7.7 Hz), 2.43 (m, 2H), 4.30 (m, 4 H), 4.72 (m, 3H), 5.09 (m, H), 5.50 (t, 1H, J=9.5 Hz), 5.79 (d, 1H, J=8.0 Hz), 6.27 (d, 1H, J=3.6 Hz), 7.19 (m, 10H).

(5) To a solution of compounds prepared in (1) and (4) (540 mg, 0.90 mmol, and 1.0 g, 0.82 mmol, respectively) in 1,2-dichloroethane (20 mL), powdered 4A molecular sieves (300 mg) were added and the suspension was stirred for 30 min. AgOTf (1.16 g, 4.5 mmol) was added in one portion, after 30 min the slurry was filtered through silica gel and eluted with 30% EtOAc/hexanes to afford 1.10 g (75%) of N-[(R)-3-dodecanoyloxytetradecanoyl]-O-[2-deoxy-4-O-diphenylphosphono-3-O-[(R)-3-dodecanoyloxytetradecanoyl]-6O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR (CDCl$_3$) δ 0.88 (t, 12H, J=6.5 Hz), 1.1–1.65 (m, 92H), 1.77 (s, 3H), 1.85 (s, 3H), 2.1–2.5 (mn, 8H), 3.67 (m, 2H), 4.30 (m, 3H), 4.72 (m, 5H), 5.18 (m, 4H), 5.46 (m, 1H), 6.07 (m, 1H), 6.62 (d, 1H, J=7.9 Hz), 7.05–7.45 (m, 15H).

(6) In the same manner as described in Example 2-(7), the compound prepared in (5) above (1.0 g, 0.56 mmol) was deprotected with zinc (1.83 g, 28 mmol) and acylated with (R)-3-dodecanoyloxytetradecanoic acid (285 mg, 0.67 mmol) in the presence of EEDQ (185 mg, 0.74 mmol) to afford 420 mg (44%) of N-[(R)-3-dodecanoyloxytetradecanoyl)-O-[2-deoxy-4-O-diphenylphosphono-2-[(R)-3-dodecanoyloxytetradecanoylamino]-3-O-[ (R)-3-dodecanoyloxytetradecanoyl]-β-D-glucopyranosyl]-L-serine benzyl ester as an amorphous solid.

(7) In the same manner as described in Example 2-(8), the compound prepared in (6) above (420 mg, 0.24 mmol) was hydrogenated in the presence of palladium hydroxide on carbon in EtOH (10 mL) and platinum oxide (400 mg) in EtOH/AcOH (10:1) to afford 240 mg (60%) of N-[(R)-3-dodecanoyloxytetradecanoyl]-O-[2-deoxy-4-O-phosphono-2-[(R)-3-dodecanoyloxytetradecanoylamino]-3-O-[(R)-3-dodecanoyloxytetradecanoyl]-β-D-glucopyranosyl]-L-serine triethylammonium salt as a white powder: mp 181–182° C.; IR (film) 3289, 2956, 2920, 2851, 1731, 1656, 1557, 1467, 1378, 1182, 1108, 1080, 1052, 852, 721 cm$^{-1}$; $^1$H NMR (CDCl$_3$—CD$_3$OD) δ 0.88 (t, 18H, J=6.7 Hz), 1.1–1.7 (m, 123H), 2.2–2.7 (m, 12H), 3.06 (q, 6H, J=7.2 Hz), 3.35 (m, 1H), 3.70 (m, 6H), 3.88 (m, 2H), 4.20 (m, 1H), 4.56 (d, 1H, J=8.1 Hz), 4.59 (br s, 1H), 5.16 (m, 4H); $^{13}$C NMR (CDCl$_3$) δ 176.9, 173.3, 173.2, 172.7, 169.6, 169.1, 101.5, 74.8, 71.2, 70.9, 69.2, 60.5, 53.1, 51.4, 46.1, 41.5, 41.0, 39.2, 34.3, 34.2, 34.0, 32.0, 29.8, 29.7, 29.4, 29.2, 25.6, 25.3, 25.2, 25.1, 22.7, 14.1, 8.7.

Anal. Calcd. for C$_{93}$H$_{178}$N$_3$O$_{19}$P.H$_2$O: C, 66.04;H, 10.73; N, 2.48; P, 1.83. Found: C, 66.04;H, 10.73; N, 2.48; P, 1.86.

EXAMPLE 14

B13

PREPARATION OF N-[(R)-3-UNDECANOYLOXYTETRADECANOYL]-O-[2-DEOXY-4-O-PHOSPHONO-2-[(R)-3-UNDECANOYLOXYTETRADECANOYLAMINO]-3-O-[(R)-3-UNDECANOYLOXYTETRADECANOYL]-β-D-GLUCOPYRANOSYL]-L-SERINE TRIETHYLAMMONIUM SALT (COMPOUND (I), R$_1$=R$_2$=R$_3$=N–C$_{10}$H$_{21}$CO, X=Y=O, N=M=P=Q=0, R$_4$=R$_5$=R$_7$=R$_9$=H, R$_6$=CO$_2$H, R$_8$=PO$_3$H$_2$).

(1) In the same manner as described in Example 2-(5), L-serine benzyl ester (390 mg, 2.0 mmol) was acylated with (R)-3-undecanoyloxytetradecanoic acid (905 mg, 2.2 mmol) in the presence of EDC·MeI (745 mg, 2.5 mmol) in CH$_2$Cl$_2$ to afford 1.08 g (92%) of N-[(R)-3-undecanoyloxytetradecanoyl]-L-serine benzyl ester: mp 53–54° C.; $^1$H NMR (CDCl$_3$) δ 0.88 (t, 6H, J=6.9 Hz), 1.1–1.7 (m, 44H), 2.30 (t, 2H, J=7.7 Hz), 2.49 (d, 2H, J=5.8 Hz), 3.99 (m, 2H), 4.65 (m, 1H), 5.19 (m, 3H), 6.58 (d, 1H, J=6.9 Hz), 7.35 (br s, 5H).

(2) In the same manner as described in Example 2-(2), the compound prepared in Example 2-(1) (1.0 g, 2.02 mmol) was acylated with (R)-3-undecanoyloxytetradecanoic acid (915 mg, 2.22 mmnol) in the presence of EDC·MeI (720 mg, 2.4 mmol) and 4-pyrrolidinopyridine (100 mg) in CH$_2$Cl$_2$, and then deprotected in aqueous AcOH (25 mL) to afford 1.41 g (82%) of 2-(trimethylsilyl)ethyl 2-deoxy-3-O-[(R)-3-undecanoyloxytetradecanoyl]-2-(2,2,2-trichloroethoxycarbonylamino)-β-D-glucopyranoside as an amorphous solid: $^1$H NMR (CDCl$_3$) δ 0.00 (s, 9H), 0.88 (m, 8H), 1.25 (m, 32H), 1.60 (m, 4H), 2.31 (t, 2H, J=7.5 Hz), 2.52 (m, 2H), 3.42 (m, 1H), 3.55 (m, 1H), 3.66 (m, 1H), 3.83 (dd, 1H, J=11.8, 4.6 Hz), 3.94 (m, 2H), 4.57 (d, 1H, J=8.2 Hz), 4.71 (m, 2H), 5.07 (m, 2H), 5.27 (d, 1H, J=8.7 Hz).

(3) In the same manner as described in Example 2-(3), the compound prepared in (2) above (1.30, 1.53 mmol) was treated with 2,2,2-trichloro-1,1-dimethylethyl chloroformate (403 mg, 1.68 mmol) and pyridine (0.15 mL, 1.85 mmol) in CH$_2$Cl$_2$ (25 mL) followed by triethylamine (0.43 mL, 3.06 mmol), diphenyl chlorophosphate (0.48 mL, 2.30 mmol) and 4-pyrrolidinopyridine (100 mg) to afford 1.37 g (70%) of 2-(trimethylsilyl)ethyl 2-deoxy-4-O-diphenylphosphono-3-O-[(R)-3-undecanoyloxytetradecanoyl]-6-O-(2,2,2-trichloro-1,1-dimethyethoxycarbonyl)-2-(2,2,2-trichloroethoxycarbonylamino)-β-D-glucopyranoside as an amorphous solid: $^1$H NMR (CDCl$_3$) δ 0.0 (s, 9H), 0.88 (m, 8H), 1.1–1.7 (m, 44H), 1.80 (s, 3H), 1.89 (s, 3H), 2.23 (m, 6H), 3.58 (m, 3H), 4.32 (m, 1H), 4.71 (m, 2H), 4.83 (d, 1H, J=12.1 Hz), 5.01 (d, 1H, J=8.1 Hz), 5.20 (m, 1H), 5.62 (m, 2H), 7.25 (m, 10H).

(4) In the same manner as described in Example 13-(4), the compound prepared in (4) above (1.28 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.12 g (93%) of 2-deoxy-4-O-diphenylphosphono-3-O-[(R)-3-undecanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6H, J=6.7 Hz), 1.1–1.55 (m, 44H), 1.78 (s, 3H), 1.88 (s, 3H), 2.18 (m, 2H), 2.43 (m, 2H), 4.34 (m, 4H), 4.72 (m, 3H), 5.09 (m, 1H), 5.50 (t, 1H, J=9.6 Hz), 5.80 (d, 1H, J=8.0 Hz), 6.26 (d, 1H, J=3.4 Hz), 7.26 (m, 10H).

(5) In the same manner as described in Example 13-(5), compounds prepared in (1) and (4) above (530 mg, 0.90 mmol, and 1.0 g, 0.83 mmol, respectively) were coupled in the presence of AgOTf (1.16 g, 4.5 mmol) to afford 1.11 g (76%) of N-[(R)-3-undecanoyloxytetradecanoyl]-O-[2-deoxy-4-O-diphenylphosphono-3-O-[(R)-3-undecanoyloxytetradecanoyl]-6-O-(2,2,2-trichloro-1,1-dimethylethoxycarbonyl)-2-(2,2,2-trichloroethoxycarbonylamino)-13-D-glucopyranosyl]-L-serine benzyl ester: $^1$H NMR (CDCl$_3$) δ 0.88 (m, 12H), 1.0–1.65 (m, 88H), 1.77 (s, 3H), 1.85 (s, 3H), 2.1–2.5 (m, 8H), 3.37 (m, 1H), 3.64 (m, 1H), 3.85 (m, 1H), 4.30 (m, 3H), 4.78 (m, 5H), 5.18 (m, 4H), 5.46 (m, 1H), 6.07 (m, 1H), 6.62 (d, 1H, J=7.7 Hz), 7.05–7.45 (m, 15H).

(6) In the same manner as described in Example 2-(7), the compound prepared in (5) above (1.0 g, 0.57 mmol) was deprotected with zinc (2.0 g, 30.5 mmol) and acylated with (R)-3-undecanoyloxytetradecanoic acid (280 mg, 0.68 mmol) in the presence of EEDQ (185 mg, 0.75 mmol) to afford 470 mg (50%) of N-[(R)-3-undecanoyloxytetradecanoyl]-O-[2-deoxy-4-O-diphenylphosphono-2-[(R)-3-undecanoyloxytetradecanoylamino]-3-O-((R)-3-undecanoyloxytetradecanoyl]-β-D-glucopyranosyl]-L-serine benzyl ester as an amorphous solid.

(7) In the same manner as described in Example 2-(8), the compound prepared in (6) above (470 mg, 0.27 mmol) was hydrogenated in the presence of palladium hydroxide on carbon in EtOH (10 mL) and platinum oxide (400 mg) in EtOH/AcOH (10:1) to afford 130 mg (30%) of N-[(R)-3-undecanoyloxytetradecanoyl]-O-[2-deoxy-4-O-phosphono-2-[(R)-3-undecanoyloxytetradecanoylamino]-3-O-[(R)-3-undecanoyloxytetradecanoyl]-β-D-glucopyranosyl]-L-serine triethylammonium salt as a white powder: mp 181–183° C.; IR (film) 3294, 2923, 2853, 1734, 1655, 1466, 1377, 1163, 1080, 721 cm$^{-1}$; $^1$H NMR (CDCl$_3$—CD$_3$OD) δ 0.88 (t, 18H, J=6.8 Hz), 1.1–1.7 (m, 117H), 2.2–2.7 (m, 12H), 3.06 (q, 6H, J=7.1 Hz), 3.4–3.2 (m, 5H), 3.6–3.9 (m, 4H), 4.20 (d, 1H, 9.8 Hz), 4.54 (d, 1H, J=8.0 Hz), 4.62 (br. S, 1H), 5.17 (m, 4H); $^{13}$C NMR (CDCl$_3$) δ 173.5, 173.3, 172.8, 172.2, 169.6, 169.1, 101.5, 77.2, 74.8, 0.9, 69.2, 60.5, 58.5, 53.1, 51.5, 46.1, 41.5, 41.1, 39.2, 34.6, 34.4, 34.1, 32.0, 29.8, 9.7, 29.4, 29.2, 25.6, 25.2, 25.1, 22.7, 18.5, 14.2, 8.7.

Anal. Calcd. for C$_{90}$H$_{172}$N$_3$O$_{19}$P: C, 66.26;H, 10.63; N, 2.58; P, 1.90. Found: C, 66.56;H, 10.57; N, 2.47; P, 1.91.

EXAMPLE 15

B14

PREPARATION OF N-[(R)-3-DECANOYLOXYTETRADECANOYL]-O-[2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSYL]-D-SERINE TRIETHYLAMMONIUM SALT (COMPOUND (I), R$_1$=R$_2$=R$_3$=N—C$_9$H$_{19}$CO, X=Y=O, N=M=P—Q=O, R$_4$=R$_5$=R$_7$=R$_9$=H, R$_6$=CO$_2$H, R$_8$=PO$_3$H$_2$).

(1) In the same manner as described in Example 2-(5), D-serine benzyl ester (390 mg, 2.0 mmol) was acylated with (R)-3-decanoyloxytetradecanoic acid (875 mg, 2.2 mmol) in the presence of EDC·MeI (745 mg, 2.5 mmol) in CH$_2$Cl$_2$ to afford 1.05 g (91%) of N-[(R)-3-decanoyloxytetradecanoyl]-D-serine benzyl ester: mp 51–52° C.; $^1$H NMR (CDCl$_3$) δ 0.88 (m, 6H), 1.1–1.7 (m, 34H), 2.30 (t, 2H, J=7.7 Hz), 2.50 (m, 2H),3.68 (s, 1H), 3.93 (d, 2H, J=3.1 Hz), 4.62 (m, 1H), 5.22 (m, 3H), 6.63 (d, 1H, J=6.9 Hz), 7.35 (br s, 5H).

(2) In the same manner as described in Example 2-(2), the compound prepared in Example 2-(1) (1.0 g, 2.02 mmol) was acylated with (R)-3-decanoyloxytetradecanoic acid (884 mg, 2.22 mmol) in the presence of EDC·MeI (720 mg, 2.4 mmol) and 4-pyrrolidinopyridine (100 mg) in CH$_2$Cl$_2$, and then deprotected in aqueous AcOH (25 mL) to afford 1.30 g (77%) of 2-(trimethylsilyl)ethyl 2-deoxy-3-O-[(R)-3-decanoyloxytetradecanoyl]-2-(2,2,2-trichloroethoxycarbonylamino)-β-D-glucopyranoside as an amorphous solid: $^1$H NMR (CDCl$_3$) δ 0.00 (s, 9H), 0.88 (m, 8 H), 1.25 (m, 30H), 1.59 (m, 4H), 2.30 (t, 2H, J=7.5 Hz), 2.52 (m, 2H), 3.42 (m, 1 H), 3.55 (m, 1H), 3.66 (m, 1H), 3.83 (dd, 1H, J=11.8, 4.6 Hz), 3.94 (m, 2H), 4.57 (d, 1H, J=8.2 Hz), 4.71 (m, 2H), 5.07 (m, 2H), 5.27 (d, 1H, J=8.8 Hz).

(3) In the same manner as described in Example 2-(3), the compound prepared in (2) above (1.25 g, 1.50 mmol) was treated with 2,2,2-trichloro-1,1-dimethylethyl chloroformate (396 mg, 1.65 mmol) and pyridine (0.15 mL, 1.81 mmol) in CH$_2$Cl$_2$ (25 mL) followed by triethylamine (0.42 mL, 3.00 mmol), diphenyl chlorophosphate (0.47 mL, 2.25 mmol) and 4-pyrrolidinopyridine (100 mg) to afford 1.31 g (69%) of 2-(trimethylsilyl)ethyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.0 (s, 9H), 0.89 (m, 8H), 1.1–1.7 (m, 34H), 1.82 (s, 3H), 1.90 (s, 3H), 2.30 (m, 4H), 3.40 (q, 1H, J=9.6 Hz), 3.65 (m, 1H), 3.89 (m, 1H), 4.32 (m, 2H), 4.63 (m, 2H), 4.82 (d, 1H, J=12.1 Hz), 5.01 (d, 1H, J=8.2 Hz), 5.63 (m, 2H), 7.29 (m, 10H).

(4) In the same manner as described in Example 13-(4), the compound prepared in (3) above (1.27 g, 1.0 mmol) was deprotected with TFA (5 mL) and then treated with the Vilsmeier reagent generated from DMP (0.39 mL, 5.0 mmol) and oxalyl chloride (0.22 mL, 2.5 mmol) to give 1.06 g (89%) of 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6H, J=6.6 Hz), 1.1–1.55 (m, 34 H), 1.78 (s, 3H), 1.88 (s, 3H), 2.18 (t, 2H, J=7.7 Hz), 2.43 (m, 2H), 4.32 (m, 4H), 4.71 (m, 3H), 4.83 (m, 3H), 5.09 (m, 1H), 5.50 (t, 1H, J=9.5 Hz), 5.77 (d, 1H, J=8.0 Hz), 6.26 (d, 1H, J=3.4 Hz), 7.20 (m, 10H).

(5) In the same manner as described in Example 13-(5), compounds prepared in (1) and (4) above above (520 mg, 0.90 mmol, and 1.0 g, 0.84 mmol, respectively) were coupled in the presence of AgOTf (1.16 g, 4.5 mmol) to afford 1.13 g (78%) of N-[(R)-3-decanoyloxytetradecanoyl]-O-[2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-lucopyranosyl]-D-serine benzyl ester: $^1$H NMR (CDCl$_3$) δ 0.88 (t, 12H, J=6.6 Hz), 1.1–1.65 (m, 68H), 1.82 (s, 3H), 1.89 (s, 3H), 2.2–2.6 (m, 8H), 3.40 (m, 1H), 3.64 (m, 1H), 4.01 (m, 2H), 4.27 (m, 2H), 4.44 (d, 1H, J=7.1 Hz), 4.60 (m, 2H), 4.77 (in, 2H), 5.19 (m, 6H), 6.61 (d, 1H, J=8.3 Hz), 7.05–7.45 (m, 15H).

(6) In the same manner as described in Example 2-(7), the compound prepared in (5) above (1.0 g, 0.58 mmol) was deprotected with zinc (1.9 g, 29 mmol) and acylated with (R)-3-decanoyloxytetradecanoic acid (280 mg, 0.70 mmol) in the presence of EEDQ (190 mg, 0.77 mmol) to afford 420 mg (44%) of N-[(R)-3-decanoyloxytetradecanoyl3-O-deoxy-4-O-diphenylphosphono-2-[(R)-3-decanoyloxytetradecanoylainino]-3-O-[(R)-3-decanoyloxytetradecanoyl]-β-D-glucopyranosyl]-D-serine benzyl ester as an amorphous solid.

(7) In the same manner as described in Example 2-(8), the compound prepared in (6) above (420 mg, 0.25 mmol) was hydrogenated in the presence of palladium hydroxide on carbon in EtOH (10 mL) and platinum oxide (400 mg) in EtOH/AcOH (10:1) to afford 118 mg (30%) of N-[(R)-3-decanoyloxytetradecanoyl]-O-[2-deoxy-4-O-phosphono-2-[(R)-3-decanoyloxytetradecanoylamino]-3-O-[(R)-3-decanoyloxytetradecanoyl]-β-D-glucopyranosyl]-D-serine triethylammonium salt as a white powder: mp 179–181° C.; IR (film) 3283, 3100, 2921, 2852, 1732, 1660, 1651, 1564, 1556, 1464, 1417, 1378, 1322, 1181, 1061, 856, 722 cm$^{-1}$; $^1$H NMR (CDCl$_3$—CD$_3$OD) δ 0.88 (t, 18H, J=6.8 Hz), 1.1–1.7 (m, 111H), 2.2–2.7 (m, 12H), 3.06 (m, 6H), 3.33 (m, 5H), 3.78 (m, 2H), 3.95 (m, 2H), 4.22 (m, 2H), 4.45 (d, 1H, J=7.5 Hz), 4.68 (br. s, 1H), 5.13 (m, 3H), 5.26 (m, 1H); $^{13}$C NMR (CDCl$_3$) δ δ 173.7, 173.5, 173.1, 171.1, 169.9, 100.3, 75.1, 73.9, 71.9, 71.1, 70.9, 70.2, 60.9, 53.9, 52.7, 46.0, 41.3, 40.8, 39.4, 34.6, 34.4, 31.9, 29.8, 29.7, 29.5, 29.4, 25.6, 25.4, 25.2, 25.1, 22.7, 14.1, 8.6.

Anal. Calcd. for C$_{87}$H$_{166}$N$_3$O$_{19}$P: C, 65.75;H, 10.53; N, 2.64; P, 1.95. Found: C, 65.32;H, 10.28; N, 2.53; P, 1.89.

EXAMPLE 16

B15

PREPARATION OF N-[(R)-3-DECANOYLOXYTETRADECANOYL]-O-[2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSYL]-L-SERINE TRIETHYLAMMONIUM SALT. (COMPOUND (I), R$_1$=R$_2$=R$_3$=N—C$_9$H$_{19}$CO, X=Y=O, N= M=P=Q=0, R$_4$=R$_5$=R$_7$=R$_9$=H, R$_6$=CO$_2$H, R$_8$=PO$_3$H$_2$).

(1) In the same manner as described in Example 2-(5), L-serine benzyl ester (250 mg, 1.08 mmol) was acylated with (R)-3-decanoyloxytetradecanoic acid (478 mg, 1.2 mmol) in the presence of EDC·MeI (357 mg, 1.2 mmol) in CH$_2$Cl$_2$ to afford 0.52 g (84%) of N-[(R)-3-heptanoyloxytetradecanoyl]-L-serine benzyl ester: mp 52–53° C.; $^1$H NMR (CDCl$_3$) δ 0.87 (t, 6H, J=6.9 Hz), 1.1–1.7 (m, 34H), 2.29 (t, 2 H, J=7.5 Hz), 2.49 (d, 2H, J=5.8 Hz), 3.67 (s, 1H), 3.97 (m, 2H), 4.63 (m, 1H), 5.19 (m, 3H), 6.61 (d, 1H, J=7.1 Hz), 7.35 (brs, 5H).

(2) In the same manner as described in Example 13-(5), the compound prepared in (1) above (500 mg, 0.87 mmol), and the compound prepared in Example 15-(4) (1.08 g, 0.90 mmol) were coupled in the presence of AgOTf (1.16 g, 4.5 mmol) to afford 1.35 g (89%) of N-[(R)-3-decanoyloxytetradecanoyl]-O-[2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR (CDCl$_3$) δ 0.88 (t, 12H, J=6.6 Hz), 1.0–1.65 (m, 68H), 1.77 (s, 3H), 1.85 (s, 3H), 2.1–2.5 (m, 8H), 3.38 (q, 1H, J=9.1 Hz), 3.65 (m, 1H), 3.84 (m, 1H), 4.27 (m, 3H), 4.70 (m, 5H), 4.84 (m, 4H), 5.14 (m, 3H), 5.46 (t, 1H, J=9.7 Hz), 6.07 (m, 1H), 6.62 (d, 1H, J=8.0 Hz), 7.05–7.45 (m, 15H).

(3) In the same manner as described in Example 2-(7), the compound prepared in (2) above (600 mg, 0.34 mmol) was deprotected with zinc (1.13 g, 17.2 mmol) and acylated with (R)-3-decanoyloxytetradecanoic acid (150 mg, 0.38 mmol) in the presence of EEDQ (124 mg, 0.50 mmol) to afford 362 mg (60%) of N-[(R)-3-decanoyloxytetradecanoyl]-O-[2-deoxy-4-O-diphenylphosphono-2-[(R)-3-decanoyloxytetradecanoylamino]-3-O-[(R)-3-decanoyloxytetradecanoyl]-β-D-glucopyranosyl]-L-serine benzyl ester as an amorphous solid.

(4) In the same manner as described in Example 2-(8), the compound prepared in (3) above (300 mg, 0.17 mmol) was hydrogenated in the presence of palladium on carbon (100 mg) and platinum oxide (200 mg) in TBF/AcOH (10:1) to afford 120 mg (44%) of N-[(R)-3-decanoyloxytetradecanoyl]-O-[2-deoxy-4-O-phosphono-2-[(R)-3-decanoyloxytetradecanoylamino]-3-O-[(R)-3-decanoyloxytetradecanoyl]-β-D-glucopyranosyl]-L-serine triethylammonium salt as a white powder: mp 175–176° C.; IR (film) 3304, 2956, 2923, 2853, 1733, 1654, 1541, 1466, 1377, 1164, 1107, 1080, 845, 721 cm$^{-1}$; H NMR (CDCl$_3$—CD$_3$OD) δ 0.88 (t, 18 H, J=6.9 Hz), 1.1–1.7(m, 111H), 2.2–2.75 (m, 12H), 3.07 (q,6H, J=7.2 Hz), 3.37 (m, 1H), 3.5–3.95 (m, 8H), 4.21 (q, 1H, 11.0 Hz), 4.54 (d, 1H, J=8.9 Hz), 4.61 (br. s, 1H), 5.17 (m, 4H), 7.10 (d, 1H, J=9.0 Hz), 7.43 (d, 1H, J=7.9 Hz); $^{13}$C NMR (CDCl$_3$) δ 176.3, 173.4, 173.2, 172.8, 172.0, 169.6, 169.2, 101.4, 74.7, 70.9, 69.3, 60.4, 53.2, 51.6, 46.1, 41.4, 41.0, 39.1, 34.5, 34.3, 34.2, 34.1, 31.9, 29.8, 29.7, 29.6, 29.4, 29.3, 29.2, 25.5, 25.1, 25.0, 22.7, 14.1, 8.6.

Anal. Calcd. for C$_{87}$H$_{166}$N$_3$O$_{19}$P H$_2$O: C, 65.01;H, 10.54; N, 2.61; P, 1.93. Found: C, 64.92;H, 10.38; N, 2.58; P, 2.06.

EXAMPLE 17

B16

PREPARATION OF N-[(R)-3-NONANOYLOXYTETRADECANOYL]-O-[2-DEOXY-4-O-PHOSPHONO-2-O-(R)-3-NONANOYLOXYTETRADECANOYLAMINO]-3-O-[(R)-3-NONANOYLOXYTETRADECANOYL]-β-D-GLUCOPYRANOSYL]-L-SERINE TRIETHYLAMMONIUM SALT. (COMPOUND (I), R$_1$=R$_2$=R$_3$=N—C$_8$H$_{17}$CO, X=Y=O, N=M=P=Q=0, R$_4$=R$_5$=R$_7$=R$_9$=H, R$_6$=CO$_2$H, R$_8$=PO$_3$H$_2$).

(1) In the same manner as described in Example 2-(5), L-serine benzyl ester (390 mg, 2.0 mmol) was acylated with (R)-3-nonanoyloxytetradecanoic acid (780 mg, 2.2 mmol) in the presence of EDC·MeI (845 mg, 2.5 mmol) in CH$_2$Cl$_2$ to afford 1.0 g (89%) of N-[(R)-3-nonanoyloxytetradecanoyl]-L-serine benzyl ester: mp 52–53° C.; $^1$H NMR (CDCl$_3$) δ 0.88 (t, 6H, J=6.6 Hz), 1.1–1.7 (m, 32H), 2.30 (t, 2 H, J=7.7 Hz), 2.51 (d, 2H, J=5.8 Hz), 2.62 (t, 1H, J=6.0 Hz), 3.98 (m, 2H), 4.65 (m, 1H), 5.19 (m, 3H), 6.58 (d, 1H, J=6.8 Hz), 7.35 (br s, 5H).

(2) In the same manner as described in Example 2-(2), the compound 5 prepared in Example 2-(1) (1.0 g, 2.02 mmol) was acylated with (R)-3-nonanoyloxytetradecanoic acid (852 mg, 2.22 mmol) in the presence of EDC·MeI (720 mg, 2.4 mmol) and 4-pyrrolidinopyridine (100 mg) in CH$_2$Cl$_2$, and then deprotected in aqueous AcOH (25 mL) to afford 1.31 g (79%) of 2-(trimethylsilyl)ethyl 2-deoxy-3-O-[(R)-3-nonanoyloxytetradecanoyl]-2-(2,2,2-trichloroethoxycarbonylamino)-β-D-glucopyranoside as an amorphous solid: $^1$H NMR (CDCl$_3$) δ 0.00 (s, 9H), 0.88 (m, 8 H), 1.25 (m, 28H), 1.59 (m, 4H), 2.30 (t, 2H, J=7.5 Hz), 2.52 (m, 2H), 3.42 (m, 1 H), 3.55 (m, 1H), 3.66 (m, 1H), 3.83 (dd, 1H, J=11.8, 4.6 Hz), 3.94 (m, 2H), 4.57 (d, 1H, J=8.2 Hz), 4.71 (m, 2H), 5.07 (m, 2H), 5.27 (d, 1H, J=8.8 Hz).

(3) In the same manner as described in Example 2-(3), the compound prepared in (2) above (1.25 g, 1.52 mmol) was treated with 2,2,2-trichloro-1,1-dimethylethyl chloroformate (400 mg, 1.67 mmol) and pyridine (0.15 mL, 1.84 mmol) in CH$_2$Cl$_2$ (25 mL) followed by triethylamine (0.42 mL, 3.04 mmol), diphenyl chlorophosphate (0.47 mL, 2.28 mmol) and 4-pyrrolidinopyridine (100 mg) to afford 1.30 g (67%) of 2-(trimethylsilyl)ethyl 2-deoxy-4-O-diphenylphosphono-3-O-[(R)-3-nonanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.0 (s, 9H), 0.88 (m, 8H), 1.1–1.7 (m, 32H), 1.82 (s, 3H), 1.89 (s, 3H), 2.22 (m, 6H), 3.33 (m, 1H), 3.53 (m, 1H), 3.80 (m, 1H), 3.96 (m, 1H), 4.31 (m, 2H), 4.55 (m, 2H), 4.83 (d, 1H, J=12.0 Hz), 5.01 (d, 1H, J=7.9 Hz), 5.62 (m, 1H), 7.28 (m, 10H).

(4) In the same manner as described in Example 13-(4), the compound prepared in (3) above (1.26 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.07 g (91%) of 2-deoxy-4-O-diphenylphosphono-3-O-[(R)-3-nonanoyloxytetradecanoyl]-6-O-(2,2,2-trichloro-1, 1 -dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6H, J=6.9 Hz), 1.25–1.55 (m, 32H), 1.78 (s, 3H), 1.88 (s, 3H), 2.18 (t, 2H, J=7.7 Hz), 2.43 (m, 2H), 4.34 (m, 4H), 4.70 (m, 3H), 4.83 (m, 3H), 5.09 (m, 1H), 5.51 (t, 1H, J=10.2 Hz), 5.78 (d, 1H, J=8.0 Hz), 6.25 (d, 1H, J=3.6 Hz), 7.19 (m, 10H).

(5) In the same manner as described in Example 13-(5), compounds prepared in (1) and (4) above (505 mg, 0.90 mmol, and 1.0 g, 0.85 mmol, respectively) were coupled in the presence of AgOTf (1.16 g, 4.5 mmol) to afford 1.03 g (71%) of N-[(R)-3-nonanoyloxytetradecanoyl]-O-(2-deoxy-4-O-diphenylphosphono-3-O-[(R)-3-nonanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR (CDCl$_3$) δ 0.88 (t, 12H, J=6.9 Hz), 1.0–1.65 (m, 64H), 1.78 (s, 3H), 1.82 (s, 3H), 2.1–2.5 (m, 8H), 3.38 (m, 1H), 3.64 (m, 1H), 3.83 (m, 1H), 4.25 (m, 3H), 4.73 (m, 5 H), 5.18 (m, 5H), 6.07 (m, 1H), 6.60 (d, 1H, J=7.8 Hz), 7.05–7.45 (m, 15H).

(6) In the same manner as described in Example 2-(7), the compound prepared in (5) above (1.0 g, 0.59 mmol) was deprotected with zinc (1.93 g, 29.5 mmol) and acylated with (R)-3-nonanoyloxytetradecanoic acid (273 mg, 0.71 mmol) in the presence of EEDQ (195 mg, 0.78 mmol) to afford 405 mg (42%) of N-[(R)-3-nonanoyloxytetradecanoyl]-O-[deoxy-4-O-diphenylphosphono-2-[(R)-3-nonanoyloxytetradecanoylamino]-3-O-[(R)-3-nonanoyloxytetradecanoyl]-β-D-glucopyranosyl]-L-serine benzyl ester as an amorphous solid.

(7) In the same manner as described in Example 2-(8), the compound prepared in (6) above (405 mg, 0.25 mmol) was hydrogenated in the presence of palladium hydroxide on carbon in EtOH (10 mL) and platinum oxide (400 mg) in EtOH/AcOH (10:1) to afford 185 mg (48%) of N-[(R)-3-nonanoyloxytetradecanoyl]-O-[2-deoxy-4-O-phosphono-2-[(R)-3-nonanoyloxytetradecanoylaminol-3-O-[(R)-3-nonanoyloxytetradecanoyl]-β-D-glucopyranosyl]-L-serine triethylammonium salt as a white powder: mp 177–179° C.; IR (film) 3306, 2955, 2923, 2853, 1732, 1660, 1538, 1467, 1378, 1252, 1165, 1106, 1080, 960, 844, 722 cm$^{-1}$; $^1$H NMR (CDCl$_{13}$—CD$_3$OD) δ 0.88 (t, 18H, J=6.8 Hz), 1.1–1.7 (m, 105H), 2.2–2.75 (m, 12H), 3.07 (q, 6H, J=7.1 Hz), 3.2–3.5 (m, 5H), 3.85 (m, 4H), 4.23 (d, 1H, 10.2 Hz), 4.51 (d, 1H, J=8.0 Hz), 4.64 (br. s, 1H), 5.18 (m, 4H); $^{13}$C NMR (CDCl$_3$) δ 173.3, 172.8, 172.2, 169.6, 169.1, 101.5, 74.8, 70.9, 70.8, 69.3, 60.5, 53.2, 51.5, 46.1, 41.5, 41.0, 39.2, 34.5, 34.3, 34.1, 32.0, 31.9, 29.8, 29.6, 29.4, 29.3, 25.6, 25.2, 25.1, 22.7, 14.1, 8.7.

Anal. Calcd. for C$_{84}$H$_{160}$N$_3$O$_{19}$P: C, 65.21;H, 10.42; N, 2.72; P, 2.00. Found: C, 65.48;H, 10.32; N, 2.62; P, 2.12.

EXAMPLE 18

B17

PREPARATION OF N-[(R)-3-OCTANOYLOXYTETRADECANOYL]-O-[2-DEOXY-4-O-PHOSPHONO-2-[(R)-3-OCTANOYLOXYTETRADECANOYLAMINO]-3-O-[(R)-3-OCTANOYLOXYTETRADECANOYL]-β-D-GLUCOPYRANOSYL]-L-SERINE TRIETHYLAMMONIUM SALT (COMPOUND (I), $R_1=R_2=R_3=N-C_7H_{15}CO$, X=Y=O, N=M=P=Q=0, $R_4=R_5=R_7=R_9=H$, $R_6=CO_2H$, $R_8=PO_3H_2$).

(1) In the same manner as described in Example 2-(5), L-serine benzyl ester (390 mg, 2.0 mmol) was acylated with (R)-3-octanoyloxytetradecanoic acid (815 mg, 2.2 mmol) in the presence of EDC·MeI (745 mg, 2.5 mmol) in $CH_2Cl_2$ to afford 1.02 g (93%) of N-[(R)-3-octanoyloxytetradecanoyl]-L-serine benzyl ester: mp 50–51° C.; $^1H$ NMR (CDCl$_3$) δ 0.88 (t, 6H, J=6.8 Hz), 1.1–1.7 (m, 30H), 2.30 (t, 2 H, J=7.7 Hz), 2.51 (d, 2H, J=5.8 Hz), 2.60 (t, 1H, J=6.0 Hz), 3.97 (m, 2H), 4.65 (m, 1H), 5.22 (m, 3H), 6.61 (d, 1H, J=6.9 Hz), 7.35 (br s, 5H).

(2) In the same manner as described in Example 2-(2), the compound prepared in Example 2-(1) (1.0 g, 2.02 mmol) was acylated with (R)-3-octanoyloxytetradecanoic acid (821 mg, 2.22 mmol) in the presence of EDC·MeI (720 mg, 2.4 mmol) and 4-pyrrolidinopyridine (100 mg) in $CH_2Cl_2$, and then deprotected in 90% aqueous AcOH (25 mL) to afford 1.35 g (83%) of 2-(trimethylsilyl)ethyl 2-deoxy-3-O-[(R)-3-octanoyloxytetradecanoyl]-2-(2,2,2-tlichloroethoxycarbonylamino)-β-D-glucopyranoside as an amorphous solid: $^1H$ NMR (CDCl$_3$) δ 0.00 (s, 9H), 0.88 (m, 8 H), 1.25 (m, 26H), 1.60 (m, 4H), 2.30 (t, 2H, J=7.5 Hz), 2.53 (m, 2H), 3.42 (m, 1H), 3.53 (m, 1H), 3.66 (m, 1H), 3.83 (dd, 1H, J=11.8, 4.4 Hz), 3.94 (m, 2H), 4.56 (d, 1H, J=8.3 Hz), 4.64 (d, 1H, J=11.8 Hz), 4.77 (d, 1H, J=11.8 Hz), 5.08 (m, 2 H), 5.30 (br. s, 1H).

(3) In the same manner as described in Example 2-(3), the compound prepared in (2) above (1.30 g, 1.61 mmol) was treated with 2,2,2-trichloro-1,1-dimethylethyl chloroformate (425 mg, 1.77 mmol) and pyridine (0.16 mL, 1.95 mmol) in $CH_2Cl_2$ (25 mL) followed by triethylamine (0.45 mL, 3.22 mmol), diphenyl chlorophosphate (0.50 mL, 2.42 mmol) and 4-pyrrolidinopyndine (100 mg) to afford 1.42 g (71%) of 2-(trimethylsilyl)ethyl 2-deoxy-4-O-diphenylphosphono-3-O-[(R)-3-octanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1H$ NMR (CDCl$_3$) δ 0.0 (s, 9H), 0.88 (m, 8H), 1.1–1.7 (m, 30H), 1.82 (s, 3H), 1.89 (s, 3H), 2.23 (m, 6H), 3.37 (m, 1H), 3.65 (m, 1H), 3.83 (m, 1H), 3.96 (m, 1H), 4.55 (m, 2H), 4.83 (d, 1H, J=11.8 Hz), 5.01 (d, 1H, J=8.2 Hz), 5.20 (m, 1H), 7.29 (m, 10H).

(4) In the same manner as described in Example 13-(4), the compound prepared in (3) above (1.24 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.0 g (87%) of 2-deoxy-4-O-diphenylphosphono-3-O-[(R)-3-octanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1H$ NMR (CDCl$_3$) δ 0.88 (t, 6H, J=6.7 Hz), 1.25–1.55 (m, 30H), 1.78 (s, 3H), 1.88 (s, 3H), 2.18 (t, 2H, J=7.7 Hz), 2.43 (m, 2H), 4.29 (m, 4 H), 4.72 (m, 3H), 5.09 (m, 1H), 5.51 (t, 1H, J=9.9 Hz), 5.79 (d, 1H, J=7.9 Hz), 6.25 (d, 1H, J=3.5 Hz), 7.29 (m, 10H).

(5) In the same manner as described in Example 13-(5), compounds prepared in (1) and (4) above (490 mg, 0.90 mmol, and 1.0 g, 0.86 mmol, respectively) were coupled in the presence of AgOTf (1.16 g, 4.5 mmol) to afford 0.99 g (69%) of N-[(R)-3-octanoyloxytetradecanoyl]-O-[2-deoxy-4-O-diphenylphosphono-3-O-[(R)-3-octanoyloxytetradecanoyl]-6-O-(2,2,2-trichloro-1,1-dimethylethoxycarbonyl)-2-(2,2,2-trichloroethoxycarbonylamino)-β-D-glucopyranosyl)-L-serine benzyl ester: $^1H$ NMR (CDCl$_3$) δ 0.88 (t, 12H, J=6.9 Hz), 1.0–1.65 (m, 60H), 1.77 (s, 3H), 1.85 (s, 3H), 2.1–2.5 (m, 8H), 3.37 (m, 1H), 3.65 (m, 1H), 3.83 (m, 1H), 4.27 (m, 3H), 4.72 (m, 5H), 5.18 (m, 4H), 5.46 (t, 1H, J=9.8 Hz), 6.06 (m, 1H), 6.60 (d, 1H, J=8.0 Hz), 7.05–7.45 (m, 15H).

(6) In the same manner as described in Example 2-(7), the compound prepared in (5) above (0.95 g, 0.57 mmol) was deprotected with zinc (1.86 g, 28.5 mmol) and acylated with (R)-3-octanoyloxytetradecanoic acid (252 mg, 0.68 mmol) in the presence of EEDQ (185 mg, 0.75 mmol) to afford 433 mg (47%) of N-[(R)-3-octanoyloxytetradecanoyl]-O-[2-deoxy-4-O-diphenylphosphono-2-[(R)-3-octanoyloxytetradecanoylarnino]-3-O-[(R)-3-octanoyloxytetradecanoyl]-β-D-glucopyranosyl]-L-serine benzyl ester as an amorphous solid.

(7) In the same manner as described in Example 2-(8), the compound prepared in (6) above (433 mg, 0.27 mmol) was hydrogenated in the presence of palladium hydroxide on carbon (250 mg) in EtOH (10 mL) and platinum oxide (400 mg) in EtOH/AcOH (10:1) to afford 196 mg (48%) of N-[(R)-3-octanoyloxytetradecanoyl]-O-[2-deoxy-4-O-phosphono-2-[(R)-3-octanoyloxytetradecanoylamino]-3-O-t(R)-3-octanoyloxytetradecanoyl]-β-D-glucopyranosyl]-L-serine triethylammonium salt as a white powder: mp 177–178° C.; IR (film) 3296, 2956, 2923, 2853, 1732, 1645, 1546, 1466, 1378, 1315, 1170, 1082, 1056, 961, 846, 722 cm$^{-1}$; $^1H$ NMR (CDCl$_3$—CD$_3$OD) δ 0.88 (t, 18H, J=6.6 Hz), 1.1–1.7 20 (m, 99H), 2.2–2.75 (m, 12H), 3.08 (q, 6H, J=7.1 Hz), 3.39 (d, 1H, J=8.8 Hz), 3.6 –4.0 (m, 8H), 4.22 (q, 1H, 10.3 Hz), 4.53 (d, 1H, J=8.2 Hz), 4.63 (m, 1H), 5.18 (m, 4H), 7.04 (d, 1H, J=8.8 Hz), 7.42 (d, 1H, J=8.0 Hz); $^{13}C$ NMR (CDCl$_3$) δ 176.8, 173.3, 173.2, 172.7, 172.2, 169.6, 169.1, 101.5, 74.8, 70.9, 70.8, 69.3, 60.5, 53.2, 51.5, 46.2, 41.5, 41.1, 39.2, 34.5, 34.3, 34.1, 34.0, 32.0, 31.8, 29.8, 29.6, 29.4, 29.3, 29.2, 29.1, 25.6, 25.3, 25.2, 25.0, 22.7, 14.1, 8.7.

Anal. Calcd. for $C_{81}H_{154}N_3O_{19}P\cdot H_2O$: C, 63.87;H, 10.32; N, 2.76; P, 2.03. Found: C, 63.96;H, 10.29; N, 2.69; P, 1.67.

EXAMPLE 19

B18

PREPARATION OF N-[(R)-3-HEPTANOYLOXYTETRADECANOYL]-O-[2-DEOXY-4-O-PHOSPHONO-2-[(R)-3-HEPTANOYLOXYTETRADECANOYLAMINO]-3-O-[(R)-3-HEPTANOYLOXYTETRADECANOYL]-β-D-GLUCOPYRANOSYL]-L-SERINE TRIETHYLAMMONIUM SALT (COMPOUND (I), $R_1=R_2=R_3=N-C_6H_{13}CO$, X=Y=O, N=M=P=Q=0, $R_4=R_5=R_7=R_9=H$, $R_6=CO_2H$, $R_8=PO_3H_2$).

(1) In the same manner as described in Example 2-(5), L-serine benzyl ester (390 mg, 2.0 mmol) was acylated with (R)-3-heptanoyloxytetradecanoic acid (780 mg, 2.2 mmol) in the presence of EDC·MeI (745 mg, 2.5 mmol) in $CH_2Cl_2$ to afford 0.97 g (91%) of N-[(R)-3-heptanoyloxytetradecanoyl]-L-serine benzyl ester: mp 46–48° C.; $^1$H NMR ($CDCl_3$) δ 0.88 (t, 6H, J=6.9 Hz), 1.1–1.7 (m, 28H), 2.30 (t, 2 H, J=7.7 Hz), 2.50 (d, 2H, J=5.8 Hz), 2.62 (t, 1H, J=6.0 Hz), 3.97 (m, 2H), 4.65 (m, 1H), 5.19 (m, 3H), 6.61 (d, 1H, J=6.9 Hz), 7.35 (br s, 5H).

(2) In the same manner as described in Example 2-(2), the compound prepared in Example 2-(1) (1.0 g, 2.02 mmol) was acylated with (R)-3-heptanoyloxytetradecanoic acid (790 mg, 2.22 mmol) in the presence of EDC·MeI (720 mg, 2.4 mmol) and 4-pyrrolidinopyridine (100 mg) in $CH_2Cl_2$, and then deprotected in 90% aqueous AcOH (25 mL) to afford 1.30 g (81%) of 2-(trimethylsilyl)ethyl 2-deoxy-3-O-[(R)-3-heptanoyloxytetradecanoyl]-2-(2,2,2-trichloroethoxycarbonylamno)-β-D-glucopyranoside as an amorphous solid: $^1$H NMR ($CDCl_3$) δ 0.00 (s, 9H), 0.88 (m, 8 H), 1.25 (m, 24H), 1.59 (m, 4H), 2.30 (t, 2H, J=7.5 Hz), 2.52 (m, 2H), 3.42 (m, 1 H), 3.55 (m, 1H), 3.66 (m, 1H), 3.83 (dd, 1H, J=11.5, 4.2 Hz), 3.94 (m, 2H), 4.57 (d, 1H, J=8.3 Hz), 4.64 (d, 1H, J=12.1 Hz), 4.76 (d, 1H, J=11.9 Hz), 5.09 (m, 2 H), 5.31 (d, 1H, J=8.7 Hz).

(3) In the same manner as described in Example 2-(3), the compound prepared in (2) above (1.25 g, 1.58 mmol) was treated with 2,2,2-trichloro-1,1-dimethylethyl chloroformate (417 mg, 1.74 mmol) and pyridine (0.15 mL, 1.91 mmol) in $CH_2Cl_2$ (25 mL) followed by triethylamine (0.44 mL, 3.16 mmol), diphenyl chlorophosphate (0.49 mL, 2.37 mmol) and 4-pyrrolidinopyridine (100 mg) to afford 1.34 g (69%) of 2-(trimethylsilyl)ethyl 2-deoxy-4-O-diphenylphosphono-3-O-[(R)-3-heptanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR ($CDCl_3$) δ 0.0 (S, 9H), 0.88 (m, 8H), 1.1–1.7 (m, 28H), 1.82 (s, 3H), 1.89 (s, 3 H), 2.35 (m, 4H), 3.37 (m, 1H), 3.61 (m, 1H), 3.80 (m, 1H), 4.32 (m, 2H), 4.63 (m, 2 H), 4.83 (d, 1H, J=12.0 Hz), 5.01 (m, 3H, J=8.2 Hz), 5.62 (m, 2H), 7.29 (m, 10H).

(4) In the same manner as described in Example 13-(4), the compound prepared in (3) above (1.23 g, 1.0 mmol) was deprotected with TFA (5 mL) and then treated with the Vilsmejer reagent generated from DNF (0.39 mL, 5.0 mmol) and oxalyl chloride (0.22 mL, 2.5 mmol) to give 1.0 g (87%) of 2-deoxy-4-O-diphenylphosphono-3-O-[(R)-3-heptanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR ($CDCl_3$) δ 0.88 (t, 6H, J=6.9 Hz), 1.25–1.55 (m, 28H), 1.78 (s, 3H), 1.88 (s, 3H), 2.18 (t, 2H, J=7.6 Hz), 2.43 (m, 2H), 4.26 (m, 4 15H), 4.73 (m, 3H), 5.09 (m, 1H), 5.51 (t, 1H, J=10.2 Hz), 5.77 (d, 1H, J=8.0 Hz), 6.25 (d, 1H, J=3.3 Hz), 7.19 (m, 10H).

(5) In the same manner as described in Example 13-(5), compounds prepared in (1) and (4) above (480 mg, 0.90 mmol, and 0.98 g, 0.86 mmol, respectively) were coupled in the presence of AgOTf (1.16 g, 4.5 mmol) to afford 1.06 g (75%) of N-[(R)-3-heptanoyloxytetradecanoyl]-O-[2-deoxy-4-O-diphenyl phosphono-3-O-[(R)-3-heptanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR ($CDCl_3$) δ 0.88 (m, 12H), 1.0–1.65 (m, 56H), 1.77 (s, 3H), 1.85 (s, 3H), 2.1–2.5 (m, 8H), 3.38 (m, 1H), 3.64 (m, 1H), 3.83 (m, 1H), 4.25 (m, 3H), 4.78 (m, 5H), 5.16 (m, 4H), 5.46 (t, 1H, J=9.9 Hz), 6.06 (m, 1H), 6.60 (d, 1H, J=7.7 Hz), 7.05–7.45 (m, 15H).

(6) In the same manner as described in Example 2-(7), the compound prepared in (5) above (1.0 g, 0.61 mmol) was deprotected with zinc (2.0 g, 30.5 mmol) and acylated with (R)-3-heptanoyloxytetradecanoic acid (260 mg, 0.73 mmol) in the presence of EEDQ (200 mg, 0.80 mmol) to afford 440 mg (45%) of N-[(R)-3 -heptanoyloxytetradecanoyl]-O-[2-deoxy-4-O-diphenylphosphono-2-[(R)-3-heptanoyioxytetradecanoylamino]-3-O-[(R)-3-heptanoyloxytetradecanoyl]-β-D-glucopyranosyl]-L-serine benzyl ester as an amorphous solid.

(7) In the same manner as described in Example 2-(8), the compound prepared in (6) above (440 mg, 0.28 mmol) was hydrogenated in the presence of palladium hydroxide on carbon (250 mg) in EtOH (10 mL) and platinum oxide (400 mg) in EtOH/AcOH (10:1) to afford 208 mg (51%) of N-[(R)-3-heptanoyloxytetradecanoyl]-O-[2-deoxy-4-O-phosphono-2-[(R)-3-heptanoyloxytetradecanoylamino]-3-O-[(R)-3-heptanoyloxytetradecanoyl]-β-D-glucopyranosyl]-L-serine triethylammonium salt as a white powder: mp 176–177° C.; IR (film) 3307, 2956, 2924, 2854, 1732, 1650, 1545, 1466, 1378, 1316, 1170, 1080, 956, 841, 722 $cm^{-1}$; $^1$H NMR ($CDCl_3$—$CD_3OD$) δ 0.88 (m, 18H), 1.1–1.7 (m, 93H), 2.2–2.75 (m, 12H), 3.08 (q, 6H, J=7.2 Hz), 3.40 (d, 1H, J=10.2 Hz), 3.6–4.0 (m, 7 H), 4.24 (m, 2H), 4.52 (d, 1H, J=8.0 Hz), 4.63 (m, 1H), 5.19 (m, 4H), 7.04 (d, 1H, J=8.6 Hz), 7.40 (d, 1H, J=8.4 Hz); $^{13}$C NMR ($CDCl_3$) δ 177.1, 173.2, 173.1, 172.7, 172.3, 169.5, 168.9, 101.5, 75.0 74.8, 71.2, 70.9, 69.1, 60.5, 53.1, 51.4, 46.1, 41.5, 41.0, 39.2, 34.5, 34.3, 34.1, 34.0, 31.9, 31.6, 31.5, 29.8, 29.6, 29.4, 29.0, 28.9, 28.8, 25.6, 25.3, 25.1, 25.0, 22.7, 22.6, 14.1, 8.7.

Anal. Calcd. for $C_{78}H_{148}N_3O_{19}P$: C, 64.04;H, 10.20; N, 2.87; P, 2.12. Found: C, 63.77;H, 10.1 1; N, 2.85; P, 2.02.

EXAMPLE 20

B19

PREPARATION OF 2-[(R)-3-TETRADECANOYLOXYTETRADECANOYLAMINO]ETHYL 2-DEOXY-4-O-PHOSPHONO-3-O-[(R)-3-TETRADECANOYOXYTETRADECANOYL]-2-[(R)-3-TETRADECANOYOXYTETRADECANOYLAMINO]-β-D-GLUCOPYRANOSIDE TRIETHYLAMMONIUM SALT (COMPOUND (I), $R_1=R_2=R_3=N—C_{13}H_{27}CO$, X=Y=O, N=M=P=Q=0, $R_4=R_5=R_6=R_7=R_9$=H, $R_8=PO_3H_2$).

(1) 2-Amino-1-(t-butyldiphenylsilyloxy)ethane (330 mg, 1.1 mmol) and (R)-3-tetradecanoyloxytetradecanoic acid (500 mg, 1.1 mmol) were dissolved in $CH_2Cl_2$ (10 mL) and treated with powdered 4 A molecular sieves (500 mg). After 1 h EEDQ (297 mg, 1.2 mmol) was added and the reaction was stirred for 18 h, filtered through Celite® and concentrated in vacuo. The residue was chromatographed over silica gel using 15% EtOAc/hexanes to give 675 mg (92%) of a colorless solid. A portion of this material (500 mg, 0.68 mmol) was deprotected with TBAF (1 M in THF, 1 mL, 1 mmol) in THF (5 mL) by stirring at room temperature for 2 h. The reaction mixture was diluted with $Et_2O$ (50 mL) and washed with brine (2×50 mL). The brine was back extracted with $Et_2O$ (2×50 mL) and the combined organic extracts were dried over $Na_2SO_4$ and concentrated in vacuo to afford 338 mg (62%) of 2-[(R)-3-tetradecanoloxytetradecanoylamino]ethanol as an off-white solid.

(2) In the same manner as described in Example 2-(6), the compound prepared in (1) above (338 mg, 0.68 mmol) and the compound prepared in Example 2-(4) (786 mg, 0.61 mmol) were coupled in the presence of mercury cyanide (770 mg, 3.05 mmol) to give 245 mg (24%) of 2-[(R)-3-tetradecanoyloxytetradecanoylamino]ethyl 2-deoxy-4-O-diphenylphosphono-3-O-[(R)-3-tetradecanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12H, J=6.9 Hz), 1.1–1.8 (m, 84H), 1.81 (s, 3H), 1.89 (s, 3 H), 2.15–2.55 (m, 8H), 3.25 (m, 1H), 3.47 (m, 2H), 3.67 (mn, 1H), 3.83 (m, 2H), 4.28 (dd, 1H, J=12.2, 4.9 Hz), 4.36 (d, 1H, J=11.0 Hz), 4.68 (m, 2H), 4.78 (d, 1H, J=11.6 Hz),4.94(d, 1H, J=11.6 Hz),5.16(m,2H), 5.53 (t, 1H, J=10.0 Hz),6.06 (d, 1H, J=4.9 Hz), 6.19 (m, 1H), 7.25 (m, 10H).

(3) In the same manner as described in Example 2-(7), the compound prepared in (2) above (500 mg, 0.29 mmol) was deprotected with zinc (980 mg, 15 mmol) and then acylated with (R)-3-tetradecanoyloxytetradecanoic acid (155 mg, 0.34 mmol) in the presence of EEDQ (110 mg, 0.44 mmol) to give 315 mg (62%) of 2-[(R)-3-tetradecanoyloxytetradecanoylamino]ethyl 2-deoxy-4-O-diphenylphosphono-3-O-[(R)-3-tetradecanoyoxytetradecanoyl]-2-[(R)-3-tetradecanoyoxytetradecanoylamino]-β-D-glucopyranoside as an amorphous solid.

(4) In the same manner as described in Example 2-(8), the compound prepared in (3) above (200 mg, 0.113 mmol) was hydrogenated in the presence of platinum oxide (100 mg) to give 142 mg (76%) of 2-[(R)-3-tetradecanoyloxytetradecanoylamino]ethyl 2-deoxy-4-O-phosphono-3-O-[(R)-3-tetradecanoyoxytetradecanoyl]-2-[(R)-3-tetradecanoyoxytetradecanoylamino]-β-D-glucopyranoside triethylammonium salt as a white solid: mp 175–176° C.; IR (film) 3285, 3098, 2955, 2919, 2851, 1731, 1659, 1642, 1556, 1468, 1379, 1250, 1228, 1174, 1110, 1083, 1046, 962, 857 cm$^{-1}$; $^1$H NMR (CDCl$_3$—CD$_3$OD) δ 0.88 (t, 18H, J=6.0 Hz), 1.1–1.7 (m, 135H), 2.2–2.7 (m, 15H), 3.06 (q, 6H, J=7.1 Hz), 3.2–4.1 (m, 8 H), 4.21 (q, 1H, J=9.9 Hz), 4.51 (d, 1H, J=8.2 Hz), 5.05–5.25 (m, 4H), 7.33 (d, 1H, J=8.5 Hz), 7.50 (br t, 1H, J=4.8 Hz); $^{13}$C NMR (CDCl$_3$) δ 173.7, 173.3, 170.6, 170.3, 169.9, 100.9, 75.8, 73.0, 71.3, 71.1, 70.9, 70.6, 68.3, 60.6, 55.1, 45.7, 41.6, 41.2, 39.5, 34.6, 34.5, 34.4, 32.0, 29.8, 29.4, 29.3, 25.4, 25.1, 22.7, 14.2, 8.6.

Anal. Calcd. for $C_{98}H_{19}(N_3O_{17}P.2H_2O)$: C, 67.28;H, 11.18; N, 2.40; P, 1.77. Found: C, 67.01;H, 11.18; N, 2.15; P, 2.01.

EXAMPLE 21

B20

PREPARATION OF 2-[(R)-3-DECANOYLOXYTETRADECANOYLAMINO]ETHYL 2-DEOXY-4-O-PHOSPHONO-3-O-[(R)-3-DECANOYOXYTETRADECANOYL]-2-[(R)-3-DECANOYLOXYTETRADECANOYLAMINO]-β-D-GLUCOPYRANOSIDE TRIETHYLAMMONIUM SALT (COMPOUND (I), $R_1=R_2=R_3=N-C_9H_{19}CO$, X=Y=O, N=M=P=Q=0, $R_4=R_5=R_6=R_7=R_9=H$, $R_8=PO_3H_2$).

(1) In the same manner as described in Example 20-(1), 2-amino-1-(t-butyldiphenylsilyloxy)ethane (450 mg, 1.5 mmol) was acylated with (R)-3-decanoyloxytetradecanoic acid (600 mg, 1.5 mmol) in the presence of EDC·MeI (594 mg, 2.0 mmol) and then deprotected with TBAF (1.0 M in THF, 2.5 mL, 2.5 mmol) in THF (10 mL) to afford 488 mg (81%) of 2-[(R)-3-decanoyloxytetradecanoylamino]ethanol as an off-white solid.

(2) In the same manner as described in Example 13-(5), the compound prepared in (1) above (385 g, 0.87 mmol) and the compound prepared in Example 15-(4) (1.05 g, 0.87 mmol) were coupled in the presence of AgOTf (560 mg, 2.2 mmol) to give 1.04 g (74%) of 2-[(R)-3-decanoyloxytetradecanoylamino]ethyl 2-deoxy-4-O-diphenylphosphono-3-O-t(R)-3-decanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12H, J=6.9 Hz), 1.1–1.6 (m, 68H), 1.78 (s, 3H), 1.88 (s, 3H), 2.18 (t, 2H, J=7.7 Hz), 2.44 (m, 2H), 4.34 (m, 5H), 4.72 (m, 2H), 4.83 (q, 1H, J=9.3 Hz), 5.09 (m, 1H), 5.51 (t, 1H, J=10.2 Hz), 5.79 (d, 1H, J=8.0 Hz), 6.26 (d, 1H, J=3.4 Hz), 7.31 (m, 10H).

(3) In the same manner as described in Example 2-(7), the compound prepared in (2) above (700 mg, 0.44 mmol) was deprotected with zinc (1.42 g, 21.7 mmol) and then acylated with (R)-3-decanoyloxytetradecanoic acid (190 mg, 0.48 mmol) in the presence of EEDQ (148 mg, 0.6 mmol) to give 432 mg (62%) of 2–1(R)-3-decanoyloxytetradecanoylamino]ethyl 2-deoxy-4-O-diphenylphosphono-3-O-[(R)-3-decanoyoxytetradecanoyl]-2-[(R)-3-decanoyloxytetradecanoylamino]-β-D-glucopyranoside as an amorphous solid.

(4) In the same manner as described in Example 2-(8), the compound prepared in (3) above (400 mg, 0.25 mmol) was hydrogenated in the presence of platinum oxide (200 mg) to give 200 mg (52%) of 2-[(R)-3-decanoyloxytetradecanoylamino]ethyl 2-deoxy-4-O-phosphono-3-O-((R)-3-decanoyoxytetradecanoyl]-2-[(R)-3-decanoyloxytetradecanoylamino]-β-D-glucopyranoside triethylammonium salt as a white solid: mp 165–166° C.; IR (film) 3289, 3094, 2956, 2922, 2853, 1732, 1658, 1644, 1556, 1467, 1379, 1247, 1164, 1107, 1081, 1048 cm$^{-1}$; $^1$H NMR (CDCl$_3$—CD$_3$OD) δ 0.88 (t, 18H, J=6.9 Hz), 1.1–1.7 (m, 111H), 2.2–2.7 (m, 15H), 3.05 (q, 6H, J=7.1 Hz), 3.2–3.85 (m, 9H), 4.52 (d, 1H, J=8.2 Hz), 5.05–5.25 (m, 4H), 7.21 (d, 1H, J=8.5 Hz), 7.42 (br t, 1H); $^{13}$C NMR (CDCl$_3$) δ 173.8, 173.3, 170.7, 170.3, 170.0, 100.9, 75.6, 73.0, 71.3, 70.9, 70.6, 68.3, 60.7, 55.0, 45.8, 41.6, 41.2, 39.5, 34.5, 34.4, 34.1, 31.9, 29.8, 29.6, 29.5, 29.4, 25.4, 25.1, 22.7, 14.2, 8.6.

Anal. Calcd. for $C_{86}H_{166}N_3O_{17}P.H_2O$: C, 66.08;H, 10.83; N, 2.69; P, 1.98. Found: C, 65.80;H, 10.63; N, 2.63; P, 2.04.

EXAMPLE 22

B21

PREPARATION OF 3-[(R)-3-TETRADECANOYLOXYTETRADECANOYLAMINO]PROPYL 2-DEOXY-4-O-PHOSPHONO-3-O-[(R)-3-TETRADECANOYOXYTETRADECANOYL]-2-[(R)-3-TETRADECANOYLOXYTETRADECANOYLAMINO]-β-D-GLUCOPYRANOSIDE TRIETHYLAMMONIUM SALT (COMPOUND (I), $R_1=R_2=R_3=N-C_{13}H_{27}CO$, X=Y=O, N=1, M=P=Q=O, $R_4=R_5=R_6=R_7=R_9=H$, $R_8=PO_3H_2$).

(1) In the same manner as described in Example 20-(1), 3-amino-1-(t-butyldiphenylsilyloxy)propane (470 mg, 1.5 mmol) was acylated with (R)-3-tetradecanoyloxytetradecanoic acid (680 mg, 1.5 mmol) in the presence of EDC·MeI (595 mg, 2.0 mmol) and then deprotected with TBAF (1.0 M in THF, 2.0 mL, 2.0 mmol) in THF (10 mL) to afford 698 mg (91%) of 3-[(R)-3-tetradecanoyloxytetradecanoylamino]-1-propanol as an off-white solid.

(2) In the same manner as described in Example 13-(4), the compound prepared in Example 2-(3) (7.9 g, 5.88 mmol) was deprotected with TFA (10 mL) and then treated with the Vilsmeier reagent generated from DMF (1.8 mL, 23.5 mmol) and oxalyl chloride (1.03 mL, 11.76 mmol) in $CH_2Cl_2$ (60 mL) to give 6.32 g (85%) of 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR ($CDCl_3$) δ 0.88 (t, 6H, J=6.8 Hz), 1.2–1.55 (m, 42H), 1.78 (s, 3H), 1.88 (s, 31H), 2.18 (t, 2H, J=7.5 Hz), 2.43 (m, 211), 4.31 (m, 41H), 4.68 (d, 1H, J=11.9 Hz), 4.74 (d, 1H, J=11.9 Hz), 4.83 (q, 1H, J=9.3 Hz), 5.09 (m, 1H), 5.51 (t, 1H, J=9.7 Hz), 5.78 (d, 1H, J=8.0 Hz), 6.26 (d, 1H, J=3.4 Hz), 7.31 (m, 10H).

(3) In the same manner as described in Example 13-(5), the compound prepared in (1) above (613 mg, 1.2 mmol) and the compound prepared in (2) above (1.5 g, 1.2 mmol) were coupled in the presence of AgOTf (642 mg, 2.5 mmol) to give 1.43 g (68%) of 3-[(R)-3-tetradecanoyloxytetradecanoylaminolpropyl 2-deoxy-4-O-diphenylphosphono-3-O-[(R)-3-tetradecanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR ($CDCl_3$) δ 0.88 (t, 12H, J=6.9 Hz), 1.1–1.8 (m, 86H), 1.82 (s, 3H), 1.89 (s, 3H), 2.20 (t, 2H, J=7.6 Hz), 2.29 (t, 2H, J=7.7 Hz), 2.44 (m, 4H), 3.21 (m, 1H), 3.42 (m, 1H), 3.54 (m, 2H), 3.80 (m, 1H), 3.94 (m, 1H), 4.28 (dd, 1H, J=12.3, 5.2 Hz), 4.38 (d, 1H, J=10.8 Hz), 4.70 (m, 3H), 4.81 (d, 1H, J=8.2 Hz), 5.14 (m, 2H), 5.47 (t, 1H, J=9.6 Hz), 6.13 (d, 1H, J=7.6 Hz), 6.22 (br. s, 1H), 7.25 (m, 10H).

(4) In the same manner as described in Example 2-(7), the compound prepared in (3) above (700 mg, 0.40 mmol) was deprotected with zinc (1.32 g, 20.1 mmol) and then acylated with (R)-3-tetradecanoyloxytetradecanoic acid (200 mg, 0.44 mmol) in the presence of EEDQ (125 mg, 0.5 mmol) to give 435 mg (60%) of 3-[(R)-3-tetradecanoyloxytetradecanoylamino]propyl 2-deoxy-4-O-diphenylphosphono-3-O-[(R)-3-tetradecanoyoxytetradecanoyl]-2-[(R)-3-tetradecanoyloxytetradecanoylamino])-β-D-glucopyranoside as an amorphous solid.

(5) In the same manner as described in Example 2-(8), the compound prepared in (4) above (400 mg, 0.22 mmol) was hydrogenated in the presence of platinum oxide (200 mg) to give 170 mg (45%) of 3-[(R)-3-tetradecanoyloxytetradecanoylaminolpropyl 2-deoxy-4-O-phosphono-3-O-[(R)-3-tetradecanoyoxytetradecanoyl]-2-[(R)-3-tetradecanoyloxytetradecanoylamino])-β-D-glucopyranoside triethylammonium salt as a white solid: mp 171–172° C.; IR (film) 3288, 3094, 2955, 2919, 2850, 1731, 1658, 1344, 1556, 1468, 1378, 1320, 1251, 1226, 1172, 1106, 1083, 1044 $cm^{-1}$; LH NMR ($CDCl_3$—$CD_3OD$) δ 0.88 (t, 18H, J=6.0 Hz), 1.1–1.7 (m, 135H), 2.2–2.7 (m, 15H), 3.06 (q, 6H, J=7.1 Hz), 3.2–4.1 (m, 8H), 4.21 (q, 1H, J=9.9 Hz), 4.51 (d, 1 H. J=8.3 Hz), 5.05–5.25 (m, 4H), 7.23 (t, 1H, J=5.3 Hz), 7.33 (d, 1H, J=8.6 Hz); $^{13}$C NMR ($CDCl_3$) δ 173.5, 173.4, 170.6, 170.2, 169.9, 100.6, 75.8, 71.5, 70.9, 70.5, 66.8, 60.4, 55.3, 45.6, 41.4, 39.4, 36.3, 34.6, 34.5, 34.2, 31.9, 29.7, 29.4, 29.3, 29.1, 25.4, 25.1, 22.7, 14.1, 8.5.

Anal. Calcd. for $C_{99}H_{192}N_3O_{17}P\cdot 2H_2O$: C, 67.42;H, 11.20; N, 2.38; P, 1.76. Found: C, 66.97;H, 11.01; N, 2.38; P, 1.95.

EXAMPLE 23

B22

PREPARATION OF 4-[(R)-3-TETRADECANOYLOXYTETRADECANOYLAMINO]BUTYL 2-DEOXY-4-O-PHOSPHONO-3-O-[(R)-3-TETRADECANOYOXYTETRADECANOYL]-2-[(R)-3-TETRADECANOYLOXYTETRADECANOYLAMINO])-β-D-GLUCOPYRANOSIDE TRIETHYLAMMONIUM SALT (COMPOUND (I), $R_1=R_2=R_3=N-C_{13}H_{27}CO$, X=Y=O, N=2, M=P=Q=O, $R_4=R_5=R_6=R_7=R_9=H$, $R_8=PO_3H_2$).

(1) In the same manner as described in Example 20-(1), 4-amino-1-(t-butyldiphenylsilyloxy)butane (500 mg, 1.53 mmol) was acylated with (R)-3-tetradecanoyloxytetradecanoic acid (695 mg, 1.53 mmol) in the presence of EDC·MeI (595 mg, 2.0 mmol) and then deprotected with TBAF (1.0 M in THF, 2.5 mL, 2.5 mmol) in THF (15 mL) to afford 651 mg (81%) of 4-[(R)-3-tetradecanoyloxytetradecanoylamino]-1-butanol as an off-white solid.

(2) In the same manner as described in Example 13-(5), the compound prepared in (1) above (650 mg, 1.25 mmol) and the compound prepared in Example 22-(2) (1.6 g, 1.25 mmol) were coupled in the presence of AgOTf (1.16 g, 4.5 mmol) to give 1.65 g (75%) of 4-[(R)-3-tetradecanoyloxytetradecanoylamino]butyl 2-deoxy-4-O-diphenylphosphono-3-O-[(R)-3-tetradecanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR ($CDCl_3$) δ 0.88 (t, 12H, J=6.9 Hz), 1.1–1.8 (m, 88H), 1.82 (s, 3H), 1.89 (s, 3H), 2.15–2.55 (m, 8H), 3.24 (m, 2H), 3.50 (m, 2H), 3.83 (m, 2H), 4.27 (dd, 1H, J=12.1, 3.8 Hz), 4.32 (d, 1H, J=11.5 Hz), 4.66 (m, 2H), 4.78 (d, 1H, J=12.1 Hz), 4.89 (d, 1H, J=8.0 Hz), 5.15 (m, 2H), 5.54 (t, 1H, J=9.7 Hz), 5.95 (m, 2H), 7.25 (m, 10H).

(3) In the same manner as described in Example 2-(7), the compound prepared in (2) above (700 mg, 0.39 mmol) was deprotected with zinc (1.30 g, 19.8 mmol) and then acylated with (R)-3-tetradecanoyloxytetradecanoic acid (195 mg, 0.43 mmol) in the presence of EEDQ (125 mg, 0.5 mmol) to give 421 mg (60%) of 4-[(R)-3-tetradecanoyloxytetradecanoylamino]butyl 2-deoxy-4-O-diphenylphosphono-3-O-[(R)-3-tetradecanoyoxytetradecanoyl]-2-[(R)-3-tetradecanoyloxytetradecanoylarino])-β-D-glucopyranoside as an amorphous solid.

(4) In the same manner as described in Example 2-(8), the compound prepared in (3) above (400 mg, 0.22 mmol) was hydrogenated in the presence of platinum oxide (200 mg) to give 212 mg (55%) of 4-[(R)-3-tetradecanoyloxytetradecanoylamino]butyl 2-deoxy-4-O-phosphono-3-O-[(R)-3-tetradecanoyoxytetradecanoyl]-2-[(R)-3-tetradecanoyloxytetradecanoylamino])-β-D-glucopyranoside triethylammonium salt as a white solid: mp 171–172° C.; IR (film) 3298, 2955, 2920, 2851, 1732, 1645, 1550, 1467, 1378, 1181, 1107, 1083, 1044, 721 cm$^{-1}$; $^1$H NMR (CDCl$_3$—CD$_3$OD) δ 0.88 (t, 18H, J=6.9 Hz), 1.1–1.7 (m, 135H), 2.2–2.7 (m, 19H), 3.05 (q, 6H, J=7.1 Hz), 3.18 (m, 2H), 3.3–3.5 (m, 6H), 3.78 (m, 3 H), 3.97 (d, 1H, J=12.5 Hz), 4.23 (q, 1H, J=10.0 Hz), 4.50 (d, 1H, J=8.5 Hz), 5.13 (m, 4H), 7.12 (d, 1H, J=9.1 Hz); $^{13}$C NMR (CDCl$_3$) δ 173.9, 173.4, 173.3, 170.8, 169.9, 169.8, 101.0, 75.6, 73.2, 71.4, 71.1, 70.6, 68.9, 60.7, 54.8, 45.9, 41.5, 39.6, 38.9, 34.6, 34.3, 32.0, 29.8, 29.5, 29.0, 28.9, 26.3, 25.4, 25.1, 22.7, 14.2, 8.7.

Anal. Calcd. for C$_{100}$H$_{194}$N$_3$O$_{17}$P.H$_2$O: C, 68.26;H, 11.23; N, 2.39; P, 1.76. Found: C, 68.21;H, 11.03; N, 2.26; P, 1.73.

EXAMPLE 24

B23

PREPARATION OF 4-[(R)-3-TETRADECANOYLOXYTETRADECANOYLAMINO]HEXYL 2-DEOXY-4-O-PHOSPHONO-3-O-[(R)-3-TETRADECANOYOXYTETRADECANOYL]-2-[(R)-3-TETRADECANOYLOXYTETRADECANOYLAMINO]-β-D-GLUCOPYRANOSIDE TRIETHYLAMMONIUM SALT (COMPOUND (I), R$_1$=R$_2$=R$_3$=N—C$_{13}$H$_{27}$CO, X=Y=O, N=4, M=P=Q=O, R$_4$=R$_5$=R$_6$=R$_7$=R$_9$=H, R$_8$=PO$_3$H$_2$).

(1) In the same manner as described in Example 20-(1), 6-amino-1-(t-butyldiphenylsilyloxy)hexane (1.48 g, 4.15 mmol) was acylated with (R)-3-tetradecanoyloxytetradecanoic acid (2.07 g, 4.56 mmol) in the presence of EDC·MeI (1.35 g, 4.56 mmol) and then deprotected with TBAF (1.0 M in THF, 1.53 mL, 1.53 mmol) in THF (46 mL) to afford 700 mg (30%) of 6-[(R)-3-tetradecanoyloxytetradecanoylamino]-1-hexanol as an off-white solid.

(2) In the same manner as described in Example 13-(5), the compound prepared in (1) above (689 mg, 1.20 mmol) and the compound prepared in Example 22-(2) (1.25 g, 1.00 mmol) were coupled in the presence of AgOTf (1.28 g, 5.0 mmol) to give 1.59 g (94%) of 4-[(R)-3-tetradecanoyloxytetradecanoylamino]hexyl 2-deoxy-4-O-diphenylphosphono-3-O-[(R)-3-tetradecanoyoxytetradecanoyl]6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDC$_3$) δ 0.88 (t, 12H, J=6.6 Hz), 1.1–1.8 (m, 92H), 1.82 (s, 3H), 1.89 (s, 3H), 2.22 (t, 2H, J=7.6 Hz), 2.29 (t, 2H, J=7.4 Hz), 2.45 (m, 4H), 3.22 (m, 1H), 3.46 (m, 2H), 3.83 (m, 2H), 3.94 (m, 1H), 4.31 (m, 2H), 4.64 (m, 2H), 4.83 (d, 1H, J=12.1 Hz), 4.97 (d, 1H, J=7.8 Hz), 5.17 (m, 2H), 5.59 (t, 1H, J=8.8 Hz), 5.75 (m, 1H), 5.84 (d, 1H, J=7.6 Hz), 7.25 (m, 10H).

(3) In the same manner as described in Example 2-(7), the compound prepared in (2) above (1.57 g, 0.88 mmol) was deprotected with zinc (2.88 g, 44.1 mmol) and then acylated with (R)-3-tetradecanoyloxytetradecanoic acid (481 mg, 1.06 mmol) in the presence of EEDQ (327 mg, 1.32 mmol) to give 1.57 g (97%) of 4-[(R)-3-tetradecanoyloxytetradecanoylamino]hexyl 2-deoxy-4-O-diphenylphosphono-3-O-[(R)-3-tetradecanoyoxytetradecanoyl]-2-[(R)-3-tetradecanoyloxytetradecanoylamino])-β-D-glucopyranoside as an amorphous solid.

(4) In the same manner as described in Example 2-(8), the compound prepared in (3) above (1.57 g, 0.85 mmol) was hydrogenated in the presence of platinum oxide (157 mg) to give 130 mg (10%) of 4-[(R)-3-tetradecanoyloxytetradecanoylamino]hexyl 2-deoxy-4-O-phosphono-3-O-[(R)-3-tetradecanoyoxytetradecanoyl]-2-[(R)-3-tetradecanoyloxytetradecanoylamino]-β-D-glucopyranoside triethylammonium salt as a white solid: mp 150–152° C.; IR (film) 3284, 3099, 2954, 2920, 2851, 1731, 1657, 1637, 1557, 1467, 1418, 1378, 1320, 1249, 1179, 1108, 1083, 1044, 856, 721 cm$^{-1}$; $^1$H NMR (CDCl$_3$—CD$_3$OD) δ 0.89 (t, 18H, J=6.6 Hz), 1.1–1.7 (m, 135H), 2.2–2.7 (m, 23H), 3.05 (q, 6H, J=7.1 Hz), 3.18 (m, 2 H), 3.39 (d, 1H, J=8.2 Hz), 3.49 (q, 1H, J=7.5 Hz), 3.82 (m, 2H), 3.99 (d, 1H, J=11.9 Hz), 4.25 (q, 1H, J=8.9 Hz), 4.59 (m, 2H), 5.18 (m, 4H); $^{13}$C NMR (CDCl$_3$) δ 173.7, 173.3, 170.6, 169.7, 169.4, 100.6, 75.5, 73.1, 71.3, 70.9, 70.6, 69.2, 60.6, 55.2, 45.8, 41.7, 41.4, 39.5, 39.4, 34.6, 34.3, 34.2, 34.1, 31.9, 29.7, 29.4, 29.2, 26.5, 25.5, 25.3, 25.1, 22.7, 14.1, 8.6.

Anal. Calcd. for C$_{102}$H$_{198}$N$_3$O$_{17}$P.H$_2$O: C, 68.53;H, 11.28; N, 2.33; P, 1.73. Found: C, 68.63 H, 11.12; N, 2.26; P, 1.66.

EXAMPLE 25

B24

PREPARATION OF N-[(R)-3-TETRADECANOYLOXYTETRADECANOYL]-O-PHOSPHONO-2-[(R)-3-TETRADECANOYLOXYTETRADECANOYLAMINO]-3-O-[(R)-3-TETRADECANOYLOXYTETRADECANOYL]-β-D-GLUCOPYRANOSYL]-L-SERINAMIDE TRIETHYLAMMONIUM SALT (COMPOUND (I), R$_1$=R$_2$=R$_3$=N—C$_{13}$H$_{27}$CO, X=Y=O, N= M=P=Q=0, R$_4$=R$_5$=R$_7$=R$_9$=H, R$_6$=CONH$_2$, R$_8$=PO$_3$H$_2$).

(1) A suspension of L-serinamide hydrochloride (0.157 g, 1.18 mmol) and (R)-3-tetradecanoyloxytetradecanoic acid (0.61 g, 1.34 mmol) in CH$_2$Cl$_2$ (6 mL) was treated with triethylamine (0.18 mL, 1.3 mmol) and the resulting solution was stirred with 4 Å molecular sieves for 30 min. EEDQ (0.437 g, 1.77 mmol) was then added and the mixture was stirred for 16 h at room temperature. The product that precipitated was collected and washed with CH$_2$Cl$_2$ (2×25 mL) to give 0.455 g (71%) of N-[(R)-3-tetradecanoyloxytetradecanoyl]-L-serinamide as a colorless powder: mp 126–130° C.; $^1$H NR (CDCl$_3$) δ 0.88 (t, 6H, J=7 Hz), 1.15–1.7 (m, 42H), 2.31 (t, 2H, J=7.5 Hz), 2.51 (d, 2H, J=6.3 Hz), 3.56 (br s, 1H), 3.65 (dd, 1H, J=11.2, 5.5 Hz), 3.86 (dd, 1H, J=11.2, 4.5 Hz), 4.21 (s, 2H), 4.40 (m, 1H), 5.22 (m, 1H).

(2) In the same manner as described in Example 2-(6), the compound prepared in (1) above (0.23 g, 0.246 mmol) and the compound prepared in Example 2-(4) (0.961 g, 0.745 mmol) were coupled in the presence of mercury cyanide (0.43 g, 1.7 mmol) to give 0.527 g (71%) of N-[(R)-3-tetradecanoyloxytetradecanoyl]-O-[2-deoxy- 4-O-diphenylphosphono-3-O-[(R)-3-tetradecanoyloxytetradecanoyl]-6-O-(2,2,2-trichloro-1,1-dimethylethoxycarbonyl)-2-(2,2,2,-trichloroethoxycarbonylamino)-β-D-glucopyranosyl]-L-serinamide as an amorphous solid: $^1$H NMR (CDCl$_3$) δ 0.88 (t, 12H, J=7H), 1.0–1.7 (m, 84H), 1.80 and 1.89 (2s, 6H), 2.21 (t, 2H, J=7.5 Hz), 2.30 (t, 2H, J=7.5 Hz), 2.37 (m, 2H), 2.47 (m, 2H), 3.54 (m, 1H), 3.68 (dd, 1H, J=8, J=11 Hz), 3.86 (br d, 1H, J=11 Hz), 4.16 (dd, 1H, J=11, 4 Hz), 4.24 (dd, 1H, J=12, 4.3 Hz), 4.40 (d, 1H, J=12 Hz), 4.6–4.8 (m, 4H), 5.00 (d, 1H, J=8 Hz), 5.1–5.25 (m, 2H), 5.4–5.55 (m, 2H), 5.84 (br s, 1H), 6.61 (br s, 2H), 7.1–7.35 (m, 10H).

(3) In the same manner as described in Example 2-(7), the compound prepared in (2) above (0.44 g, 0.254 mmol) was deprotected with zinc (0.83 g, 13 mmol) and then acylated with (R)-3-tetradecanoyloxytetradecanoic acid (0.14 g, 0.31 mmol) in the presence of EEDQ (0.095 g, 0.38 mmol) to give 0.271 g (59%) of N-[(R)-3-tetradecanoyloxytetradecanoyl]-O-[2-deoxy-4-O-diphenylphosphono-2-[(R)-3-tetradecanoyloxytetradecanoylamino]-3-O-t(R)-3-tetradecanoyloxytetradecanoyl]-β-D-glucopyranosyl]-L-serinamide as an amorphous solid: $^1$H NMR (CDCl$_3$) δ 0.88 (t, 18 H, J=6.5 Hz), 1.0–1.7 (m, 126H), 2.03 (br s, 1H), 2.15–2.55 (m, 12H), 3.5–4.05 (m, 5H), 4.14 (dd, 1H, J=10, 3.5 Hz), 4.5–4.65 (m, 2H), 4.68 (d, 1H, J=8.1 Hz), 5.05–5.25 (m, 3H), 5.31 (t, 1H, J=10 Hz), 5.58 (br s, 1H), 6.31 (d, 1H, J=8 Hz), 6.85–6.95 (m, 2H), 7.1–7.4 (m, 10H).

(4) In the same manner as described in Example 2-(8), the compound prepared in (3) above (0.25 g, 0.14 mmol) was hydrogenated in the presence of platinum oxide (0.125 g) to give 0.195 (80%) of N-[(R)-3-tetradecanoyloxytetradecanoyl]-O-[2-deoxy-4-O-phosphono-2-[(R)-3-tetradecanoyloxytetradecanoylaminol-3-O-[(R)-3-tetradecanoyloxytetradecanoyl]-β-D-glucopyranosyl]-L-serinamide triethylammonium salt as a colorless solid: mp 190–191° C. (dec); IR (film) 3418, 3293, 2921, 2850, 1732, 1717, 1651, 1636, 1557, 1540, 1458, 1165, 1033 cm$^{-1}$; $^1$H NMR (CDCl$_3$—CD$_3$OD) δ 0.88 (t, 18H, J=7 Hz), 1.0–1.7 (m, 135H), 2.2–2.7 (m, 12H), 3.05 (q, 6H, J=7.2 Hz), 3.2–3.45 (m), 3.5–4.15 (m, 5H), 4.21 (q, 1H, J=10 Hz), 4.53 (d, 1H, J=8.1 Hz), 4.58 (m, 1H), 5.0–5.3 (m, 4H), 7.25 (d, 1H, J=8.4 Hz), 7.40 (d, 1H, J=7.2 Hz); $^{13}$C NMR (CDCl$_3$—CD$_3$OD) δ 173.7, 173.5, 72.5, 170.7, 170.5, 170.4, 101.4, 75.5, 73.4, 71.1, 70.9, 70.2, 68.6, 60.0, 53.9, 52.2, 5.6, 41.2, 41.0, 38.9, 34.4, 34.2, 31.8, 29.6, 29.5, 29.3, 29.1, 25.2, 24.9, 22.6, 14.0, 8.3.

Anal. Calcd for C$_{99}$H$_{191}$N$_4$O$_{18}$P·2.5H$_2$O: C, 66.00;H, 10.97; N, 3.11; P, 72. Found: C, 66.04;H, 10.99; N, 3.03; P, 1.95.

EXAMPLE 26

B25

PREPARATION OF N-[(R)-3-DECANOYLOXYTETRADECANOYL]-O-[2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSYL]-L-SERINAMIDE TRIETHYLAMMONIUM SALT (COMPOUND (I), R$_1$=R$_2$=R$_3$=N—C$_9$H$_{19}$CO, X=Y=O, N=M=P=Q=O, R$_4$=R$_5$=R$_7$=R$_9$=H, R$_6$=CONH$_2$, R$_8$=PO$_3$H$_2$).

(1) In the same manner as described in Example 25-(1), L-serinamide hydrochloride (169 mg, 1.2 mmol) was acylated with (R)-3-decanoyloxytetradecanoic acid (478 mg, 1.2 mmol) in the presence of EEDQ (371 mg, 1.5 mmol) in CH$_2$Cl$_2$ to afford 428 mg (74%) of N-[(R)-3-decanoyloxytetradecanoyl]-L-serinamide as a white solid: $^1$H NMR (CDCl$_3$) δ 0.88 (t, 6H), 1.1–1.7 (m, 34H), 2.33 (t, 2H, J=7.5 Hz), 2.54 (d, 2H, J=6.6 Hz), 3.35 (s, 2H), 3.72 (dd, 1H, J=11.0, 5.2 Hz), 3.84 (dd, 11H, J=11.3, 5.0 Hz), 4.20 (t, 1H, J=5.1 Hz), 5.26 (t, 1H, J=6.4 Hz).

(2) In the same manner as described in Example 13-(5), the compound prepared in (1) above (410 mg, 0.85 mmol) and the compound prepared in Example 15-(4) (1.05 g, 0.87 mmol) were coupled in the presence of AgOTf (560 mg, 2.2 mmol) to afford 780 g (56%) of N-[(R)-3-decanoyloxytetradecanoyl]-O-[2-deoxy-4-O-diphenyl phosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serinamide as an amorphous solid: $^1$H NMR (CDCl$_3$) δ 0.88 (t, 12H), 1.1–1.6 (m, 68H), 1.80 (s, 3H), 1.89 (s, 3H), 2.30 (m, 8H), 3.53 (m, 1H), 3.68 (m, 1H), 3.85 (br. d, 1H, J=9.4 Hz), 4.15 (dd, 1H, J=10.8, 3.7 Hz), 4.24 (dd, 1H, J 12.3, 4.6 Hz), 4.40 (d, 1H, J=10.8), 4.65 (m, 4H), 5.00 (d, 1H, J=8.2 Hz), 5.18 (m, 2H), 5.46 (m, 2H), 5.83 (m, 1H), 6.60 (m, 2H), 7.30 (m, 10H).

(3) In the same manner as described in Example 2-(7), the compound prepared in (2) above (600 mg, 0.36 mmol) was deprotected with zinc (1.19 g, 18.2 mmol) and acylated with (R)-3-decanoyloxytetradecanoic acid (160 mg, 0.4 mmol) in the presence of EEDQ (124 mg, 0.50 mmol) to afford 371 mg (62%) of N-[(R)-3-decanoyloxytetradecanoyl]-O-[2-deoxy-4-O-diphenylphosphono-2-[(R)-3-decanoyloxytetradecanoylamino]-3-O-[(R)-3-decanoyloxytetradecanoyl]-β-D-glucopyranosyl]-serinamide as an amorphous solid.

(4) In the same manner as described in Example 2-(8), the compound prepared in (3) above (330 mg, 0.20 mmol) was hydrogenated in the presence of platinum oxide (200 mg) to afford 120 mg (44%) of N-[(R)-3-decanoyloxytetradecanoyl]-O-[2-deoxy-4-O-phosphono-2-[(R)-3-decanoyloxytetradecanoylamino]-3-O-[(R)-3-decanoyloxytetradecanoyl]-β-D-glucopyranosyl]-L-serinamide triethylammonium salt as a white powder: mp 187–189° C; IR (film) 3419, 3286, 3220, 3098, 2955, 2922, 2852, 1732, 1680, 1662, 1644, 1559, 1467, 1247, 1167, 1107, 1080, 1051, 965, 913 cm$^{-1}$; $^1$H NMR (CDCl$_3$—CD$_3$OD) δ 0.89 (t, 18H, J=7.0 Hz), 1.1–1.7 (m, 111H), 2.2–2.7 (m, 12H), 3.07 (q, 6H, J=7.1 Hz), 3.68 (m, 1H), 3.87 (m, 1H), 4.09 (dd, 1H, J=10.8, 3.6 Hz), 4.22 (m, 1H), 4.53 (d, 1H, J=8.2 Hz), 4.58 (m, 1H), 5.13 (m, 3H), 5.28 (m, 1H), 7.53 (d, 1H, J=9.0 Hz), 7.56 (d, 1H, J=7.7 Hz); $^{13}$C NMR (CDCl$_3$) δ 173.5, 173.2, 170.2, 169.8, 102.3, 75.7, 73.5, 71.3, 70.7, 70.1, 68.8, 60.8, 53.9, 51.7, 45.8, 41.5, 41.1, 39.1, 34.6, 34.5, 34.2, 32.0, 29.7, 29.6, 29.5, 29.4, 25.7, 25.4, 25.1, 22.7, 14.1, 8.6.

Anal. Calcd. for C$_{87}$H$_{167}$N$_4$O$_{18}$P·H$_2$O: C, 65.05;H, 10.60; N, 3.49; P, 1.93. Found: C, 65.06;H, 10.40; N, 3.31; P, 2.00.

EXAMPLE 27

B26

PREPARATION OF N-[(R)-3-TETRADECANOYLOXYTETRADECANOYL]-O-[2-DEOXY-4-O-PHOSPHONO-2-[(R)-3-TETRADECANOYLOXYTETRADECANOYLAMINO]-3-O-[(R)-3-TRADECANOYLOXYTETRADECANOYL]-β-D-GLUCOPYRANOSYL]-1-SERINE METHYL ESTER TRIETHYLAMMONIUM SALT (COMPOUND (I), R$_1$=R$_2$=R$_3$=N—C$_{13}$H$_{27}$CO, X=Y=O, N=M=P=Q=0, R$_4$=R$_5$=R$_7$=R$_9$=H, R$_6$=CO$_2$ME, R$_8$=PO$_3$H$_2$).

(1) A solution of the compound prepared in Example 12-(2) (0.290 g, 0.157 mmol) in THF (20 mL) was hydrogenated in the presence of 5% palladium on carbon (50 mg) at room temperature and atmospheric pressure for 3 h. The catalyst was removed by filtration and the filtrate concentrated. A solution of the residue in CHCl$_3$ (5 mL) at 0° C. was treated with a solution of diazomethane (0.5 mmol) in ether (5 mL) and then stirred for 30 min at 0° C. AcOH (0.5 mL) was added and the resulting colorless solution was diluted with ether (50 mL), washed with saturated aqueous NaHCO$_3$ (25 mL), dried (Na$_2$SO$_4$) and concentrated. Flash chromatography on silica gel (gradient elution, 20→25%

EtOAcs-hexanes) afforded 0.199 g (72%) of N-[(R)-3-tetradecanoyloxytetradecanoyl]-O-[2-deoxy-4-O-diphenylphosphono-3-O-[(R)-3-tetradecanoyloxytetradecanoyl]-6-O-(2,2,2-trichoro-1,1-dimethylethoxycarbonyl)-2-(2,2,2-trichloroethoxycarbonylamino)-β-D-glucopyranosyl]-L-serine methyl ester as an amorphous solid: $^1$H NMR (CDCl$_3$) δ 0.88 (t, 12H, J=6.5 Hz), 1.1–1.75 (m, 84H), 1.81 and 1.89 (2s, 6H), 2.36 (t, 2H, J=7.5 Hz), 2.25–2.6 (mn, 6H), 3.48 (q, 1H, J=8 Hz), 3.7–3.9 (mn, 5H), 4.2–4.4 (m, 3H), 4.6–4.85 (m, 4H), 4.88 (d, 1H, J=7.8 Hz), 5.03–5.22 (m, 2H), 5.49 (t, 1H, J=9.5 Hz), 6.21 (br s, 1H), 6.59 (d, 1H, J=7.8 Hz), 7.1–7.4 (mn, 10H).

(2) In the same manner as described in Example 2-(7), the compound prepared in (1) above (0.195 g, 0.111 mmol) was deprotected with zinc (0.36 g, 5.5 mmol) and acylated with (R)-3-tetradecanoyloxytetradecanoic acid (0.060 g, 0.13 mmol) in the presence of EEDQ (0.041 g, 0.17 mmol) to give 0.138 g (69%) of N-[(R)-3-tetradecanoyloxytetradecanoyl]-O-[(R)-4-O-diphenylphosphono-2-[(R)-3-tetradecanoyloxytetradecanoylano]-3-O-[(R)-3-tetradecanoyloxytetradecanoyl-β-D-glucopyranosyl]-L-serine methyl ester as an amorphous solid: $^1$H NMR (CDCl$_3$) δ 0.88 t, 18H, J=6.5 Hz), 1.0–1.75 (m, 126H), 2.15–2.45 (m, 10H), 2.52 (dd, 1H, J=14.7, 6 Hz), 2.66 (dd, 1H, J=14.7, 6 Hz), 3.35 (br s, 1H), 3.4–3.8 (m, 7H), 3.88 (dd, 1H, J=11 Hz), 4.18 (dd, 1H, J=11 Hz), 4.6–4.75 (m, 2H), 5.03 (d, 1H, J=7.8 Hz), 5.1–5.25 (m, 3H), 5.50 (t, 1H, J=~9.5 Hz), 6.50 (d, 1H, J=7.2 Hz), 6.97 (d, 1H, J=7.8 Hz), 7.1–7.4 (m, 10H).

(3) In the same manner as described in Example 2-(8), the compound prepared in (2) above (0.100 g, 0.055 mmol) was hydrogenated in the presence of platinum oxide (50 mg) to give 0.055 g (57%) of N-[(R)-3-tetradecanoyloxytetradecanoyl]-O-[2-deoxy-4-O-phosphono-2-[(R)-3-tetradecanoyloxytetradecanoylamino]-3-O-[(R)-3-tetradecanoyloxytetradecanoyl]-β-D-glucopyranosyl]-L-serine methyl ester triethylammonium salt as a colorless solid: mp 142–143° C. (dec); IR (film) 3289, 2955, 2921, 2852, 1733, 1718, 1699, 1652, 1558, 1540, 1521, 1506, 1469, 1457, 1375, 1360, 1259 cm$^{-1}$; $^1$H NMR (CDCl$_3$—CD$_3$OD) δ 0.88 (t, 18H, J=~6.5 Hz), 1.0–1.7 (m, 135H), 2.2–2.7 (m, 12H), 3.05 (q, 6H, J=7.5 Hz), 3.31 (d, 1H, J=9.3 Hz), 3.37 (s, 1H), 3.55–3.9 (m, 10H), 3.97 (d, 1H, J=12 Hz), 4.1–4.25 (m, 2H), 4.55–4.65 (m, 2H), 5.05–5.25 (m, 3H), 7.23 (d, 1H, J=8.1 Hz), 7.47 (d, 1H, J=7.2 Hz); $^{13}$C NMR (CDCl$_3$) δ 173.6, 173.4, 170.5, 170.4, 170.1, 100.7, 75.9, 72.8, 71.2, 70.8, 70.6, 68.5, 60.3, 55.3, 52.7, 52.4, 47.7, 41.5, 40.9, 39.7, 34.6, 34.5, 34.3. 32.0, 29.8, 29.4, 25.4, 25.1, 22.7, 14.2, 8.5.

Anal. Calcd for $C_{100}H_{192}N_3O_{19}P \cdot H_2O$: C, 67.11;H, 10.93; N, 2.35; P, 1.73. Found: C, 66.91;H, 10.93; N, 2.31; P, 2.11.

EXAMPLE 28

B27

PREPARATION OF N-(CARBOXYMETHYL)-N-[(R)-3-TETRADECANOYLOXYTETRADECANOYL]-2-AMINOETHYL 2-DEOXY-4-O-PHOPHONO-2-[(R)-3-TETRADECANOYLOXYTETRADECANOYLAMINO]-3-O-[(R)-3-TETRADECANOYLOXYTETRADECANOYL]-β-d-GLUCOPYRANOSIDE TRIETHYLAMMONIUM SALT (COMPOUND (I), $R_1=R_2=R_3=N-C_{13}H_{27}CO$, X=Y=O, N=M=P=0, $R_4=R_5=R_6=R_9=H$, $R_7=CO_2H$, Q=1, $R_8=PO_3H_2$).

(1) In the same manner as described in Example 2-(5), N-(2-hydroxyethyl)glycine t-butyl ester (0.25 g, 1.43 mmol) was acylated with (R)-3-tetradecanoyloxytetradecanoic acid (0.714 g, 1.57 mmol) in the presence of EDC·MeI (0.466 g, 1.57 mmol) to give 0.46 g (51%) of N-(2-hydroxyethyl)-N-[(R)-3-tetradecanoyloxytetradecanoyl]glycine t-butyl ester as an amorphous solid: $^1$H NMR (CDCl$_3$) δ 0.88 (t, 6H, J=6.5 Hz), 1.15–1.7 (m, 51H), 2.26 (t, 2H, J=7.5 Hz), 2.60 (dd, 1H, J=6.5, 15 Hz), 2.86 (dd, 1H, J=6.7, 15 Hz), 3.40–4.15 (m, 7H), 5.25 (m, 1H).

(2) In the same manner as described in 13-(5), the compound prepared in (1) above (0.21 g, 0.334 mmol) and the compound prepared in Example 22-(2) (0.458 g, 0.368 mmol) were coupled in the presence of AgOTf (0.688 g, 2.68 mmol) to give 0.39 g (64%) of N-(t-butyloxycarbonylmethyl)-N-[(R)-3-tetradecanoyloxytetradecanoyl]-2-aminoethyl 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12H, J=6.5 Hz), 1.0–1.95 (m, 99 H), 2.1–2.6 (m, 7H), 2.84 (dd, 1H, J=5, 15 Hz), 3.2–4.15 (m, 8H), 4.15–4.45 (m, 2H), 4.55–4.9 (m, 3H), 5.00 (d, 1H, J=8 Hz), 5.13 (m, 2H), 5.4–5.65 (m, 1H), 6.16 (d, 1H, J=7 Hz), 7.05–7.4 (m, 10H).

(3) In the same manner as described in Example 2-(7), the compound prepared in (2) above (0.339 g, 0.185 mmol) was deprotected with zinc (0.36 g, 5.54 mmol) and then acylated with (R)-3-tetradecanoyloxytetradecanoic acid (0.100 g, 0.221 mmol) in the presence of EEDQ (0.068 g, 0.276 mmol) to give 0.25 g (71%) of N-(t-butyloxycarbonylmethyl)-N-[(R)-3-tetradecanoyloxytetradecanoyl]-2-aminoethyl 2-deoxy-4-O-phosphono-2-[(R)-3-tetradecanoyloxytetradecanoylamino]-3-O-[(R)-3-tetradecanoyloxytetradecanoyl]-β-D-glucopyranoside as a colorless solid.

(4) In the same manner as described in Example 2-(8), the compound prepared in (3) above (0.25 g, 0.131 mmol) was hydrogenated in the presence of platinum oxide (125 mg) in 9:1 THEF-AcOH (15 mL). The crude hydrogenolysis product was dissolved in $CH_2Cl_2$ (1 mL), cooled to 0° C., and treated dropwise with TFA (0.5 mL). After stirring for 2 h at 0° C., the reaction mixture was concentrated and residual TFA was removed by azeotroping with toluene. The resulting residue (0.23 g) was dissolved in 1% aqueous triethylamine (12 mL) and lyophilized. Flash chromatography on silica gel with chloroform-methanol-water-triethylamine (91:8:0.5:0.5→85:15:0.5:0.5, gradient elution) and further purification by means of acidic extraction as described in Example 2-(8) and lyophilization from 1% aqueous triethylamine (6 mL) afforded 99 mg (43%) of N-(carboxymethyl)-N-[(R)-3-tetradecanoyloxytetradecanoyl]-2-aminoethyl 2-deoxy-4-O-phosphono-2-[(R)-3-tetradecanoyloxytetradecanoylaminol-3-O-[(R)-3-tetradecanoyloxytetradecanoyl]-β-D-glucopyranoside triethylammonium salt as colorless solid: mp 162–163° C. (dec); IR (film) 3286, 2922, 2852, 1732, 1651, 1556, 1455, 1434, 1378, 1260, 1088, 801 cm$^{-1}$; $^1$H NMR (CDCl$_3$) δ 0.88 (t, 18H, J=6.5 Hz), 1.0–1.75 (m, 135H), 2.2–3.0 (m, 14H), 3.04 (q, 6H, J=7.2 Hz), 3.25–3.8 (m, 5H), 3.85–4.3 (m, 5H), 4.55 (d, 1H, J=7.5 Hz), 4.68 (d, 1H, J=8.1 Hz), 5.05–5.35 (m, 4H).

Anal. Calcd for $C_{100}H_{192}N_3O_{19}P \cdot 3H_2O$: C, 65.79;H, 10.60; N, 2.30; P, 1.70. Found: C, 65.82;H, 10.44; N, 2.40; P, 1.79.

EXAMPLE 29

B28

PREPARATION OF N-CARBOXYMETHYL-N-[(R)-3-DECANOYLOXYTETRADECANOYL]-3-AMINOPROPYL 2-DEOXY-4-O-PHOSPHONO-2-[(R)-3-DECANOYLOXYTETRADECANOYLAMINO])-3-O-[(R)-3-DECANOYOXYTETRADECANOYL]-β-d-GLUCOPYRANOSIDE TRIETHYLAMMONIUM SALT (COMPOUND (I), $R_1=R_2=R_3=N-C_9H_{19}CO$, X=Y=O, N=1, M=P=0, $R_4=R_5=R_6=R_9=H$, $R_7=CO_2H$, Q=1, $R_8=PO_3H_2$).

(1) In the same manner as described in Example 2-(5), N-(3-hydroxypropyl)glycine benzyl ester (450 mg, 2.0 mmol) was acylated with (R)-3-decanoyloxytetradecanoic acid (1.0 g, 2.5 mmol) in the presence of EDC·MeI (900 mg, 3.0 mmol) in $CH_2Cl_2$ to afford 0.76 g (63%) of N-(3-hydroxypropyl)-N-[(R)-3-decanoyloxytetradecanoyl] glycine benzyl ester as a colorless oil: $^1$H NMR (CDCl$_3$) (1:1 mixture of rotomers) δ 0.88 (t, 6H, J=6.6 Hz), 1.1–1.7 (m, 35H), 1.78 (m, 1H), 2.26 (q, 2H, J=7.6 Hz), 2.37 and 2.54 (2 dd, 1H, J=14.9, 6.9 Hz), 2.60 and 2.89 (2 dd, 1H, J=14.8, 6.0 Hz), 3.51 (m, 4H), 3.70 (m, 1H), 3.95–4.25 (m, 2H), 5.1–5.25 (m, 3H), 7.35 (m, 5H).

(2) In the same manner as described in Example 13-(5), the compound prepared in (1) above (500 mg, 0.83 mmol), and the compound prepared in Example 15-(4) (1.0 g, 0.83 mmol) were coupled in the presence of AgOTf (1.07 g, 4.15 mmol) to afford 1.27 g (72%) of N-(benzyloxycarbonylmethyl)-N-[(R)-3-decanoyloxytetradecanoyl]-3-aminopropyl 2-deoxy-4-O-diphenylphosphono-3-O-[(R)-3-decanoyoxytetradecanoyl]-6-O-(2,2,2-trichloro-1,1-dimethylethoxycarbonyl)-2-(2,2,2-trichloroethoxycarbonylamino)-β-D-glucopyranoside benzyl ester: $^1$H NMR (CDCl$_3$) (2:1 mixture of rotomers) δ 0.88 (t, 12H, J=6.9 Hz), 1.1–1.7 (m, 69H), 1.80 (s, 3H), 1.88 (s, 3H), 2.1–2.6 (m, 11H), 2.81 (dd, 1H, J=14.8, 6.2 Hz), 3.37 (m, 1H), 3.52 (m, 2H), 3.76 (m, 1H), 3.87 (m, 1H), 4.05 (m, 2H), 4.28 (m, 3H), 4.62 (m, 3H), 4.77 (m, 1H), 4.93 (d, 1H, J=8.2 Hz), 5.15 (m, 4H), 5.46 and 5.61 (2 t, 1H, J=9.5 Hz), 5.95 and 6.05 (2 d, 1H, J=7.5 Hz), 7.1–7.4 (m, 15H).

(3) In the same manner as described in Example 2-(7), the compound prepared in (2) above (1.25 g, 0.71 mmol) was deprotected with zinc (2.31 g, 3.53 mmol) and acylated with (R)-3-decanoyloxytetradecanoic acid (353 mg, 0.89 mmol) in the presence of EEDQ (264 mg, 1.07 mmol) to afford 670 mg (54%) of N-benzyloxycarbonylmethyl-N-[(R)-3-decanoyloxytetradecanoyl]-3-aminopropyl 2-deoxy-4-O-diphenylphosphono-3-O-[(R)-3-decanoyoxytetradecanoyl]-2-[(R)-3-decanoyloxytetradecanoylamino])-β-D-glucopyranoside as an amorphous solid.

(4) In the same manner as described in Example 2-(8), the compound prepared in (3) above (670 mg, 0.38 mmol) was hydrogenated in the presence of palladium hydroxide on carbon (270 mg) and platinum oxide (200 mg) in EtOH/AcOH (10:1) to afford 240 mg (39%) of N-carboxymethyl-N-[(R)-3-decanoyloxytetradecanoyl]-3-aminopropyl 2-deoxy-4-O-phosphono-2-[(R)-3-decanoyloxytetradecanoylamino])-3-O-[(R)-3-decanoyoxytetradecanoyl]-β-D-glucopyranoside triethylammonium salt as a white powder: mp 156–157° C.; IR (film) 3284, 2929, 2853, 2729, 1732, 1655, 1628, 1551, 1466, 1378, 1314, 1164, 1108, 1047, 955, 844, 722 cm$^{-1}$; $^1$H NMR (CDCl$_3$—CD$_3$OD) δ 0.88 (t, 18H, J=6.9 Hz), 1.1–1.7 (m, 111H), 2.27 (q, 6H, J=6.2 Hz), 2.35–2.80 (m, 9H), 3.05 (q, 6H, J=7.2 Hz), 3.25–3.60 (m, 4H), 3.75–4.10 (m, 4H), 4.23 (m, 2H), 4.47 (d, 1H, J=8.2 Hz), 4.61 (d, 1H, J=8.3 Hz), 5.05–5.25 (m, 4H); $^{13}$C NMR (CDCl$_3$) δ 173.4, 173.0, 171.1, 170.6, 170.3, 169.6, 100.5, 74.5, 73.9, 71.4, 71.2, 70.7, 70.2, 67.0, 65.8, 60.7, 54.6, 54.3, 51.4, 49.2, 46.0, 45.4, 42.1, 41.2, 39.4, 38.0, 37.7, 34.5, 34.3, 34.2, 31.9, 29.8, 29.7, 29.6, 29.5, 29.2, 28.1, 25.4, 25.3, 25.1, 22.7, 14.1, 11.1, 8.6.

Anal. Calcd. for $C_{89}H_{170}N_3O_{19}P\cdot H_2O$: C, 65.37; H, 10.60; N, 2.57; P, 1.89. Found: C, 65.35; H, 10.42; N, 2.43; P, 2.05.

EXAMPLE 30

B29

PREPARATION OF N-[(R)-3-HEXANOYLOXYTETRADECANOYL]-O-[2-DEOXY-4-O-PHOSPHONO-2-[(R)-3-HEXANOYLOXYTETRADECANOYLAMINO]-3-O-[(R)-3-HEXANOYLOXYTETRADECANOYL]-α-D-GLUCOPYRANOSYL]-L-SERINAMIDE TRIETHYLAMMONIUM SALT (COMPOUND (I), $R_1=R_2=R_3=N-C_5H_{11}CO$, X=Y=O, N=M=P=Q=0, $R_4=R_5=R_7=R_9=H$, $R_8=CONH_2$, $R_8=PO_3H_2$).

In the same manner as described in Example 26 and cognate steps, N-[(R)-3-hexanoyloxytetradecanoyl]-O-[2-deoxy-4-O-phosphono-2-[(R)-3-hexanoyloxytetradecanoylamino]-3-O-[(R)-3-hexanoyloxytetradecanoyl]-β-D-glucopyranosyl]-L-serinamide triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serinamide hydrochloride, and (R)-3-hexanoyloxytetradecanoic acid: mp 184–185° C.; IR (film) 3416, 3284, 3210, 3096, 2954, 2923, 2853, 1735, 1721, 1680, 1664, 1646, 1560, 1466, 1246, 1169, 1080, 1038 cm$^{-1}$; $^1$H NMR (CDCl$_3$—CD$_3$OD) δ 0.90 (m, 18H), 1.1–1.7 (mH), 2.23–2.47 (m, 6H), 2.48–2.7 (m, 6H), 3.06 (q, 6H, J=6 Hz), 3.26–3.34 (mH), 3.66 (m, 1H), 3.77 (d, 1H, J=9.5 Hz), 3.82–3.96 (m, 2H), 4.12 (dd, 1H, J=2, 8 Hz), 4.21 (q, 1H, J=8 Hz), 4.56 (d, 1H, J=7 Hz), 4.61 (m, 1H), 5.05–5.18 (m, 3H), 5.24 (m, 1H), 7.26 (d, 1H, J=6.5 Hz), 7.40 (d, 1H, J=5.7 Hz).

Anal. Calcd. for $C_{75}H_{143}N_4O_{18}P\cdot H_2O$: C, 62.65 H, 10.16; N, 3.90; P, 2.15. Found: C, 62.60 H, 9.97; N, 3.72; P, 2.25.

EXAMPLE 31

B30

PREPARATION OF N-[(R)-3-DECANOYLOXYTETRADECANOYL]-O-[2-DEOXY-4-O-PHOSPHONO-2-[(R)-3-HEXANOYLOXYTETRADECANOYLAMINO]-3-O-[(R)-3-DECANOYLOXYTETRADECANOYL]-α-D-GLUCOPYRANOSYL]-L-SERINAMIDE TRIETHYLAMMONIUM SALT (COMPOUND (I), $R_1=R_3=N-C_9H_{19}CO$ $R_2=N-C_5H_{11}CO$, X=Y=O, N=M=P=Q=0, $R_4=R_5=R_7=R_9=H$, $R_6=CONH_2$, $R_8=PO_3H_2$).

In the same manner as described in Example 26 and cognate steps, N-[(R)-3-decanoyloxytetradecanoyl]-O-[2-deoxy-4-O-phosphono-2-[(R)-3-hexanoyloxytetradecanoylamino]-3-O-[(R)-3- decanoyloxytetradecanoyl]-(-D-glucopyranosyl]-L-serinamide triethylammonium salt was prepared from 2-(trimethylsilyl)ethyl 2-deoxy-4,6-O-isopropylidine-2-(2,2,2-trichloroethoxycarbonylarnino)-α-D-glucopyranoside, L-serinamide hydrochloride, and (R)-3-hexa- and decanoyloxytetradecanoic acids: mp 200–201° C. dec; IR (film) 3420, 3286, 2956, 2923, 2853, 1733, 1680, 1663, 1645, 1556, 1466, 1418, 1378, 1248, 1168, 1106, 1081, 1051 859, 722 cm$^{-1}$; $^1$H NMR (CDCl$_3$—CD$_3$OD) δ 0.88 (t, 18H, J=6.9 Hz), 1.0–1.7 (m, 103H), 2.15–2.71 (m, 12H), 3.06 (q, 6H, J=7 Hz), 3.68 (m, 1H), 3.87 (m, 1H), 4.09 (dd, 1H, J=10.8, 3.6 Hz), 3.35–4.0 (mH), 4.15–4.3 (m, 2H), 4.57–4.7 (m, 2H), 5.05–5.3 (m, 4H), 7.42 (m, 1H); $^{13}$C NMR (CDCl$_3$) δ 173.5, 173.1, 170.2, 169.8, 102.2, 75.8, 73.7, 71.3, 70.7, 70.2, 69.0, 60.7, 53.9, 51.7, 45.8, 41.3, 41.1, 39.1, 34.6, 34.5, 34.2, 32.0, 29.7, 32.0, 31.4, 29.8, 29.6, 29.5, 29.4, 25.6, 25.4, 25.1, 24.7, 22.7, 22.4, 13.9, 8.6.

Anal. Calcd. for $C_{83}H_{159}N_4O_{19}P \cdot H_2O$: C, 64.31; H, 10.47; N, 3.61. Found: C, 64.31; H, 10.27; N, 3.41.

EXAMPLE 32

B31

PREPARATION OF 2-[(R)-3-HEXANOYLOXYTETRADECANOYLAMINO]ETHYL 2-DEOXY-4-O-PHOSPHONO-3-O-[(R)-3-HEXANOYLOXYTETRADECANOYL]-2-[(R)-3-HEXANOYLOXYTETRADECANOYLAMINO]-α-D-GLUCOPYRANOSIDE TRIETHYLAMMONIUM SALT (COMPOUND (I), $R_1=R_2=R_3=N-C_5H_{11}CO$, X=Y=O, N=M=P=Q=0, $R_4=R_5=R_6=R_7=R_9=H$, $R_8=PO_3H_2$).

In the same manner as described in Example 21 and cognate steps, 2-[(R)-3-hexanoyloxytetradecanoylamino]ethyl 2-deoxy-4-O-phosphono-3-O-[(R)-3-hexanoyloxytetradecanoyl]-2-[(R)-3-hexanoyloxytetradecanoylamino]-α-D-glucopyranoside triethylammonium salt was prepared from 2-(trimethylsilyl)ethyl 2-deoxy-4,6-O-isopropylidine-2-(2,2,2-trichloroethoxycarbonylamino)-α-D-glucopyranoside, 2-amino-1-(t-butyldiphenylsilyloxy)ethane, and (R)-3-hexanoyloxytetradecanoic acid: mp 161–162° C.; IR (film) 3288, 3096, 2956, 2924, 2854, 1732, 1657, 1645, 1557, 1466, 1378, 1316, 1245, 1173, 1080, 1041 cm$^{-1}$; $^1$H NMR (CDCl$_3$—CD$_3$OD) δ 0.89 (m, 18H), 1.15–1.67 (m, 87H), 2.23–2.70 (m, 15H), 3.06 (q, 6H, J=7.4 Hz), 3.2–3.85 (n, 9H), 4.52 (d, 1H, J=8.0 Hz), 5.05–5.27 (m, 4H), 7.24 (d, 1H, J=8.5 Hz), 7.43 (br t, 1H); $^{13}$C NMR (CDCl$_3$) δ 173.7, 173.3, 173.3, 170.6, 170.2, 169.9, 100.9, 75.6, 73.0, 71.3, 70.9, 70.6, 68.3, 60.7, 55.0, 45.8, 41.6, 41.2, 39.5, 34.5, 34.4, 34.4, 31.9, 31.3, 29.7, 29.4, 25.4, 24.7, 22.7, 22.4, 14.1, 8.6.

Anal. Calcd. for $C_{74}H_{142}N_3O_{17}P \cdot H_2O$: C, 63.72; H, 10.40; N, 3.01; P, 2.22. Pound: C, 63.72; H, 10.21; N, 2.96; P, 2.46.

EXAMPLE 33

B32

PREPARATION OF 2-[(R)-3-HEXADECANOYLOXYTETRADECANOYLAMINO]ETHYL 2-DEOXY-4-O-PHOSPHONO-2-[(R)-3-OCTADECANOYLOXYTETRADECANOYLAMINO]-3-O-[(R)-3-TETRADECANOYLOXYTETRADECANOYL]-α-D-GLUCOPYRANOSIDE TRIETHYLAMMONIUM SALT (COMPOUND (I), $R_1=C_{13}H_{27}CO$, $R_2=C_{17}H_{35}CO$, $R_3=N-C_{15}H_{31}CO$, X=Y=O, N=M=P=Q=0, $R_4=R_5=R_6=R_7=R_9=H$, $R_8=PO_3H_2$).

In the same manner as described in Example 21 and cognate steps, 2-[(R)-3-hexadecanoyloxytetradecanoylamino]ethyl 2-deoxy-4-O-phosphono-2-[(R)-3-octadecanoyloxytetradecanoylanino]-3-O-[(R)-3-tetradecanoyloxytetradecanoyl]-α-D-glucopyranoside triethylammonium salt was prepared from 2-(trimethylsilyl)ethyl 2-deoxy-4,6-O-isopropylidine-2-(2,2,2-trichloroethoxycarbonylamino)-α-D-glucopyranoside, 2-amino-1-(t-butyldiphenylsilyloxy)ethane, and (R)-3-tetra-, octa- and hexadecanoyloxytetradecanoic acids: mp 180–181° C.; IR (film) 3284, 3097, 2920, 2851, 1731, 1657, 1699, 1683, 1653, 1558, 1541, 1521, 1506, 1467, 1435, 1418, 1376, 1258, 1173, 1033 cm$^{-1}$; $^1$H NMR (CDCl$_3$—CD$_3$OD) δ 0.8–1.75 (mH), 2.2–2.7 (mH), 3.08 (q, 6H, J=7.2 Hz), 3.2–3.5 (m, 5H), 3.55–4.05 (mH), 4.24 (q, 1H, J=7 Hz), 4.53 (d, 1H, J=8 Hz), 5.05–5.3 (m, 4H), 7.32 (d, 1H, J=9 Hz), 7.49 (br t, 1H); $^{13}$C NMR (CDCl$_3$) δ 173.8, 173.4, 173.3, 170.6, 170.3, 169.9, 100.9, 75.7, 73.0, 71.3, 70.9, 70.6, 68.3, 60.7, 55.0, 45.8, 41.3, 39.5, 34.6, 34.4, 32.0, 29.8, 29.4, 25.4, 25.1, 22.7, 14.2, 8.6.

Anal. Calcd. for $C_{104}H_{202}N_3O_{17}P \cdot 4H_2O$: C, 66.81; H, 11.32; N, 2.25. Found: C, 66.52; H, 10.80; N, 2.19.

EXAMPLE 34

B34

PREPARATION OF N-[(R)-3-HEXANOYLOXYTETRADECANOYL]-O-[2-DEOXY-4-O-PHOSPHONO-2-[(R)-3-HEXANOYLOXYTETRADECANOYLAMINO]-3-O-[(R)-3-HEXANOYLOXYTETRADECANOYL]-α-D-GLUCOPYRANOSYL]-L-SERINE TRIETHLAMMONIUM SALT. (COMPOUND (I), $R_1=R_2=R_3=N-C_5H_{11}CO$, X=Y=O, N=M=P=Q=0, $R_4=R_5=R_7=R_9=H$, $R_6=CO_2H$, $R_8=PO_3H_2$).

In the same manner as described in Example 16 and cognate steps, N-[(R)-3-hexanoyloxytetradecanoyl]-O-[2-deoxy-4-O-phosphono-2-[(R)-3-hexanoyloxytetradecanoylamino]-3-O-[(R)-3-hexanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexanoyloxytetradecanoic acid: mp 159–160° C.; IR (film) 3317, 2954, 2924, 2854, 1734, 1654, 1540, 1466, 1377, 1316, 1245, 1173, 1082, 846, 722 cm$^{-1}$; $^1$H NMR (CDCl$_3$—CD$_3$OD) δ 0.88 (m, 18H), 1.15–1.7 (mH), 2.2–2.75 (m, 12H), 3.08 (q, 6H, J=7.2 Hz), 3.40 (d, 1H, J=9.9 Hz), 3.55–3.95 (mH), 4.15–4.3 (m, 1H), 4.51 (d, 1H, J=8.0 Hz), 4.63 (br. s, 1H), 5.1–5.3 (m, 4H), 7.01 (d, 1H, J=9.1 Hz), 7.37 (d, 1 H, J=8.8 Hz); 13C NMR (CDCl$_3$) δ 177.0, 173.2, 173.2, 172.7, 172.3, 169.6, 169.0, 101.5, 75.0, 71.2, 70.9, 70.8, 69.1, 60.5, 53.1, 51.4, 46.1, 41.4, 41.0, 39.1, 34.5, 34.2, 34.1, 34.0, 31.9, 31.4, 31.3, 29.8, 29.6, 29.4, 25.6, 25.3, 25.1, 24.7, 24.7, 22.7, 22.5, 22.4, 14.1, 14.0, 8.7.

Anal. Calcd. for $C_{75}H_{142}N_3O_{19}P \cdot 2H_2O$: C, 61.83; H, 10.10; N, 2.88; P, 2.13. Found: C, 62.07; H, 10.01; N, 2.94; P, 2.40.

EXAMPLE 35

B35

PREPARATION OF N-[(R)-3-DECANOYLOXYTETRADECANOYL]-O-[2-DEOXY-4-O-PHOSPHONO-2-[(R)-3-DECANOYLOXYTETRADECANOYLAMINO]3-O-[(R)-3-HEXANOYLOXYTETRADECANOYL]-α-D-GLUCOPYRANOSYL]-L-SERINE TRIETYLAMMONIUM SALT. (COMPOUND (I), $R_1=N-C_5H_{11}CO$, $R_2=R_3=N-C_9H_{19}CO$, X=Y=O, N=M=P=Q=0, $R_4=R_5=R_7=R_9=H$, $R_6=CO_2H$, $R_6=PO_3H_2$).

In the same manner as described in Example 16 and cognate steps, N-[(R)-3-decanoyloxytetradecanoyl]-O-[2- deoxy-4-O-phosphono-2-[(R)-3-decanoyloxytetradecanoylamino]-3-O-[(R)-3-hexanoyloxytetradecanoyl]-α-D-glucopyranosyl]-L-serine triethylammonium salt was prepared from 2-(trimethylsilyl) ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 158–159° C.; IR (film) 3304, 2956, 2923, 2853, 1732, 1658, 1547, 1466, 1378, 1317, 1246, 1174, 1082, 960, 846, 722 cm$^{-1}$; $^1$H NMR (CDCl$_3$—CD$_3$OD) δ 0.88 (m, 18H), 1.15–1.7 (mH), 2.2–2.75 (m, 12H), 3.06 (q, 6H, J=7.2 Hz), 3.3–3.63 (mH), 3.66–3.98 (m, 4H), 4.1–4.3 (m, 2H), 4.54 (d, 1H, J=8.0 Hz), 4.6 (m, 1H), 5.05–5.27 (m, 4H), 7.15 (d, 1H, J=8.7 Hz), 7.46 (d, 1H, J=8.2 Hz); $^{13}$C NMR (CDCl$_3$) δ 173.6, 173.3, 172.8, 172.1, 169.6, 169.2, 101.5, 74.8, 70.9, 70.8, 69.3, 60.5, 53.2, 51.5, 46.1, 41.9, 41.5, 41.0, 39.2, 34.5, 34.3, 34.1, 31.9, 31.4, 29.8, 29.6, 29.4, 25.6, 25.3, 25.1, 25.1, 25.0, 24.8, 22.7, 22.5, 14.1, 11.1, 8.7.

Anal. Calcd. for C$_{83}$H$_{158}$N$_3$O$_{19}$P.H$_2$O: C, 64.27;H, 10.40; N, 2.71; P, 2.00. Found: C, 64.14;H, 10.33; N, 2.70; P, 2.05.

EXAMPLE 36

B36

PREPARATION OF N-[(R)-3-DECANOYLOXYTETRADECANOYL]-O-[2-DEOXY-4-O-PHOSPHONO-2-[(R)-3-HEXANOYLOXYTETRADECANOYLAMINO]-3-O-[(R)-3-DECANOYLOXYTETRADECANOYL]-α-D-GLUCOPYRANOSYL]-L-SERINE TRIETHYLAMMONIUM SALT. (COMPOUND (I), R$_1$=R$_3$=N—C$_9$H$_{19}$CO, R$_2$=N—C$_5$H$_{11}$CO, X=Y=O, N=M=P=Q=0, R$_4$=R$_5$=R$_7$=R$_9$=H, R$_6$=CO$_2$H, R$_8$=PO$_3$H$_2$).

In the same manner as described in Example 16 and cognate steps, N- [(R)-3-decanoyloxytetradecanoyl]-O-[2-deoxy-4-O-phosphono-2-[(R)-3-hexanoyloxytetradecanoylamino]-3-O-[(R)-3-decanoyloxytetradecanoyl]-α-D-glucopyranosyl]-L-serine triethylammonium salt was prepared from 2-(trimethylsilyl) ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 157–158° C.; IR (film) 3306, 2955, 2924, 2853, 1734, 1657, 1545, 1466, 1378, 1245, 1170, 1081, 954, 842, 722 cm$^{-1}$; $^1$H NMR (CDCl$_3$—CD$_3$D) δ 0.88 (m, 18H), 1.15–1.7 (mH), 2.2–2.75 (m, 12H), 3.06 (q, 6H, J=7.2 Hz), 3.36 (d, 1H, J=9.8 Hz), 3.43–3.63 (mH), 3.68–3.95 (m, 4H), 4.13–4.27 (m, 2H), 4.54 (d, 1H, J=8.3 Hz), 4.6 (m, 1H), 5.08–5.27 (m, 4H); $^{13}$C NMR (CDCl$_3$) δ 176.9, 173.4, 173.2, 172.8, 172.2, 169.5, 169.1, 101.4, 74.8, 71.1, 70.9, 70.8, 69.3, 53.2, 51.6, 46.1, 41.8, 41.4, 41.0, 39.2, 34.5, 34.4, 34.3, 34.1, 34.0, 32.0, 31.4, 29.8, 29.6, 29.4, 29.3, 25.6, 25.3, 25.2, 25.1, 24.8, 22.7, 22.4, 14.1, 14.0, 8.7.

Anal. Calcd. for C$_{83}$H$_{158}$N$_3$O$_{19}$P.H$_2$O: C, 64.27;H, 10.40; N, 2.71; P, 2.00. Found: C, 64.09;H, 10.31; N, 2.70; P, 2.06.

EXAMPLE 37

B37

PREPARATION OF N-[(R)-3-HEXANOYLOXYTETRADECANOYL]-O-[2-DEOXY-4-O-PHOSPHONO-2-[(R)-3-DECANOYLOXYTETRADECANOYLAMINO]-3-O-[(R)-3-DECANOYLOXYTETRADECANOYL]-α-D-GLUCOPYRANOSYL]-L-SERINE TRIETHYLAMMONIUM SALT. (COMPOUND (I), R$_1$=R$_2$=N—C$_9$H$_{19}$CO R$_3$=N—C$_5$H$_{11}$CO, X=Y=O, N=M=P=Q=0, R$_4$=R$_5$=R$_7$=R$_9$=H, R$_6$=CO$_2$H, R$_8$=PO$_3$H$_2$).

In the same manner as described in Example 16 and cognate steps, N-[(R)-3-hexanoyloxytetradecanoyl]-O-[2-deoxy-4-O-phosphono-2-[(R)-3-decanoyloxytetradecanoylamino]-3-O-[(R)-3-decanoyloxytetradecanoyl]-α-D-glucopyranosyl]-L-serine triethylammonium salt was prepared from 2-(trimethylsilyl) ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 156–157° C. dec; IR (film) 3306, 2956, 2923, 2852, 1732, 1659, 1545, 1466, 1378, 1246, 1173, 1081, 958, 847, 722 cm$^{-1}$; $^1$H NMR (CDCl$_3$—CD$_3$OD) δ 0.88 (m, 18H), 1.0–1.7 (mH), 2.2–2.75 (m, 12H), 2.9–3.3 (mH), 3.06 (q, overlaps preceding multiplet, J=7.2 Hz), 3.36 (d, 1H, J=9.6 Hz), 3.43–3.63 (mH), 3.63–3.95 (m, 4H), 4.21 (m, 2H), 4.53 (d, 1H, J=8.0 Hz), 4.6 (br s, 1H), 5.06–5.28 (m, 4H); 13C NMR (CDCl$_3$) δ 176.3, 173.6, 173.3, 172.8, 172.1, 169.6, 169.2, 101.5, 74.8, 70.9, 70.9, 69.4, 60.5, 53.2, 51.5, 46.1, 41.9, 41.5, 41.1, 39.2, 34.6, 34.5, 34.4, 34.1, 31.9, 31.3, 29.8, 29.7, 29.6, 29.5, 29.4, 29.3, 25.6, 25.3, 25.2, 24.7, 22.7, 22.4, 14.1, 14.0, 11.1, 8.7.

Anal. Calcd. for C$_{83}$H$_{158}$N$_3$O$_{19}$P.H$_2$O: C, 64.27;H, 10.40; N, 2.71. Found: C, 64.29;H, 10.30; N, 2.61.

EXAMPLE 38

B38

PREPARATION OF N-[(R)-3-HEXANOYLOXYTETRADECANOYL]-O-[2-DEOXY-4-O-PHOSPHONO-2-[(R)-3-HEXANOYLOXYTETPADECANOYLAMINO]-3-O-[(R)-3-DECANOYLOXYTETRADECANOYL]-α-D-GLUCOPYRANOSYL]-L-SERINE TRIETHYLAMMONIUM SALT. (COMPOUND(I), R$_1$=N—C$_9$H$_{19}$CO, R$_2$=R$_3$=N—C$_5$H$_{11}$CO, X=Y=O, N=M=P=Q=0, R$_4$=R$_5$=R$_7$=R$_9$=H, R$_6$=CO$_2$H, R$_8$=PO$_3$H$_2$).

In the same manner as described in Example 16 and cognate steps, N-[(R)-3-hexanoyloxytetradecanoyl]-O-[2-deoxy-4-O-phosphono-2-[(R)-3-hexanoyloxytetradecanoylamino]-3-O-[(R)-3-decanoyloxytetradecanoyl]-α-D-glucopyranosyl]-L-serine triethylammonium salt was prepared from 2-(trimethylsilyl) ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 152–153° C. dec; IR (film) 3307, 2956, 2924, 2853, 1734, 1658, 1544, 1466, 1378, 1316, 1245, 1173, 1081, 955, 843, 722 cm$^{-1}$; $^1$H NMR (CDCl$_3$—CD$_3$OD) δ 0.88 (m, 18H), 1.15–1.7 (mH), 2.2–2.75 (m, 12H), 3.06 (q, 6H, J=7.2 Hz), 3.28–3.55 (mH), 3.67–3.97 (m, 4H), 4.13–4.27 (m, 2H), 4.55 (d, 2H, J=7.2 Hz), 4.60 (m, 1H), 5.08–5.28 (m,4H), 7.11 (d, 1H, J=8.7 Hz), 7.42 (d, 1H, J=8.0 Hz); $^{13}$C NMR (CDCl$_3$) δ 176.9, 173.5, 173.2, 172.8, 172.2, 169.5, 169.1, 101.4, 74.8, 71.1, 70.9, 70.8, 69.3, 60.5, 53.2, 51.5, 46.1, 41.8, 41.4, 41.1, 39.2, 34.5, 34.3, 34.2, 34.1, 34.0, 31.9, 31.7, 31.4, 31.3, 29.8, 29.6, 29.4, 29.3, 25.6, 25.3, 25.2, 24.7, 22.7, 22.4, 14.1, 14.0, 11.1, 8.7.

Anal. Calcd. for C$_{79}$H$_{150}$N$_3$O$_{19}$P: C, 64.24;H, 10.24; N, 2.85. Found: C, 64.06;H, 10.35; N, 2.88.

EXAMPLE 39

B39

PREPARATION OF N-[(R)-3-HEXANOYLOXYTETRADECANOYL]-O-[2-DEOXY-4-O-PHOSPHONO-2-[(R)-3-DECANOYLOXYETRADECANOYLAMINO]-3-O-[(R)-3-HEXANOYLOXYTETRADECANOYL]-α-D-GLUCOPYRANOSYL]-L-SERINE TRIETHYLAMMONIUM SALT. (COMPOUND (I), R$_1$=R$_3$=N—C$_5$H$_{11}$CO, R$_2$=N—C$_9$H$_{19}$CO, X=Y=O, N=M=P=Q=0, R$_4$=R$_5$=R$_7$=R$_9$=H, R$_6$=CO$_2$H, R$_8$=PO$_3$H$_2$).

In the same manner as described in Example 16 and cognate steps, N-[(R)-3-hexanoyloxytetradecanoyl]-O-[2- deoxy-4-O-phosphono-2-[(R)-3-decanoyloxytetradecanoylamino1-3-O-[(R)-3-hexanoyloxytetradecanoyl]-α-D-glucopyranosyl]-L-serine triethylammonium salt was prepared from 2-(trimethylsilyl) ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 151–152° C. dec; IR (film) 3308, 2956, 2924, 2854, 1732, 1660, 1544, 1466, 1378, 1317, 1246, 1173, 1081, 957, 843, 722 cm$^{-1}$; $^1$H NMR (CDCl$_3$—CD$_3$OD) δ 0.88 (m, 18H), 1.0–1.7 (mH), 2.18–2.72 (m, 12H), 3.06 (q, 6H, J=7.4 Hz), 3.23–3.51 (mH), 3.66–3.98 (m, 4H), 4.12–4.28 (m, 2H), 4.55 (d, 1H, J=7.4 Hz), 4.60 (m, 1H), 5.05–5.28 (m, 4H), 7.10 (d, 1H, J=8.2 Hz), 7.43 (d, 1H, J=8.5 Hz); $^{13}$C NMR (CDCl$_3$) δ 176.9, 173.6, 173.2, 172.7, 172.2, 169.5, 169.0, 101.5, 75.0, 74.8, 71.2, 70.9, 70.8, 69.2, 60.5, 53.1, 51.5, 46.1, 41.8, 41.5, 41.1, 39.1, 34.6, 34.5, 34.2, 34.0, 32.0, 31.4, 31.3, 29.8, 29.7, 29.6, 29.4, 29.3, 25.6, 25.3, 25.1, 24.8, 24.7, 22.7, 22.5, 22.4, 14.1, 14.0, 11.1, 8.7.

Anal. Calcd. for C$_{79}$H$_{150}$N$_3$O$_{19}$P.H$_2$O: C, 63.47;H, 10.25; N, 2.81. Found: C, 63.63;H, 10.35; N, 2.84.

EXAMPLE 40

B40

PREPARATION OF N-[(R)-3-DECANOYLOXYTETRADECANOYL]-O-[2-DEOXY-4-O-PHOSPHONO-2-[(R)-3-HEXANOYLOXYTETRADECANOYLAMINO]-3-O-[(R)-3-HEXANOYLOXYTETRADECANOYL]-α-D-GLUCOPYRANOSYL]-L-SERINE TRETHYLAMMONIUM SALT. (COMPOUND (I), R$_1$=R$_3$=N—C$_5$H$_{11}$CO, R$_2$=N—C$_9$H$_{19}$CO, X=Y=O, N=M=P=Q=0, R$_4$=R$_5$=R$_7$=R$_9$=H, R$_6$=CO$_2$H, R$_8$=PO$_3$H$_2$).

In the same manner as described in Example 16 and cognate steps, N-[(R)-3-decanoyloxytetradecanoyl]-0-[2-deoxy-4-O-phosphono-2-[(R)-3-hexanoyloxytetradecanoylaamino]-3-O-[(R)-3-hexanoyloxytetradecanoyl]-α-D-glucopyranosyl]-L-serine triethylammonium salt was prepared from 2-(trimethylsilyl) ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 158–159° C.; IR (film) 3308, 2956, 2924, 2854, 1734, 1659, 1545, 1466, 1378, 1316, 1245, 1173, 1081, 956, 844, 722 cm$^{-1}$; $^1$H NMR (CDCl$_3$—CD$_3$OD) δ 0.8–1.0 (m, 18H), 1.15–1.73 (mH), 2.18–2.72 (m, 12 H), 3.06 (q, 6H, J=7.4 Hz), 3.35 (d, 1H, J=10 Hz), 3.47–3.67 (mH), 3.68–3.97 (m, 4H), 4.1–4.3 (m, 2H), 4.54 (d, 1H, J=8.0 Hz), 4.61 (m, 1H), 5.07–5.28 (m, 4H); $^{13}$C NMR (CDCl$_3$) δ 176.9, 173.5, 173.2, 172.8, 172.2, 169.6, 169.1, 101.5, 75.0, 74.8, 71.2, 70.9, 70.8, 69.2, 60.5, 53.2, 51.4, 46.1, 41.9, 41.5, 41.0, 39.2, 34.5, 34.2, 34.0, 31.9, 31.4, 29.8, 29.6, 29.4, 29.2, 25.6, 25.3, 25.1, 25.0, 24.8, 24.7, 22.7, 22.5, 22.4, 14.1, 14.0,11.1, 8.7.

Anal. Calcd. for C$_{79}$H$_{150}$N$_3$O$_{19}$P.H$_2$O: C, 63.47;H, 10.25; N, 2.81; P, 2.07. Found: C, 63.43;H, 10.22; N, 2.83; P, 2.13.

EXAMPLE 41

B41

PREPARATION OF 3-HYDROXY-(R)-2-[(R)-3-DECANOYLOXYETRADECANOYLAMINO] PROPYL 2-DEOXY-4-O-PHOSPHONO-2-[(R)-3-HEXANOYLOXYTETRADECANOYLAMINO]-3-O-[(R)-3-DECANOYLOXYTETRADECANOYL]-α-D-GLUCOPYRANOSIDE TRIETHYLAMMONIUM SALT (COMPOUND (I), R$_1$=R$_3$=N—C$_9$H$_{11}$CO, R$_2$=N—C$_5$H$_{11}$CO, X=Y=O, N=M=Q=0, R$_4$=R$_5$=R$_7$=R$_9$=H, R$_6$=OH, P=1 R$_8$=PO$_3$H$_2$).

In the same manner as described in Example 6 and cognate steps, 3-hydroxy-(R)-2-[(R)-3-decanoyloxytetradecanoylamino]propyl 2-deoxy-4-O-phosphono-2-[(R)-3-hexanoyloxytetradecanoylamino]-3-O-[(R)-3-decanoyloxytetradecanoyl]-α-D-glucopyranoside triethylammonium salt was prepared from N-(2,2,2-trichloroethoxycarbonylamino)-1,3,4,6-tetra-O-acetyl-2-deoxy-α-D-glucopyranoside, (S)-2-amino-3-benzyloxy-1-propanol, and (R)-3-hexa- and decanoyloxytetradecanoic acids: mp 151–153° C.; IR (film) 3287, 2956, 2923, 2853, 1732, 1643, 1552, 1466, 1378, 1318, 1147, 1176, 1108, 1082, 1052, 856, 722 cm$^{-1}$; $^1$NMR (CDCl$_3$—CD$_3$OD) δ 0.88 (t, 18H, J=6.9 Hz), 1.0–1.72 (mH), 2.17–2.71 (m, 12H), 2.9–3.3 (mH), 3.08 (q, overlaps preceding multiplet, J=7.2 Hz), 3.31 (d, 1H, J=9.6 Hz), 3.5–4.02 (m, 8H), 4.20 (d, 1H, J=9.5 Hz), 4.60 (d, 1H, J=8.0 Hz), 5.05–5.25 (m, 4H); $^{13}$C NMR (CDCl$_3$) δ 173.7, 173.5, 173.4, 170.6, 170.1, 101.1, 75.5, 73.0, 71.6, 71.3, 70.8, 70.5, 68.2, 61.4, 60.7, 54.8, 50.5, 45.8, 41.4, 39.4, 34.6, 34.5, 34.2, 31.9, 31.4, 29.8, 29.7, 29.5, 29.4, 29.3, 25.4, 25.1, 22.7, 22.4, 14.1, 14.0, 8.6.

Anal. Calcd. for C83H160N$_3$O$_{18}$P.H$_2$O: C, 64.84;H, 10.62; N, 2.55. Found: C, 65.01;H, 10.50; N, 2.55.

EXAMPLE 42

B42

PREPARATION OF 5-[2-DEOXY-4-O-PHOSPHONO-2-[(R)-3-DECANOYLOXYTETRADECANOYLAMINO]-3-O-[(R)-3-DECANOYLOXYTETRADECANOYL]-α-D-GLUCOPYRANOSYLOXY]-(S)-4-[(R)-3-DECANOYLOXYTETRADECANOYLAMINO] PENTANOIC ACID TRIETHYLAMMONIUM SALT (COMPOUND (I), R$_1$=R$_2$=R$_3$=N—C$_9$H$_{19}$CO, X=Y=O, N=M=Q=0, R$_4$=R$_5$=R$_7$=R$_9$=H, R$_6$=CO$_2$H, P=2, R$_5$=PO$_3$H$_2$).

(1) In the same manner described in Example 13-(5), benzyl (S)-4-(t-butyloxycarbonylamino)-5-hydroxypentanoate (0.338 g, 0.954 mmol) and the compound prepared in Example 15-(4) (1.15 g, 0.954 mmol) were coupled in the presence of AgOTf (1.22 g, 4.77 mmol) to give 0.70 g (50%) of benzyl (S)-4-(t-butyloxycarbonylamino)-5-[2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-α-D-glucopyranosyloxy) pentanoate: $^1$H NMR (CDCl$_3$) δ 0.88 (m, 6H), 1.0–2.05 (m, 55H), 2.12–2.5 (m, 6H), 3.28–3.90 (m, 5H), 4.26 (dd, 1H, J=4.5, 11.5 Hz), 4.38 (d, 1H, J=11.5 Hz), 4.57–4.98 (m, 5H), 5.11 (s, 2H), 5.18 (m, 1H), 5.49 (t, 1H, J=9 Hz), 5.78 (d, 1H, J=7.7 Hz), 7.04–7.45 (m, 15H).

(2) A solution of the compound prepared in (1) above (0.67 g, 0.45 mmol) in CH$_2$Cl$_2$ (5 mL) was cooled to 0° C., treated dropwise with TFA (70 FL), and stirred for 3 h at room temperature. The reaction mixture was diluted with CH$_2$Cl$_2$ (15 mL), washed with saturated aqueous NaHCO$_3$ and dried (Na$_2$SO$_4$). (R)-3-Decanoyloxytetradecanoic acid (0.20 g, 0.50 mmol) and EDC MeI (0.15 g, 0.5 mmol) were added and the resulting mixture was stirred for 16 h at room temperature. The reaction mixture was filtered through a pad of Celite® and concentrated. The crude product obtained was purified by flash chromatography on silica gel (gradient elution, 15→30% EtOAc-hexanes) to give 0.36 g (45%) of benzyl (S)-4-[(R)-3-decanoyloxytetradecanoylamino]-5-[2-deoxy-4-O-diphenylphosphono-3-O-[(R)-3-decanoyloxytetradecanoyl]-6-O-(2,2,2-trichloro-1,1- dimethylethoxycarbonyl)-2-(2,2,2-trichloroethoxycarbonylamino)-α-D-glucopyranosyloxy] pentanoate: $^1$H NMR (CDCl$_3$) δ 0.89 (m, 12H), 1.0–1.978 (mH), 2.12–2.5 (m, 10H), 3.45–3.65 (m, 2H), 3.79 (dd, 2H, J=3.8, 10 Hz), 4.06 (m, 1H), 4.27 (dd, 1H, J=4.9, 12 Hz), 4.35 (d, 1H, J=12 Hz), 4.6–4.8 (m, 3H), 4.83 (d, 1H, J=8.3 Hz), 5.10 (s, 2H), 5.17 (m, 2H), 5.48 (t, 1H, J=10 Hz), 5.79 (d, 1H, J=7.7 Hz), 6.05, (d, 1H, J=8.8 Hz), 7.07–7.42 (m, 15H).

(3) In the same manner as described for the preparation of compound B14 from the compound prepared in Example 15-(5), 5-[2-deoxy-4-O-phosphono-2-[(R)-3-decanoyloxytetradecanoylaminol-3-O-[(R)-3-decanoyloxytetradecanoyl]-α-D-glucopyranosyloxy]-(S)-4-[(R)-3-decanoyloxytetradecanoylamino]pentanoic acid triethylammonium salt was prepared from the compound prepared in (2) above: mp 184–188° C; IR (film) 3284, 2955, 2919, 2848, 1730, 1654, 1548, 1459, 1374, 1259, 1165, 1081, 1032, 800 cm$^{-1}$; $^1$H NMR (CDCl$_3$—CD$_3$OD) δ 0.88 (t, 18H, J=7 Hz), 1.0–2.0 (mH), 2.18–2.75 (m, 12H), 3.08 (q, 6H, J=7.4 Hz), 3.33–4.42 (mH), 4.44 (d, 1 H, J=8.5 Hz), 5.02–5.31 (m, 4H), 7.54 (d, 1H, J=8 Hz), ),7.61 (d, 1H, J=7 Hz); $^{13}$C NMR (CDCl$_3$) δ 176.8, 173.6, 173.3, 170.8, 170.2, 101.1, 75.1, 73.7, 71.7, 71.1, 70.8, 70.1, 60.8, 54.1, 48.8, 45.9, 41.4, 41.2, 39.4, 34.5, 34.4, 34.1, 31.9, 31.3, 29.8, 29.7, 29.6, 29.5, 29.4, 26.9, 25.5, 25.3, 25.1, 22.7, 14.1, 8.6.

Negative FAB-MS calcd for [M-H]$^-$ 1514.0889, found 1514.0816.

EXAMPLE 43

B43

PREPARATION OF N-[(R)-3-HYDROXYTETRADECANOYL]-O-[2-DEOXY-4-O-PHOSPHONO-2-[(R)-3-DODECANOYLOXYTETRADECANOYLAMINO]-3-O-[(R)-3-TETRADECANOYLOXYTETRADECANOYL]-α-D-GLUCOPYRANOSYL]-L-SERINE TRIETHYLAMMONIUM SALT. (COMPOUND (I), R$_1$=N—C$_{13}$H$_{27}$CO, R$_2$=N—C$_{11}$H$_{23}$CO, R$_3$=H, X=Y=O, N=M=P=Q=0, R$_4$=R$_5$=R$_7$=R$_9$=H, R$_6$=CO$_2$H, R$_8$=PO$_3$H$_2$).

(1) In the same manner described in Example 13-(5), N-allyloxycarbonyl-L-serine benzyl ester (0.225 g, 0.806 mmol) and the compound prepared in Example 22-(2) (1.104 g, 0.886 mmol) were coupled in the presence of AgOTf (0.828 g, 3.22 mmol) to give 1.01 g (83%) of N-allyloxycarbonyl-O-[2-deoxy- 4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranosyl]-L-serine benzyl ester: $^1$H NMR (CDCl$_3$) δ 0.88 (m, 6H), 1.0–1.7 (m, 42H), 1.78 (s, 3H), 1.86 (s, 3H), 2.12–2.48 (m, 4H), 3.26 (m, 1H), 3.66 (m, 1H), 3.80(dd, 1H, J=3, 10 Hz),4.19–4.38(m,4H),4.48–4.85(m,6H),4.98 (d, 1H, J=7.7 Hz), 5.08–5.38 (m, 5H), 5.49 (m, 1H), 5.60–5.75 (m, 2H), 5.82–6.0 (m, 1H), 7.06–7.42 (m, 15H).

(2) A solution of the compound prepared in (1) above (1.01 g, 0.68 mmol) and diethyl malonate (1.50 g, 9.48 mmol) in THF was degassed with argon (1 h), treated with tetrakis(triphenylphosphine)palladium(0) (0.10 g, 0.09 mmol), and stirred overnight at room temperature. The reaction mixture was filtered through a pad of silica with 2% MeOH—CHCl$_3$ and the filtrate concentrated. A solution of the crude amine obtained in CH$_2$Cl$_2$ (20 mL) was treated with (R)-3-hydroxytetradecanoic acid (0.18 g, 0.75 mmol) and EDCMeI (0.66 g, 1.02 mmol), stirred overnight at room temperature, and then concentrated. The crude product obtained was purified by flash chromatography on silica gel (gradient elution, 30→40% EtOAc-hexanes) to give 0.506 g (46%) of N-[(R)-3-hydroxytetradecanoyl]-O-[2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranosyl]-L-serine benzyl ester: $^1$H NMR (CDCl$_3$) δ 0.88 (m, 9H), 1.0–1.7 (m, 62H), 1.79(s,3H), 1.87 (s,3H),2.19(t,2H, J=7 Hz),2.3–2.5 (m, 4H),3.1 (brs, 1 H), 3.55 (q, 1H, J=9 Hz), 4.0–4.43 (m, 5H), 4.56–4.85 (m, 4H), 5.13–5.32 (m, 4H), 6.59 (d, 1H, J=7.4 Hz), 6.83 (br s, 1H), 7.17–7.41 (m, 15H).

(3) In the same manner as described for the preparation of compound B12 from the compound prepared in Example 13-(5), N-[(R)-3-hydroxytetradecanoyl]-O-[2-deoxy-4-O-phosphono-2-[(R)-3-dodecanoyloxytetradecanoyl amino]-3-O-[(R)-3-tetradecanoyloxytetradecanoyl]-α-D-glucopyranosyl]-L-serine triethylammonium salt was prepared from the compound prepared in (2) above: mp 170–173° C. dec; R (film) 3313, 2955, 2923, 2853, 1734, 1662, 1655, 1558, 1541, 1467, 1458, 1376, 1248, 1166, 1108, 1078, 1049, 953, 942, 842 cm$^{-1}$; $^1$H NMR (CDCl$_3$—CD$_3$OD) δ 0.88 (m, 18H), 1.15–1.7 (mH), 2.2–2.75(m, 12H), 3.06 (q, 6H, J=7.2 Hz), 3.3–3.63 (mH), 3.66–3.98 (m, 4H), 4.1–4.3 (m, 2H), 4.54 (d, 1H, J=8.0 Hz), 4.6 (m, 1H), 5.05–5.27 (m, 4H), 7.15 (d, 1H, J=8.7 Hz), 7.46 (d, 1H, J=8.2 Hz); $^{13}$C NMR (CDCl$_3$) δ 177.0, 173.3, 172.8, 172.3, 171.9, 169.2, 101.2, 74.9, 74.8, 74.3, 70.8, 70.6, 69.3, 68.4, 59.9, 53.1, 51.5, 42.5, 41.5, 39.2, 37.1, 34.6, 34.4, 34.3, 34.1, 32.0, 29.8, 29.4, 25.6, 25.2, 22.7, 22.5, 14.5, 8.7.

Anal. Calcd. for C$_{83}$H$_{160}$N$_3$O$_{18}$P.2H$_2$O: C, 64.10;H, 10.63; N, 2.70; P, 1.99. Found: C, 64.28;H, 10.42; N, 2.70; P, 1.84.

TEST EXAMPLE 1

STIMULATION OF ANTI-TETANUS TOXOID ANTIBODY PRODUCTION

The AGPs of the subject invention enhanced antibody production to purified tetanus toxoid in a murine model. Ten mg of each AGP sample was added to 1 ml of an oil-lecithin mixture containing squalene oil plus 12% lecithin. The mixtures were heated in a 56° C. water bath and sonicated to achieve clear solutions. Fifty (50) μof each solution was emulsified by vortexing in 2 ml of sterile, pre-warned 0.1% Tween 80 saline containing 1.0 μg tetanus toxoid antigen/ml. Preparations were vortexed again just prior to administration to mice. Female C57BL/6 x DBA/2 F$_1$ mice (8 per group) were treated with 0.2 ml of the appropriate preparation distributed as a 0.1 ml subcutaneous injection into each flank. The final mouse dosage of the tetanus toxoid and AGP compounds was 0.2 μg and 50 μg, respectively. Control mice received tetanus toxoid in vehicle (oil-Tween saline). All mice were treated on day 0 followed by a second immunization on day 21. Fourteen days following the second immunization mice were bled and sera were isolated by centrifugation.

Serum samples from each mouse were evaluated for anti-tetanus toxoid antibodies by enzyme immunoassay (EIA) analysis using tetanus toxoid coated rnicrotiter plates. Anti-tetanus antibody titers were evaluated for IgM, total Ig, as well as, IgG$_1$, IgG$_{2a}$ and IgG$_{2b}$ isotypes. Each serum sample was diluted 2-fold for eleven dilutions starting with an initial serum dilution of 1:200. Results are shown in Tables 2–4.

TABLE 2

Anti-tetanus toxoid antibody titers of treated mice.

| | Total IgG | | IgG$_1$ | | IgG$_{2a}$ | | IgG$_{2b}$ | | IgM |
|---|---|---|---|---|---|---|---|---|---|
| Material | T/C* | Titer | T/C | Titer | T/C | Titer | T/C | Titer | T/C | Titer |
| B11 | 3.6 | 23,200 | 1.86 | 400,000 | 2.06 | 10,450 | 0.93 | 26,800 | 4.75 | 7,600 |
| B2 | 3.84 | 24.800 | 2.16 | 464,000 | 4.28 | 21,700 | 1.57 | 45,200 | 4.50 | 7,200 |
| B1 | 3.97 | 25,600 | 3.42 | 736,000 | 3.78 | 19,200 | 2.45 | 70,400 | 2.38 | 3,800 |
| B25 | 8.93 | 57,600 | 2.68 | 576,000 | 1.67 | 8,500 | 3.28 | 94,400 | 2.0 | 3,200 |
| B21 | 4.71 | 30,400 | 2.23 | 480,000 | 5.83 | 29,600 | 6.07 | 174,400 | 5.50 | 8,800 |
| B15 | 18.85 | 121,600 | 4.17 | 896,000 | 6.80 | 34,500 | 2.79 | 80,256 | 4.0 | 6,400 |
| Vehicle | | 6,450 | | 215,000 | | 5,075 | | 28,750 | | 1,600 |

*T/C Ratio = Experimental Test Titer ÷ Vehicle Control Titer.

TABLE 3

Anti-tetanus toxoid antibody titers of treated mice.

| Material | T/C* | IgM | T/C | IgG$_{2a}$ | T/C | IgG$_{2b}$ |
|---|---|---|---|---|---|---|
| B12 | 3.1 | 4800 | 139.4 | 2370 | 149 | 9840 |
| B16 | 1.6 | 2560 | 66.8 | 1135 | 104 | 6880 |
| B13 | 3.9 | 6080 | 220 | 3740 | >208 | >13,760 |
| B11 | 3.3 | 5120 | 347 | 5900 | 127.3 | 8400 |
| Vehicle | — | 1760 | — | 25 | — | 98 |

*T/C Ratio = Experimental Test Titers ÷ Vehicle Control Titers

TABLE 4

Anti-tetanus toxoid antibody titers of treated mice.

| | Total Ig | | IgM | | IgG$_1$ | | IgG$_{2a}$ | | IgG$_{2b}$ | |
|---|---|---|---|---|---|---|---|---|---|---|
| Material | T/C | Titer | T/C | Titer | T/C | Titer | T/C | Titer | T/C | Titer |
| B26 | 10.5 | 2,490 | 1.1 | 600 | 16.9 | 25,200 | 29.3 | 440 | 42.6 | 2,260 |
| B15 | 144.5 | 34,400 | 2.7 | 1,520 | 118.3 | 176,000 | 259.3 | 3,890 | 603.8 | 32,000 |
| B22 | 60.0 | 19,050 | 0.8 | 440 | 18.4 | 27,400 | 345.8 | 5,187 | 59.6 | 3,160 |
| B28 | 228.6 | 54,500 | 3.7 | 2,080 | 92.5 | 137,600 | 664.7 | 9,970 | 519.2 | 27,520 |
| Vehicle | | 238 | | 560 | | 1,488 | | 15 | | 53 |

*T/C Ratio = Experimental Test Titers ÷ Vehicle Control Titer.

Compounds of the subject invention showed a dose response when administered with tetanus toxoid. BFD1 (C57B1/6 X DBA/2) female mice (8 per group) were immunized with 0.2 ml of emulsions containing AGP+0.2 μg of tetanus toxoid. A second immunization was administered 21 days post primary immunization. Each mouse was bled 21 days after the second injection. The results are shown in Tables 5 and 6.

TABLE 5

Dose response of AGPs in mice immunized with tetanus toxoid.

| | Total Ig | | IgM | | IgG$_1$ | | IgG$_{2a}$ | | IgG$_{2b}$ | |
|---|---|---|---|---|---|---|---|---|---|---|
| Material | T/C Ratio* | Titer | T/C Ratio | Titer | T/C Ratio | Titer | T/C Ratio | Titer | T/C Ratio | Titer |
| B15 50 μg | 3.3 | 7,000 | 13.4 | 37,600 | 4.1 | 26,300 | 150.0 | 11,225 | 3.2 | 2500 |
| B15 25 μg | 5.8 | 12,400 | 2.1 | 6,000 | 4.5 | 28,800 | 52.0 | 3900 | 7.0 | 5400 |
| B15 10 μg | 5.3 | 11,450 | 1.4 | 4,000 | 5.5 | 35,100 | 33.8 | 2538 | 9.9 | 7650 |
| B27 50 μg | 3.2 | 6,800 | 4.0 | 11,200 | 1.6 | 10,400 | 12.0 | 900 | 11.6 | 9,000 |
| Vehicle | | 2150 | | 2800 | | 6350 | | 75 | | 775 |

*T/C Ratio = Experimental Test Titer ÷ Vehicle Control Titer.

TABLE 6

Dose response of AGPs in mice immunized with tetanus toxoid.

| | IgM | | Total Ig | | IgG$_1$ | | IgG$_{2a}$ | | IgG$_{2b}$ | |
|---|---|---|---|---|---|---|---|---|---|---|
| Material | T/C* | Titer | T/C | Titer | T/C | Titer | T/C | Titer | T/C | Titer |
| B12 50 μg | 5.43 | 869 | 368.55 | 47,543 | 141.22 | 259,429 | | nd | 499.35 | 12,983 |
| B12 25 μg | 3.14 | 503 | 403.98 | 52,114 | 145.21 | 266,743 | 16.86 | 354 | 196.92 | 5,120 |
| B12 10 μg | 3.71 | 594 | 248.06 | 32,000 | 81.12 | 149,029 | 6.81 | 143 | 181.12 | 4,709 |
| B12 5 μg | 3.43 | 549 | 489.92 | 63,200 | 84.11 | 154,514 | 34.14 | 717 | 352.54 | 9,166 |
| B12 1 μg | 1.71 | 274 | 326.02 | 42,057 | 90.08 | 165,486 | 73.71 | 1,548 | 175.81 | 4,571 |
| B15 50 μg | 3.14 | 503 | 233.88 | 30,171 | 90.08 | 165,486 | 50.05 | 1,051 | 235.62 | 6,126 |
| B15 25 μg | 2.29 | 366 | 181.91 | 23,467 | 106.14 | 194,971 | 10.43 | 219 | 158.23 | 4,114 |
| B15 10 μg | 2.86 | 457 | 170.10 | 21,943 | 39.07 | 71,771 | 2.57 | 54 | 84.38 | 2,194 |
| B15 5 μg | 1.71 | 274 | 248.06 | 32,000 | 103.15 | 189,486 | 3.00 | 63 | 210.88 | 5,483 |
| B15 1 μg | 1.57 | 251 | 166.56 | 21,486 | 72.04 | 132,343 | 7.62 | 160 | 114.27 | 2,971 |
| Vehicle | | 160 | | 129 | | 1837 | | 21 | | 26 |

*T/C = Experimental Test Titer ÷ Vehicle Control Titer.
nd—not done

TEST EXAMPLE 2

STIMULATION OF ANTIOVALBUMIN ANTIBODY PRODUCTION

BDF1 female mice (8 per group) were immunized with 0.2 ml of emulsions containing 50 μg of the AGPs+50 μg of ovalbumin. A second immunization was administered 21 days post primary. Each mouse was bled 14 days after the second injection. Antibody titers of immunized mice showing total IgG and IgM as well as titers for the subgroups of IgG including IgG$_1$, IgG$_{2a}$ and IgG$_{2b}$ are given in Table 7.

TABLE 7

Adjuvant activity in BDF1 mice immunized with ovalbumin.

| | Total Ig | | IgM | |
|---|---|---|---|---|
| Material | T/C* | Titer | T/C | Titer |
| B11 | 0.7 | 150 | 1.3 | 250 |
| B2 | 2.5 | 563 | 0.9 | 175 |
| B1 | 0.5 | 119 | 0.8 | 150 |
| B25 | 1.9 | 438 | 0.8 | 150 |
| B21 | 0.5 | 113 | 1.3 | 250 |
| B15 | 4.1 | 925 | 2.3 | 438 |
| B27 | 0.6 | 138 | 1.6 | 300 |
| Vehicle | — | 225 | — | 188 |

| | IgG1 | | IgG2a | | IgG2b | |
|---|---|---|---|---|---|---|
| Material | T/C* | Titer | T/C | Titer | T/C | Titer |
| B11 | 1.6 | 2650 | 1.7 | 550 | 1.6 | 375 |
| B2 | 5.0 | 8300 | 2.5 | 825 | 2.3 | 550 |
| B1 | 0.5 | 763 | 0.2 | 56 | 0.8 | 188 |
| B25 | 5.2 | 8500 | 0.5 | 163 | 5.0 | 1188 |
| B21 | 0.6 | 0.1 | 25 | 0.8 | 200 | |
| B15 | 0.6 | 950 | 0.3 | 113 | 16.7 | 3963 |
| B27 | 0.8 | 1275 | 0.1 | 38 | 0.5 | 113 |
| Vehicle | — | 1650 | — | 325 | — | 238 |

*T/C Ratio = Experimental Test Titer ÷ Vehicle Control Titer

The AGP compounds of the subject invention when administered to a warm-blooded animal with the antigen ovalbumin stimulates the production of antibody to that antigen.

TEST EXAMPLE 3

GENERATION OF A PROTECTIVE IMMUNE RESPONSE TO INFECTIOUS INFLUENZA

Mice vaccinated with formalin-inactivated influenza and the AGP compounds of the subject invention mounted a protective immune response to an influenza challenge as well as produced antibody to that antigen. Animals were vaccinated with the antigen and AGP compounds in various carriers. The degree of protection was determined by challenging the mice with intranasal (IN) administration of approximately 10 LD$_{50}$ infectious influenza A/HK/68. Mortality was assessed for 21 days following the challenge. The number of mice surviving the challenge dose is a direct assessment of the efficacy of the vaccine. For the experiments provided this data does not necessarily correlate with the amount of antibody produced.

1) Vaccines were formulated in 0.2% triethanolamine (TEoA)/water solution containing: 1 hemagglutinating unit (HAU) of formalin-inactivated influenza A|HK/68 (FI-Flu), and 50 μg of AGP except the vehicle control vaccines which contained no AGP. ICR mice (10/group) were vaccinated 1 time only. The vaccines were administered by subcutaneous (SQ) injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at −20° C. until used for enzyme-linked immunosorbent assay (ELISA). All mice were challenged 30 days post vaccination by intranasal (IN) administration of approximately 10 LD$_{50}$ infectious influenza A/HK/68. Mortality was assessed for 21 days following the challenge. Anti-influenza antibody titers obtained from vaccinations with TEoA formulations and corresponding survival rates of mice vaccinated with this formulation are shown in Table 8.

TABLE 8

Anti-influenza antibody titers and survival rates of treated mice.

| Material | Titer$^{-1}$ Total IgG | Percent Survival |
|---|---|---|
| Nonimmune | <100 | 0 |
| Vehicle | <100 | 0 |
| B9 | 6400 | 44 |
| B10 | 1600 | 40 |
| B7 | 200 | 33 |
| B3 | 1600 | 33 |
| B14 | 6400 | 44 |
| B15 | 6400 | 50 |

2) Vaccines were formulated in 2% Squalene solution containing: 1 hemagglutinating unit (HAU) of formalin-inactivated influenza A/HK/68 (FI-Flu), and 25 μg of AGP except the saline and vehicle control vaccines which contained no AGP. BALB/c mice (10/group) were vaccinated 1 time only. The vaccines were administered by subcutaneous (SQ) injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at −20° C. until used for enzyme-linked immunosorbent assay (ELISA). All mice were challenged 35 days post vaccination by intranasal (IN) administration of approximately 10 $LD_{50}$ infectious influenza A/HK/68. Mortality was assessed for 21 days following the challenge. Anti-influenza antibody titers obtained from vaccinations with the squalene formulations as well as corresponding survival rates of vaccinated animals are shown in Table 9.

TABLE 9

Anti-influenza antibody titers and survival rates of treated mice.

| Material | Total IgG | IgG1 | IgG2a | IgG2b | Percent Survival |
|---|---|---|---|---|---|
| Nonimmune | <100 | <100 | <100 | <100 | 0 |
| Saline | 800 | 100 | 800 | 100 | 62.5 |
| Vehicle | 1600 | 1600 | 1600 | 1600 | 100 |
| B25 | 3200 | 1600 | 6400 | 1600 | 100 |
| B15 | 1600 | 3200 | 3200 | 400 | 100 |
| B9 | 1600 | 1600 | 3200 | 800 | 87.5 |
| B10 | 400 | 400 | 400 | 400 | 62.5 |
| B3 | 3200 | 3200 | 6400 | 800 | 87.5 |
| B6 | 800 | 800 | 400 | 1600 | 75 |
| B14 | 3200 | 6400 | 3200 | 6400 | 87.5 |
| B28 | 800 | 400 | 400 | 100 | 50 |

3) The antibody titers and survival rate of vaccinated mice were compared after a primary then a secondary vaccination. Vaccines were formulated in 0.2% TEoA/water solution containing: 1 hemagglutinating unit of formalin-inactivated influenza A/HK/68, 25 μg AGP, except the vehicle control vaccine which contained no AGP. ICR mice (20/group) were administered vaccines by subcutaneous injection of 0.1 ml/site at 2 distinct sites near the inguinal lymph nodes for a total of 0.2 ml of vaccine/mouse. Each group was split into 2 subgroups 35 days after the primary vaccination. One of each subgroup was challenged at this time, the remaining subgroups received a secondary vaccination. Mice (only 5/subgroup) were bled from the orbital plexus 14 days following vaccination (primary or secondary). Sera was 3. harvested and frozen at −20° C. until used for ELISA. Mice were challenged 35 post primary, or secondary, vaccination by intranasal administration of approximately 10 LID50, or 40 LD50, infectious influenza A/EK/68, respectively. Mortality was assessed for 21 days following the challenge. Anti-influenza antibody titers and survival rates of mice post primary and post secondary vaccination are shown in Table 10. Antibody titers as well as survival rates of mice vaccinated a second time were higher.

TABLE 10

Antibody titers and survival rates of treated mice.

| | IgG Titer-1 | | Percent Survival | |
|---|---|---|---|---|
| Material | post 1° | post 2° | post 1° | post 2° |
| Nonimmune | 200 | 100 | 0 | 0 |
| Vehicle | 800 | 102,400 | 20 | 40 |
| B9 | 6400 | 12,800 | 80 | 50 |

TABLE 10-continued

Antibody titers and survival rates of treated mice.

| | IgG Titer-1 | | Percent Survival | |
|---|---|---|---|---|
| Material | post 1° | post 2° | post 1° | post 2° |
| B10 | 1600 | 25,600 | 60 | 90 |
| B7 | 3200 | >102,400 | 60 | 60 |
| B4 | 800 | 25,600 | 50 | 70 |
| B3 | 3200 | 102,400 | 70 | 60 |
| B5 | 1600 | >102,400 | 60 | 90 |
| B6 | 1600 | 102,400 | 80 | 70 |
| B14 | 800 | 51,200 | 33 | 70 |

TEST EXAMPLE 4

THE EFFECT OF FATTY ACID CHAIN LENGTH ON ADJUVANTICITY

The effect of the length of fatty acid chains $R_1$–$R_3$ on activity was tested. Vaccines were formulated in 0.2% TEoA/water solution containing: 1 hemagglutinating unit of formalin-inactivated influenza A/HK168, and 25 μg of AGP, except the vehicle control vaccines which contained no AGP. ICR mice (10/group) were vaccinated 1 time only. The vaccines were administered by subcutaneous injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at −20° C. until used for ELISA. All mice were challenged 35 post vaccination by intranasal administration of approximately 10 $LD_{50}$ infectious influenza A/HK/68. Mortality was assessed for 21 days following the challenge. The length of the fatty acid chain appears to mildly affect biological activity. Results are shown in Tables 11 and 12.

TABLE 11

Antibody titers and survival rates of treated mice.

| | | Titer$^{-1}$ | | | | |
|---|---|---|---|---|---|---|
| Material | Chain Length | Total IgG | IgG1 | IgG2a | IgG2b | Percent Survival |
| Nonimmune | — | 200 | 100 | 100 | 800 | 0 |
| Vehicle | — | 200 | 100 | 100 | 200 | 11 |
| B18 | 7 | 800 | 800 | 800 | 400 | 20 |
| B17 | 8 | 6400 | 3200 | 3200 | 1600 | 40 |
| B16 | 9 | 800 | 1600 | 100 | 800 | 40 |
| B15 | 10 | 3200 | 200 | 3200 | 6400 | 70 |
| B14 | 10 | 800 | 1600 | 100 | 400 | 30 |
| B13 | 11 | 1600 | 800 | 400 | 800 | 50 |
| B12 | 12 | 200 | 200 | 100 | 200 | 0 |
| B11 | 14 | 1600 | 200 | 1600 | 400 | 30 |

TABLE 12

Antibody titers and survival rates of treated mice.

| | | Titer$^{-1}$ | | | | |
|---|---|---|---|---|---|---|
| Material | Chain Length | Total IgG | IgG1 | IgG2a | IgG2b | Percent Survival |
| Nonimmune | — | 100 | 100 | 50 | 800 | 0 |
| Vehicle | — | 100 | 200 | 50 | 100 | 30 |
| B8 | 7 | 6400 | 3200 | 400 | 1600 | 80 |

TABLE 12-continued

Antibody titers and survival rates of treated mice.

| Material | Chain Length | Total IgG | IgG1 | IgG2a | IgG2b | Percent Survival |
|---|---|---|---|---|---|---|
| B7 | 9 | 3200 | 3200 | 100 | 1600 | 70 |
| B5 | 10 | 800 | 200 | 50 | 400 | 44 |
| B4 | 11 | 3200 | 400 | 100 | 1600 | 60 |
| B3 | 12 | 1600 | 1600 | 50 | 800 | 0 |
| B1 | 14 | 12,800 | 6400 | 1600 | 15600 | 40 |

Titer$^{-1}$

TEST EXAMPLE 5

THE EFFECT OF VARIATIONS IN THE CARBON CHAIN LENGTH BETWEEN THE HETEROATOM X AND THE AGLYCON NITROGEN ATOM ON ADJUVANTICITY

The length of the carbon chain between X and the aglycon nitrogen atom was extended progressively by a single atom. The effect of lengthening the chain between these two components on adjuvanticity was explored. Vaccines were formulated in 0.2% TEoA/water solution containing: I hemagglutinating unit of formalin-inactivated influenza A/HK/68, and 25 μg of AGP, except the vehicle control vaccines which contained no AGP. ICR mice (10/group) were vaccinated 1 time only. The vaccines were administered by subcutaneous injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at –20° C. until used for ELISA. All mice were challenged 35 days post vaccination by intranasal administration of approximately 10 LD$_{50}$ infectious influenza A/HK/68. Mortality was assessed for 21 days following the challenge. Adjuvant activity appears to lessen as the length of the carbon chain between the heteroatom X and aglycon nitrogen atom increases. However, depending upon the residues attached to this carbon chain the biologic and metabolic stability of the molecules may be affected. Results are shown in Tables 13.

TABLE 13

Antibody titers and survival rates of treated mice.

| Material | Carbon Chain | Total IgG | IgG1 | IgG2a | IgG2b | Percent Survival |
|---|---|---|---|---|---|---|
| Nonimmune | — | <50 | <50 | <50 | <50 | 0 |
| Vehicle | — | 200 | 200 | 50 | 200 | 25 |
| B19 | 2 | 12,800 | 100 | 800 | 6400 | 50 |
| B21 | 3 | 6400 | 800 | 100 | 1600 | 40 |
| B22 | 4 | 3200 | 100 | 3200 | 200 | 40 |

Titer$^{-1}$

TEST EXAMPLE 6

CYTOKINE INDUCTION BY THE AGP COMPOUNDS

The AGP compounds of the subject invention induced cytokines in human whole blood ex vivo culture assays. AGP compounds were solubilized in 10% EtOH-water and diluted to various concentrations. Fifty μl of each dilution were added to 450 μl of whole human blood. Controls were treated with culture media (RPMI). The reaction mixture was incubated at 37° C. for 4 hr with constant mixing on a rotator. Sterile PBS (1.5 ml) was added to the reaction mixture, the cells were centrifuged and the supernatents removed for cytokine testing. The concentration of TNF-α and IL-1 βin each supernatent was determined using immunoassay ELISA kits from R&D Systems. Results from these studies are shown in Tables 14–19.

TABLE 14

Stimtilation of cytokine secretion in an ex vivo assay.

| Material | Dosage (μg) | TNF-α (pg/ml) | IL-1β (pg/ml) |
|---|---|---|---|
| B26 | 20 | 498.90 | 33.25 |
|  | 10 | 254.94 | 25.34 |
|  | 5 | 75.62 | 9.89 |
|  | 1 | 38.85 | 3.90 |
| B2 | 20 | 1338.42 | 155.07 |
|  | 10 | 817.67 | 114.41 |
|  | 5 | 235.32 | 34.72 |
|  | 1 | 105.52 | 14.53 |
| RPMI | — | 2 | 0 |

TABLE 15

Stimulation of cytokines in an ex vivo assay.

| Material | Dosage (ng/ml) | TNF-α (pg/ml) | IL-1β (pg/ml) |
|---|---|---|---|
| B16 | 10,000 | 291 | 55 |
|  | 5000 | 277 | 53 |
|  | 1000 | 155 | 39 |
| B13 | 10,000 | 775 | THTC* |
|  | 5000 | 716 | 187 |
|  | 1000 | 740 | 177 |
| B9 | 10,000 | 449 | 96 |
|  | 5000 | 247 | 84 |
|  | 1000 | 145 | 53 |
| B10 | 10,000 | 207 | 43 |
|  | 5000 | 127 | 61 |
|  | 1000 | 73 | 17 |
| B7 | 10,000 | 83 | 16 |
|  | 5000 | 57 | 14 |
|  | 1000 | 26 | 6 |
| RPMI | — | 2 |  |

*THTC-To high to Count

TABLE 16

Stimulation of cytokines in an ex vivo assay.

| Material | Dosage (ng/ml) | TNF-α (pg/ml) | IL-1β (pg/ml) |
|---|---|---|---|
| B4 | 10,000 | 432 | 213 |
|  | 5000 | 205 | 164 |
|  | 1000 | 94 | 70 |
| B3 | 10,000 | 567 | 269 |
|  | 5000 | 390 | 342 |
|  | 1000 | 189 | 204 |
| B5 | 10,000 | 169 | 79 |
|  | 5000 | 143 | 162 |
|  | 1000 | 43 | 36 |
| B6 | 10,000 | 94 | 52 |
|  | 5000 | 59 | 29 |
|  | 1000 | 30 | 13 |

TABLE 16-continued

Stimulation of cytokines in an ex vivo assay.

| Material | Dosage (ng/ml) | TNF-α (pg/ml) | IL-1β (pg/ml) |
|---|---|---|---|
| B14 | 10,000 | 249 | 91 |
|  | 5000 | 120 | 71 |
|  | 1000 | 56 | 46 |
| RPMI | — | 2 | 0 |

TABLE 17

Stimulation of cytokine secretion in an ex vivo assay.

| Material | Dosage (ng/ml) | TNF-α (pg/ml) | IL-1β (pg/ml) |
|---|---|---|---|
| B11 | 10,000 | 181 | 62.3 |
|  | 5000 | 139 | 61.7 |
|  | 1000 | 115 | 54.5 |
|  | 500 | 125 | 55.8 |
|  | 100 | 127 | 59.8 |
| B13 | 10,000 | 583 | 282 |
|  | 5000 | 592 | 390 |
|  | 1000 | 478 | 327 |
|  | 500 | 411 | 352 |
|  | 100 | 302 | 261 |
| B15 | 10,000 | 320 | 153 |
|  | 5000 | 280 | 126 |
|  | 1000 | 209 | 94.4 |
|  | 500 | 183 | 104 |
|  | 100 | 133 | 51.6 |
| B16 | 10,000 | 121 | 41.0 |
|  | 5000 | 114 | 34.0 |
|  | 1000 | 72 | 19.5 |
|  | 500 | 55 | 17.1 |
| B14 | 10,000 | 114 | 24.6 |
|  | 5000 | 87 | 19.0 |
|  | 1000 | 51 | 10.0 |
|  | 500 | 49 | 19.9 |
| RPMI | — | 2 | 0 |

TABLE 18

Stimulation of cytokine secretion in an ex vivo assay.

| Material | Dosage (ng/ml) | TNF-α (pg/ml) | IL-1β (pg/ml) |
|---|---|---|---|
| B2 | 10,000 | 100 | 22.2 |
|  | 5000 | 75 | 14.0 |
|  | 1000 | 38 | 9.0 |
|  | 500 | 28 | 8.3 |
|  | 100 | 6.1 | 3.5 |
| B1 | 10,000 | 20 | 10.0 |
|  | 5000 | 11 | 5.5 |
|  | 1000 | 2.8 | 4.0 |
|  | 500 | 1.1 | 0 |
|  | 100 | 0 | 0 |
| B7 | 10,000 | 61 | 14.7 |
|  | 5000 | 44 | 8.3 |
|  | 1000 | 30 | 4.3 |
|  | 500 | 27 | 3.8 |
|  | 100 | 10 | 5.1 |
| B4 | 10,000 | 232 | 66.9 |
|  | 5000 | 173 | 66.5 |
|  | 1000 | 130 | 32.0 |
|  | 500 | 116 | 19.3 |
|  | 100 | 89 | 65.2 |
| B3 | 10,000 | 433 | 151.9 |
|  | 5000 | 316 | 200.4 |
|  | 1000 | 229 | 75.1 |
|  | 500 | 212 | 67.9 |
|  | 100 | 130 | 35.9 |

TABLE 18-continued

Stimulation of cytokine secretion in an ex vivo assay.

| Material | Dosage (ng/ml) | TNF-α (pg/ml) | IL-1β (pg/ml) |
|---|---|---|---|
| B5 | 10,000 | 142 | 24.1 |
|  | 5000 | 99 | 23.0 |
|  | 1000 | 96 | 10.5 |
|  | 500 | 59 | 16.9 |
|  | 100 | 33 | 5.4 |
| RPMI | — | 2 | 0 |

TABLE 19

Stimulation of cytokine secretion in an ex vivo assay.

| Material | Dosage (ng/ml) | TNF-α (pg/ml) | IL-1β (pg/ml) |
|---|---|---|---|
| B17 | 10,000 | 2.8 | 0 |
|  | 5000 | 2.2 | 0 |
|  | 1000 | 2.6 | 0.2 |
| B8 | 10,000 | 2.8 | 0 |
|  | 5000 | 0.7 | 0.5 |
|  | 1000 | 1.5 | 0.1 |
| B22 | 10,000 | 287 | 17 |
|  | 5000 | 11 | 1.9 |
|  | 1000 | 2.2 | 0.1 |
| B28 | 10,000 | 198 | 13 |
|  | 5000 | 197 | 13 |
|  | 1000 | 139 | 8 |
| B12 | 10,000 | 1017 | 135 |
|  | 5000 | 957 | 153 |
|  | 1000 | 863 | 175 |
| RPMI | — | 3.9 | 0 |

TEST EXAMPLE 7

STIMULATION OF A CYTOTOXIC T-LYMPHOCYTE RESPONSE

The induction of a cytotoxic T-lymphocyte response after administration of the AGP compounds of the subject invention and a protein antigen was detected by a cytotoxicity assay. Groups of C57BIJ6 mice were given a primary immunization subcutaneously (inguinal region) with 25 μg ovalbumin (OVA) formulated in AGP preparations. The injected volume was 200 μl. Twenty-one days later three mice per experimental group were killed and spleens removed and pooled as single cell suspensions and counted.

Spleen cells ($75 \times 10^6$ cells in 3–4 ml media) from the experimental groups were placed in a 25 cm² T-flask. Next, 1.0 ml of irradiated (20,000 rads) E.G7 (OVA) cells at $5 \times 10^6$/ml were added to the flask. The volume was brought to 10 ml. The cultures were maintained by placing the T-flasks upright in a 37° C., 5% $CO_2$ incubator for four days. On day 4 the surviving cells were recovered from the flasks, washed 1X in fresh media resuspended in 5.0 ml, and counted.

Recovered effector cells were adjusted to $5 \times 10^6$ viable cells/ml and 100 μl volumes were diluted serially in triplicate in wells of 96 well round-bottom plates (Corning 25850) using 100 μl/well of media as a diluent. Next, 100 μl volumes of $^{51}$Cr-labelled (see below) targets [E.G7 (OVA)-an ovalbumin gene transfected EL-4 cell line] at $1 \times 10^5$ cells/ml were added to the wells. Spontaneous release (SR) wells contained 100 μl of targets and 100 μl of media. Maximal release (MR) wells contained 100 μl of targets and 100 μl detergent (2% Tween 20). Effector/target (EIT) ratios were 50:1, 25:1, 12.5:1. The plates were centrifuged at 400×g and incubated at 37° C., 5% $CO_2$ for 4 hr. After the incubation the well supernatants were collected using a Skatron Supernatant Collection System.

Percent specific lysis=

$$100 \times \left[\frac{(\text{Exp. Release} - SR)}{(MR - SR)}\right]$$

Target cells, E.G7 (OVA), were labelled with $^{51}Cr$ (sodium chromate) as follows. In a total volume of 1.0 ml were mixed 5×10$^6$ target cells and 250 μCi $^{51}Cr$ in 15 ml conical tube. The cell suspensions was incubated in a 37° C. water bath for 90 min., with gentle mixing every 15 min. After incubation the labelled cells were washed 3× by centrifugation and decanting with 15 ml volumes of media. After the third centrifugation the cells were resuspended in 10 ml of fresh media and allowed to stand at room temperature for 30 min. and then centrifuged. The cells were finally resuspended in media at 1×10$^5$ cells/ml.

Mice immunized according to the procedure above with the AGPs of the subject invention displayed a cytotoxic T-lymphocyte response to the OVA antigen as shown in Table 20.

TABLE 20

Cytotoxic T-lymphocyte response of treated cells.

| | % Cytotoxicity E:T | | |
|---|---|---|---|
| Material | 50:1 | 25:1 | 12.5:1 |
| B11 | 14 | 8 | 5 |
| B12 | 13 | 7 | 4 |
| B13 | 28 | 15 | 10 |
| B15 | 58 | 49 | 30 |
| B16 | 42 | 29 | 20 |
| B17 | 39 | 26 | 15 |
| B18 | 36 | 20 | 15 |
| B14 | 45 | 36 | 25 |
| B28 | 28 | 15 | 9 |
| B27 | 17 | 9 | 5 |
| B1 | 34 | 24 | 15 |
| B3 | 65 | 54 | 42 |
| B4 | 72 | 66 | 60 |
| B5 | 28 | 18 | 11 |
| B7 | 57 | 44 | 29 |
| B8 | 36 | 20 | 15 |
| B10 | 65 | 56 | 38 |
| B9 | 65 | 55 | 36 |
| B6 | 54 | 41 | 37 |
| B2 | 21 | 12 | 6 |
| B25 | 65 | 55 | 43 |
| B26 | 14 | 8 | 4 |
| B22 | 58 | 42 | 31 |
| B21 | 38 | 26 | 15 |
| B19 | 59 | 42 | 33* |
| B20 | 36 | 25 | 13 |
| B29 | 16 | 9 | 5 |
| B31 | 19 | 11 | 7 |
| B35 | 9 | 5 | 2 |
| B36 | 13 | 7 | 4 |
| B37 | 12 | 8 | 6 |
| B38 | 38 | 25 | 16 |
| B39 | 33 | 21 | 13 |
| B40 | 20 | 12 | 8 |
| B43 | 19 | 12 | 6 |
| Vehicle Control | <10 | | |

TEST EXAMPLE 8

GENERATION OF SERUM AND MUCOSAL ANTIBODY TITERS TO TETANUS-TOXOID

The AGPs of the subject invention elicited both a serum and mucosal immune response to purified tetanus toxoid when administered intranasally. Groups of BALB/c mice were given a primary immunization (1°) intranasally with 10 μg tetanus toxoid (TT)+20 μg AGP formulated in an aqueous formulation (AF) in a volume of 20 μl. A secondary immunization (2°) was given 14 days later and a tertiary immunization (3°) identical in composition to the first and second was administered 14 days later. Mice were bled on day 21 (day 7 post 2°) and day 38 (day 10 post 3°) and day 48 (day 20 post 3°). Vaginal wash/fecal extract samples were taken on day 7 post 2° and day 7 post 3°. Serum and wash samples were assayed for anti-TT antibody by standard ELISA methods. Results of these assays are shown in Tables 21 and 22 below.

The aqueous formulation comprises the AGPs of the subject invention and one or more surfactants. Surfactants useful in an aqueous composition include glycodeoxycholate, deoxycholate, sphingomyelin, sphingosine, phosphatidylcholine, 1,2-Dimyristoyl-sn-glycero-3-phosphoethanolamine, L-α-phosphatidylethanolamine, and 1,2-Dipalmitoyl-sn-glycero-3-phosphocholine, or a mixture thereof. The aqueous formulation used in this example comprises the surfactant 1,2 dipalmitoyl-sn-glycero-3-phosphocholine (DPPC) and was prepared as follows: briefly; a 4 mg/ml solution of DPPC was prepared in ethanol. An aliquot of the ethanol solution is added to the dried AGPs and swirled gently to wet the AGP. The ethanol is removed by blowing a stream of filtered nitrogen gently over the vial. Water for Injection is added and the suspension is sonicated 10 min. at 60° C. until clear. The resulting aqueous formulation contains approximately 118 μg/ml DPPC, has particles of around 70 nm and was filter sterilized.

TABLE 21

Anti-tetanus toxoid antibody titers in treated mice.

Anti-Tetanus Toxoid Titer$^{-1}$

| | Vaginal Wash | | | | Fecal Extract | | | |
|---|---|---|---|---|---|---|---|---|
| | IgG | | IgA | | IgG | | IgA | |
| Material | 2° | 3° | 2° | 3° | 2° | 3° | 2° | 3° |
| B25 | 800 | 6400 | 6400 | 6400 | 50 | 200 | 3200 | 6400 |
| B15 | 400 | 800 | 6400 | 6400 | 50 | 100 | 6400 | 12,800 |
| B19 | 200 | 400 | 1600 | 3200 | 25 | 25 | 3200 | 6400 |
| B4 | 1600 | 400 | 1600 | 6400 | 25 | 50 | 3200 | 12,800 |
| B5 | 3200 | 800 | 3200 | 3200 | 50 | 100 | 3200 | 6400 |
| B3 | 1600 | 1600 | 6400 | 6400 | 50 | 100 | 3200 | 6400 |
| B22 | 400 | 800 | 800 | 3200 | 25 | 50 | 1600 | 6400 |
| PBS | <25 | <25 | <25 | <25 | <25 | <25 | <25 | <25 |
| Normal Sera | <25 | <25 | <25 | <25 | <25 | <25 | <25 | <25 |

TABLE 22

Serum anti-tetanus toxoid antibody titers in treated animals.

Anti-Tetanus Toxoid Titer[−1]
Serum Pools

|  | IgG$_1$ | | | IgG$_{2a}$ | | | IgA | | |
|---|---|---|---|---|---|---|---|---|---|
|  | d21 | d38 | d48 | d21 | d38 | d48 | d21 | d38 | d48 |
| B25 | 1M* | 8M | 8M | 512K | 4M | 4M | 12.8K | 102.4K | 102.4K |
| B15 | 2M | 8M | 8M | 512K | 1M | 2M | 12.8K | 51.2K | 25.6K |
| B19 | 2M | 4M | 4M | 64K# | 256K | 128K | 6.4K | 25.6K | 12.8K |
| B4 | 1M | 8M | 8M | 1M | 2M | 2M | 25.6K | 102.4K | 102.4K |
| B5 | 2M | 8M | 8M | 512K | 2M | 2M | 25.6K | 102.4K | 102.4K |
| B3 | 512K | 4M | 8M | 512K | 2M | 2M | 12.8K | 51.2K | 51.2K |
| B22 | 1M | 2M | 4M | 64K | 256K | 256K | 6.4K | 25.6K | 25.6K |
| PBS | 1,000 | 16K | 16K | 1,000 | 1,000 | 1,000 | 200 | 200 | 200 |
| C | 200 | 200 | 200 | 100 | 100 | 100 | 200 | 200 | 200 |

*M = $10^6$, #K = $10^3$, C = normal sera

Intranasal administration of TT formulated in AGP-AF induced both an antigen specific humoral immune response (Table 22) and a mucosal immune response (Table 21) to that antigen.

TEST EXAMPLE 9

STIMULATION OF AN IMMUNE RESPONSE TO HEPATITIS B SURFACE ANTIGEN BY INTRANASAL ADMINISTRATION

Mice administered hepatitis B surface antigen (HBsAg) intranasally with the compounds of the subject invention produced serum IgG and IgA titers to that antigen. Secretory IgA was detected in vaginal washes and the induction of a cytotoxic T-lymphocyte response was detected by a cytotoxicity assay.

Groups of BALB/c mice were given a primary immunization (1°) intranasally with 2.5 μg HBsAg+10 μg AGP-AF in a volume of 20 μl. AGP-AF was prepared as in TEST EXAMPLE 8. Twenty-one days later mice were given a secondary immunization (2°) of 7.5 μg HBSAG+10 μg AGP-AF intranasally in 20 μl volume. A tertiary immunization (3°) identical in composition to the secondary immunization was administered 28 days after the secondary immunization. Assays were conducted to detect cytotoxic T-lymphocyte activity at 16 days post secondary immunization (d16 post 2°) and 8 days post tertiary immunization (d8 post 3°). Serum and mucosal antibody titers were assessed at 22 days post secondary immunization (d22 post 2°) and 21 days post tertiary immunization (d21 post 3°). Antibody assays were conducted by standard ELISA methods. Cytotoxicity assays were conducted as described in TEST EXAMPLE 7. Results from this experiment are shown in Tables 23–26.

TABLE 23

Cytotoxic T-lymphocyte response of treated cells.

% Cytotoxicity (d16, post 2°) E/T

| Material | 50:1 | 25:1 | 12.5:1 | 6.25:1 |
|---|---|---|---|---|
| B25 | 36 | 20 | 13 | 9 |
| B15 | 13 | 5 | 4 | 4 |
| B19 | 26 | 20 | 11 | 9 |

TABLE 23-continued

Cytotoxic T-lymphocyte response of treated cells.

% Cytotoxicity (d16, post 2°) E/T

| Material | 50:1 | 25:1 | 12.5:1 | 6.25:1 |
|---|---|---|---|---|
| B4 | 28 | 17 | 9 | 7 |
| B3 | 43 | 26 | 17 | 11 |
| B5 | 43 | 30 | 20 | 11 |
| B22 | 33 | 21 | 15 | 8 |
| Vehicle | 3 | 2 | 0 | 0 |
| Normal Cells | 3 | 3 | 0 | 0 |

TABLE 24

Cytotoxic T-lymphocyte response of treated cells.

% Cytotoxicity (d8, post 3°) E/T

| Material | 50:1 | 25:1 | 12.5:1 | 6.25:1 |
|---|---|---|---|---|
| B25 | 30 | 19 | 13 | 8 |
| B15 | 56 | 42 | 25 | 16 |
| B19 | 71 | 54 | 33 | 24 |
| B4 | 23 | 15 | 9 | 5 |
| B3 | 54 | 45 | 32 | 20 |
| B5 | 44 | 30 | 19 | 12 |
| B22 | 22 | 13 | 7 | 5 |
| Vehicle | 5 | 2 | 1 | 1 |
| Normal Cells | 7 | 5 | 3 | 3 |

TABLE 25

Anti-hepatitis antibody titers in treated mice.

Anti HBsAg Titer[−1]*

| Material | IgG$_1$ | IgG$_{2a}$ | IgA |
|---|---|---|---|
| B25 | 256K# | 500K | 3,200 |
| B15 | 256K | 500K | 6,400 |
| B19 | 500K | 64K | 1,600 |
| B4 | 500K | 1000K | 6,400 |
| B3 | 1000K | 500K | 6,400 |
| B5 | 256K | 500K | 3,200 |

TABLE 25-continued

Anti-hepatitis antibody titers in treated mice.

| | Anti HBsAg Titer[-1]* | | |
|---|---|---|---|
| Material | IgG$_1$ | IgG$_{2a}$ | IgA |
| B22 | 256K | 64K | 1,600 |
| Vehicle | <2K | <2K | <200 |

*day 22 post 2°, #K = 10$^3$

TABLE 26

Anti-hepatitis antibody titers in treated mice.

| | Anti HBsAg Titer-1* | | |
|---|---|---|---|
| Material | IgG$_1$ | IgG$_{2a}$ | IgA |
| B25 | 1000K# | 1000K | 25,600 |
| B15 | 2000K | 2000K | 25,600 |
| B19 | 2000K | 500K | 12,800 |
| B4 | 1000K | 2000K | 25,600 |
| B3 | 1000K | 1000K | 25,600 |
| B5 | 500K | 1000K | 12,800 |
| B22 | 500K | 500K | 12,800 |
| Vehicle | <2K | <2K | <200 |

* day 21 post 3°, #K = 10$^3$

Groups of BALB/c mice were immunized with 2.5 µg HBsAg +10 µg AGP-AF intranasally and boosted intranasally with 7.5 µg HBsAg+10 µg AGP-AF 21 days later. Vaginal samples were collected 10 days after the booster immunization and assayed for anti-HBsAg antibody. Results of this assay are shown in Table 27.

TABLE 27

| | Vaginal Wash Anti-HBsAg Titer[-1] | |
|---|---|---|
| Material | IgG | IgA |
| B25 | 100 | 800 |
| B15 | 50 | 3200 |
| B19 | >50 | 400 |
| B4 | 1600 | 6400 |
| B3 | 800 | 1600 |
| B5 | 1600 | 1600 |
| B22 | 100 | 800 |
| Vehicle | <50 | <50 |

The intranasal administration of HBsAg with the compounds of the subject invention stimulated both a humoral and cellular immune response to that antigen. Intranasal immunization with the antigen formulated in AGP-AF induced a cytotoxic T-lymphocyte response (Table 23–24) and antigen specific humoral (Table 25 and 26) and mucosal (Table 27) immune responses.

TEST EXAMPLE 10

GENERATION OF A PROTECTIVE IMMUNE RESPONSE TO INFLUENZA

Mice immunized intranasally with FLUSHEELD influenza vaccine containing hemagglutinin antigen and the AGPs of the subject invention produced both IgG and IgA which were recovered in vaginal washes. Immunized mice were also protected from subsequent influenza challenge.

ICR mice were immunized three times at 21 day intervals intranasally with FLUSHIELD influenza vaccine (Wyeth-Lederle) containing 0.3 µg hemagglutinin antigen (HA)+10 µg AGP-AF or recombinant E. coli heat labile enterotoxin (LT). AGP-AF was prepared as in TEST EXAMPLE 8. LT was solubilized in saline at 1 µg/ml. Vaginal washes were collected 14 days after the second and third immunization. Serum samples were collected 14 days after the third immunization. Mice were challenged with 10 LD$_{50}$ (lethal dose 50) of infectious influenza A/HK/68 thirty-five days after the final immunization and monitored for mortality. Tables 28 and 29 show the results of assays conducted by standard ELISA methods to detect anti-influenza antibody titers in vaginal washes and sera.

TABLE 28

| | Vaginal Wash Samples | | | | |
|---|---|---|---|---|---|
| | IgA | | IgG | | Percent |
| Material | Secondary | Tertiary | Secondary | Tertiary | Protection |
| Nonimmune | <20 | <20 | <20 | <20 | 22 |
| Vehicle | 80 | 160 | 160 | 160 | 50 |
| B25 | 1280 | 1280 | 640 | 2560 | 100 |
| B19 | 320 | 5120 | 1280 | 1280 | 70 |
| B3 | 1280 | 2560 | 1280 | 1280 | 100 |
| B22 | 640 | 2560 | 320 | 640 | 75 |
| LT | 2560 | 2560 | 2560 | 640 | 100 |

TABLE 29

| | Serum Titers | | | | Percent |
|---|---|---|---|---|---|
| Material | Total IgG | IgG$_1$ | IgG$_{2a}$ | IgG$_{2b}$ | Protection |
| Nonimmune | <400 | <400 | <400 | <400 | 22 |
| Vehicle | 102,400 | 256,000 | 12,800 | 102,400 | 50 |
| B25 | ≧819,200 | 102,400 | 819,200 | ≧819,200 | 100 |
| B19 | 819,200 | 51,200 | 102,400 | 819,200 | 70 |
| B3 | ≧819,200 | 51,200 | 819,200 | ≧819,200 | 100 |
| B22 | 819,200 | 51,200 | 102,400 | 819,200 | 75 |
| LT | ≧819,200 | ≧819,200 | ≧819,200 | ≧819,200 | 100 |

These data demonstrate that AGPs in AF when administered intranasally act as a mucosal adjuvants causing the production of IgA at mucosal sites. Increased protection is also induced against an upper respiratory pathogen which invades through the mucosa.

TEST EXAMPLE 11

GENERATION OF IMMUNE RESPONSES FROM STABLE EMULSION FORMULATIONS

The AGP compounds of the subject invention stimulated both humoral and cytotoxic T-lymphocyte responses when formulated in a stable emulsion (SE). AGPs were tested at 25 µg dose levels to adjuvantize Hepatitis B surface antigen (HBsAg) for the induction of CTL and antibody responses. BALB/c mice were immunized subcutaneously with 2.0 µg HBsAg plus 25 µg of AGP/SE on day 0 and day 21. The CTL assay was conducted as in TEST EXAMPLE 7. The AGPs were formulated in a stable emulsion (SE) and the compositions were designated AGP-SE. Methods for preparing the stable emulsion containing 10% v/v squalene, 0.091% w/v PLURONIC-F68 block copolymer, 1.909% w/v egg phosphatidyl choline, 1.8% v/v glycerol, 0.05% w/v a tocopherol, 10% ammonium phosphate buffer and 78.2% v/v Water for Injection should be readily apparent to one skilled in the art. The emulsion was homogenized to a particle size of ≧0.2 µm. Table 30 shows the AGPs of the subject invention induced a cytotoxic T-lymphocyte response to HBsAg.

TABLE 30

Cytotoxic T-lymphocyte response of treated cells.

| | | % Cytotoxicity E:T | | | |
|---|---|---|---|---|---|
| Material | Day | 50:1 | 25:1 | 12.5:1 | 6.25:1 |
| B25 | d17,post 1° | 27 | 12 | 9 | 5 |
| B19 | | 74 | 48 | 34 | 24 |
| B3 | | 28 | 15 | 9 | 5 |
| B22 | | 42 | 24 | 17 | 7 |
| Vehicle-SE | | 32 | 16 | 9 | 6 |
| | d16, post 2° | | | | |
| B25 | | 49 | 28 | 20 | 13 |
| B19 | | 73 | 62 | 42 | 31 |
| B3 | | 81 | 47 | 32 | 22 |
| B22 | | 78 | 69 | 58 | 39 |
| Vehicle-SE | | 38 | 23 | 14 | 8 |

The results of the antibody titer to HBsAg are shown on Table 31. Sera from bleeds taken on day 28 post 2° were titered on ELISA plates coated with either HBsAg or a 28 amino acid peptide (p72) which contains B-cell epitopes found in the S-antigen region, residues 110–137, of the HBsAg.

TABLE 31

Anti-HBsAg titer of treated mice.

| | Anti-HBsAg Titer$^{-1}$ | | | |
|---|---|---|---|---|
| | HBsAg | | p72-Peptide | |
| Material | IgG$_1$ | IgG$_{2a}$ | IgG$_1$ | IgG$_{2a}$ |
| B25 | 2048K* | 2048K | 128K | 64K |
| B19 | 1024K | 1024K | 64K | 128K |
| B3 | 512K | 1024K | 16K | 128K |
| B22 | 1024K | 1024K | 128K | 128K |
| Vehicle SE | 1024K | 64K | 64K | 4K |

AGP-SE treated mice displayed both humoral (Table 31) and cytotoxic T-lymphocyte (Table 30) responses to the hepatitis B surface antigen. Of interest, AGP-SE treated mice in serum displayed a vigorous IgG$_{2a}$ specific antibody titer detected by both antigens, whereas the vehicle-SE induced only a modest IgG$_{2a}$ response.

TEXT EXAMPLE 12

STIMULATION OF SERUM ANTIBODY TITERS

The AGP compound B31 was evaluated for its ability to enhance serum antibody titers to an influenza virus vaccine as set forth in Text Example 3. In brief, ICR mice (10/group) were administered vaccines containing 1 HAU of formalin-inactivated influenza A/HK/68 plus or minus 25 μg RC-523 formulated in a 0.2%TEoA/water solution. The mice were, also, challenged with a lethal dose of infectious influenza virus in order to assess protection. The results of this experiment are presented in Table 32.

TABLE 32

| | Anti-influenza serum titers | | | | |
|---|---|---|---|---|---|
| Material | IgG | IgG1 | IgG2a | IgG2b | Protection |
| Nonimmune | 200 | 50 | 50 | 100 | 0 |
| Vehicle | 200 | 200 | 50 | 200 | 25 |
| B31 | 3200 | 1600 | 400 | 1600 | 70 |

TEXT EXAMPLE 13

INDUCIBLE NITRIC OXIDE SYNTHETIC ACTIVITY

Screening of respective AGP compounds of this invention included evaluation of inducible nitric oxide synthetase or INOS activity (NOS ED$_{50}$), which correlates with macrophage activation, and can thus be viewed as a measure of immune stimulation. For this assay, mouse peritoneal exudates cells were harvested and the adherent cell population isolated. The adherent cells were exposed to varying concentrations of soluble AGP compounds and the resulting induction and secretion of nitrite measured. The NOS ED$_{50}$ value represents a concentration of AGP required to stimulate half the maximum amount of nitrite release and corresponds to the concentration required to stimulate macrophages.

The AGP compounds were also evaluated for their tendency to induce a fever response in rabbits. Each compound was formulated in 10% (v/v) ethanol/water solution at 100 mg/ml, then diluted with D$_5$W to the desired concentration. The material was injected at 3 ml/kg body weight into 3 rabbits. The rise in core temperature of the rabbits was recorded. A compound inducing a cumulative rise of greater than or equal to 1.5 degree in the three rabbits is considered pyrogenic.

The results of these experiments are presented in Table 33.

TABLE 33

| | NOS ED$_{50}$ | | | PYROGENICITY Total Rise ° C., 3 rabbits | | |
|---|---|---|---|---|---|---|
| | (nanograms/ml) | | | 2.5 | 10 | MPD |
| # | Exp. 1 | Exp 2 | Exp 3 | ug/kg | ug/kg | ug/kg |
| B1 | 150 | | | 0 | 0.1 | |
| B2 | 9 | | | 0.9 | 3.6 | 2.5–5 |
| B3 | 4 | | | 0 | 4.2 | |
| B4 | 5 | | | 0.1 | 3.4 | |
| B5 | 5 | | 3 | 0.1 | 4.1 | |
| B6 | | 1.8 | | 2.1 | — | |
| B7 | 21 | | | 0 | 4 | |
| B8 | ≧3000 | | | 3.6 | — | |
| B9 | 16 | | | 0 | 3.1 | |
| B10 | 4 | | | 0 | 5.8 | |
| B11 | 3 | | | 4.2 | — | 0.3–0.6 |
| B12 | | | 0.9 | 2.5 | — | |
| B13 | 0.1 | | | 3 | — | |
| B14 | 0.25 | | | 2.1 | — | |
| B15 | 0.06 | | | 4.2 | 3.1 | <0.06 |
| B16 | 0.46 | | | 1.8 | — | |
| B17 | | | 32.5 | 2.1 | 3.4 | |
| B18 | ≧3000 | | | 4.3 | — | |
| B19 | 100 | | | 0 | 0.3 | |
| B20 | 0.5 | | 1.5 | 0.3 | 4.6 | |
| B21 | 8 | | | 0.5 | 2 | |
| B22 | | | 51 | 1.7 | — | |

TABLE 33-continued

| # | NOS ED$_{50}$ (nanograms/ml) | | | PYROGENICITY Total Rise ° C., 3 rabbits | | |
|---|---|---|---|---|---|---|
| | Exp. 1 | Exp 2 | Exp 3 | 2.5 ug/kg | 10 ug/kg | MPD ug/kg |
| B23 | | 159 | | 0.3 | 0.3 | |
| B24 | 20 | | 17 | 0.9 | 2.4 | 2.5–5 |
| B25 | 0.3 | | 0.5 | 0.6 | 4.2 | |
| B26 | 67 | | | 0.2 | 1.7 | 5 |
| B27 | | 1.65 | | 1.8 | 3.9 | |
| B28 | | | 0.3 | 4.2 | — | |
| B29 | ≧10,000 | | | 0.2 | 0.7 | |
| B30 | | | | 4.3 | — | |
| B31 | ≧10,000 | | | 0.5 | 1.6 | |
| B32 | | | | | | |
| B34 | ≧10,000 | | | 3.5 | 2.8 | |
| B35 | | 86 | | 3.2 | — | |
| B36 | | 1.8 | | 3.4 | — | |
| B37 | | 1.1 | | 2.2 | — | |
| B38 | | ≧3000 | | 3.6 | — | |
| B39 | | ≧3000 | | 3.2 | — | |
| B40 | | ≧3000 | | 3.8 | — | |
| B41 | | | | 6.3 | — | |
| B42 | | | | 5.2 | — | |
| B43 | | 380 | | 3.8 | — | |

It is understood that the foregoing examples are merely illustrative of the present invention. Certain modifications of the compositions and/or methods employed may be made and still achieve the objectives of the invention. Such modifications are contemplated as within the scope of the claimed invention.

REFERENCES

Bulusu, M. A. R. C., Waldstätten, P., Hildebrandt, J., Schütze, E. and G. Schulz (1992) Cyclic Analogues of Lipid A: Synthesis and Biological Activities, *J. Med. Chem.* 35: 3463–3469.

Ikeda, K., Asahara, T. and K. Achiwa (1993) Synthesis of Biologically Active N-acylated L-serine-Containing Glucosaniinide-4-Phosphate Derivatives of Lipid A, *Chem. Phann. Bull.* 41(10): 1879–1881.

Miyajima, K., Ikeda, K. and K. Achiwa (1996) Lipid A and Related Compounds XXXI. Synthesis of Biologically Active N-Acylated L-Serine-Containing D-Glucosaminide 4-Phosphate Derivatives of Lipid A, *Chem. Pharm. Bull.* 44(12): 2268–2273.

Shimizu, T., Akiyama, S., Masuzawa, T., Yanagihara, Y., Nakamoto, S., Takahashi, T., Ikeda, K. and K. Achiwa (1985) Antitumor Activity and Biological Effects of Chemically Synthesized Monosaccharide Analogues of Lipid A in Mice. *Chem. Pharm. Bull.* 33(10): 4621–4624.

Shimizu, T., Sugiyama, K., Iwamoto, Y., Yanagihara, Y., Asahara, T., Ikeda, K. and K. Achiwa (1994) Biological Activities of Chermically Synthesized N-acylated Serine-linked Lipid A Analog in Mice, *Int. J. Immunopharmac.,* 16(8): 659–665.

Shimizu, T., Iida, K., Iwamoto, Y., Yanagihara, Y., Ryoyama, K., Asahara, T., Ikeda, K. and K. Achiwa (1995) Biological Activities and Antitumor Effects of Synthetic Lipid A Analogs Linked N-Acylated Serine, *Int. J. Immunopharmac.,* 17(5): 425–431.

What is claimed is:

1. An immunoeffector compound having the following structure:

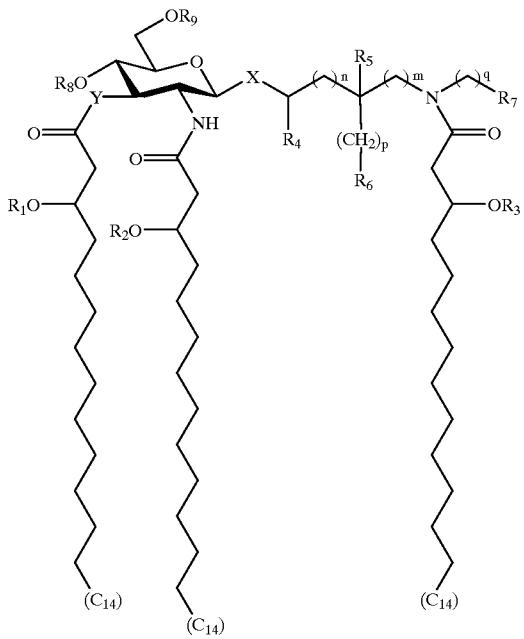

wherein, X is selected from the group consisting of O and S at the axial or equitorial position; Y is selected from the group consisting of O and NH; n, m, p and q are integers from 0 to 6; $R_1$, $R_2$ and $R_3$ are the same or different and are normal fatty acyl residues having from 1 to about 20 carbon atoms and where one of $R_1$, $R_2$ or $R_3$ is optionally hydrogen; $R_4$ and $R_5$ are the same or different and are selected from the group consisting of H and methyl; $R_6$ and $R_7$ are the same or different and are selected from the group consisting of H, hydroxy, alkoxy, phosphono, phosphonooxy, sulfo, sulfooxy, amino, mercapto, cyano, nitro, formyl and carboxy, and esters and amides thereof; and $R_8$ and $R_9$ are the same or different and are selected from the group consisting of phosphono and H, and at least one of $R_8$ and $R_9$ is phosphono.

2. The compound of claim 1, wherein $R_6$ is carboxy.

3. The compound of claim 2, wherein X is O; Y is O; n, m, p and q are 0; $R_1$, $R_2$ and $R_3$ are normal fatty acyl residues having 10 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

4. The compound of claim 2, wherein X is O; Y is O; n, m, p and q are 0; $R_1$, $R_2$ and $R_3$ are normal fatty acyl residues having 12 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

5. The compound of claim 2, wherein X is O; Y is O; n, m, p and q are 0; $R_1$, $R_2$ and $R_3$ are normnal fatty acyl residues having 10 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an R configuration.

6. The compound of claim 2, wherein X is O; Y is O; n, m, p and q are 0; $R_1$, $R_2$ and $R_3$ are normal fatty acyl residues having 8 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

7. The compound of claim 1, wherein $R_6$ is H.

8. The compound of claim 7, wherein X is O; Y is O; n is 2; m, p and q are 0; $R_1$, $R_2$ and $R_3$ are normal fatty acyl residues having 14 carbon atoms; $R_4$, $R_5$ and $R_7$ are H; $R_8$ is phosphono; $R_9$ is H; and $R_1$, $R_2$ and $R_3$ are each attached to a stereogenic center having an R configuration.

9. The compound of claim 7, wherein X is O; Y is O; n is 1, m and p are 0; q is 1; $R_1$, $R_2$ and $R_3$ are normal fatty acyl residues having 10 carbon atoms; $R_4$ and $R_5$ are H; $R_7$ is carboxy; $R_8$ is phosphono; $R_9$ is H; and $R_1$, $R_2$ and $R_3$ are each attached to a stereogenic center having an R configuration.

10. The compound of claim 7, wherein X is O; Y is O; m, n, p and q are 0; $R_1$, $R_2$ and $R_3$ are normal fatty acyl residues having 14 carbon atoms; $R_4$, $R_5$ and $R_7$ are H; $R_8$ is phosphono; $R_9$ is H; and $R_1$, $R_2$ and $R_3$ are each attached to a stereogenic center having an R configuration.

11. The compound of claim 7, wherein X is O; Y is O; m, n, p and q are 0; $R_1$, $R_2$ and $R_3$ are normal fatty acyl residues having 10 carbon atoms; $R_4$, $R_5$ and $R_7$ are H; $R_8$ is phosphono; $R_9$ is H; and $R_1$, $R_2$ and $R_3$ are each attached to a stereogenic center having an R configuration.

12. The compound of claim 7, wherein X is O; Y is O; m, p and q are 0; n is 1; $R_1$, $R_2$ and $R_3$ are normal fatty acyl residues having 14 carbons; $R_4$, $R_5$ and $R_7$ are H; $R_8$ is phosphono; $R_9$ is H; and $R_1$, $R_2$ and $R_3$ are each attached to a stereogenic center having an R configuration.

13. The compound of claim 1, wherein $R_6$ is hydroxy.

14. The compound of claim 13, wherein X is O; Y is O; m, n and q are 0; p is 1; $R_1$, $R_2$ and $R_3$ are normal fatty acyl residues having 12 carbon atoms; $R_4$ and $R_5$ are H; $R_7$ is H; $R_8$ is phosphono; and $R_9$ is H; $R_1$, $R_2$ and $R_3$ are each attached to a stereogenic center having an R configuration; and $R_5$ is attached to a stereogenic center having an S configuration.

15. The compound of claim 13, wherein X is O; Y is O; m and q are 0; n and p are 1; $R_1$, $R_2$ and $R_3$ are normal fatty acyl residues having 10 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

16. The compound of claim 13, wherein X is O; Y is O; m, n and q are 0; p is 2; $R_1$, $R_2$ and $R_3$ are normal fatty acyl residues having 10 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

17. The compound of claim 13, wherein X is O; Y is O; m, n and q are 0; p is 1; $R_1$, $R_2$ and $R_3$ are normal fatty acyl residues having 14 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an R configuration.

18. The compound of claim 13, wherein X is O; Y is O; m, n and q are 0; p is 1; $R_1$, $R_2$ and $R_3$ are normal fatty acyl residues having 14 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

19. The compound of claim 13, wherein X is O; Y is O; m, n and q are 0; p is 1; $R_1$, $R_2$ and $R_3$ are normal fatty acyl residues having 11 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

20. The compound of claim 13, wherein X is O; Y is O; m, n and q are 0; p is 1; $R_1$, $R_2$ and $R_3$ are normal fatty acyl residues having 10 carbon atoms; $R_4$, $R_5$ and $R_7$ are H; $R_8$ is phosphono; $R_9$ is H; $R_1$, $R_2$ and $R_3$ are each attached to a stereogenic center having an R configuration; and $R_5$ is attached to a stereogenic center having an S configuration.

21. The compound of claim 1, wherein X is O; Y is O; m, n, p and q are 0; $R_1$, $R_2$ and $R_3$ are normal fatty acyl residues having 10 carbon atoms; $R_4$ and $R_5$ are H; $R_6$ is amino carbonyl; $R_7$ is H; $R_8$ is phosphono; and $R_9$ is H; $R_1$, $R_2$ and $R_3$ are each attached to a stereogenic center having an R configuration; and $R_5$ is attached to a stereogenic center having an S configuration.

22. The compound of claim 1, wherein $R_1$ is hydrogen.

23. The compound of claim 1, wherein $R_2$ is hydrogen.

24. The compound of claim 1, wherein $R_3$ is hydrogen.

25. A method for enhancing the immune response of a mammal comprising administering to the mammal an effective amount of a compound of claim 1.

26. A vaccine composition comprising a compound of claim 1, an antigen and a suitable carrier.

27. A pharmaceutical composition comprising a compound of claim 1 and a pharmaceutically acceptable carrier.

28. The composition of claim 27, wherein said pharmaceutically acceptable carrier is an aqueous composition comprising water and one or more surfactants selected from the group consisting of glycodeoxycholate, deoxycholate, sphingomyelin, sphingosine, phosphatidylcholine, 1,2-Dimyristoyl-sn-glycero-3-phosphoethanolamine, L-α-Phosphatidylethanolamine, and 1,2-Dipalmitoyl-sn-glycero-3-phosphocholine, or a mixture thereof.

29. The composition of claim 28, wherein said one or more surfactant is 1,2-Dipalmitoyl-sn-glycero-3-phosphocholine.

30. The composition of claim 28, wherein the molar ratio of said compound to surfactant is from about 10:1 to about 1:25.

31. The composition of claim 28, wherein the molar ratio of said compound to surfactant is from about 4:1 to about 1:9.

32. The composition of claim 27, wherein said carrier is a stable emulsion comprising a metabolizable oil, one or more surfactants, an antioxidant and a component to make the emulsion isotonic.

33. The composition of claim 32, wherein said stable emulsion comprises 1–10% v/v squalene, 0.9% w/v PLURONIC-F68 block co-polymer, 1.9% w/v egg phosphatidyl choline, 1.75% v/v glycerol and 0.05% w/v a tocopherol.

34. The composition of claim 27 wherein said carrier is a suspension comprising aluminum hydroxide, calcium hydroxide, calcium phosphate or tyrosine adsorbate.

35. The composition of claim 27 wherein said carrier is an aqueous solution or aqueous micellar dispersion comprising triethylamine or triethanolamine.

36. The composition of claim 27 wherein said carrier comprises microspheres or microparticles, and the compound of claim 1 is within the matrix of the microspheres or microparticles or adsorbed thereon.

* * * * *